(12) United States Patent
Markison et al.

(10) Patent No.: US 11,896,367 B2
(45) Date of Patent: *Feb. 13, 2024

(54) WIRELESS IN-SHOE PHYSICAL ACTIVITY MONITORING

(71) Applicant: ATHALONZ, LLC, Mesa, AZ (US)

(72) Inventors: Timothy W. Markison, Mesa, AZ (US); Sayfe Kiaei, Fountain Hills, AZ (US); Gary McCoy, Gilbert, AZ (US)

(73) Assignee: SIGMASENSE, LLC., Wilmington, DE (US)

(*) Notice: Subject to any disclaimer, the term of this patent is extended or adjusted under 35 U.S.C. 154(b) by 197 days.

This patent is subject to a terminal disclaimer.

(21) Appl. No.: 17/485,613

(22) Filed: Sep. 27, 2021

(65) Prior Publication Data

US 2022/0007968 A1   Jan. 13, 2022

Related U.S. Application Data

(63) Continuation of application No. 15/680,027, filed on Aug. 17, 2017, now Pat. No. 11,129,547.

(Continued)

(51) Int. Cl.
  *A61B 5/00*   (2006.01)
  *A61B 5/103*  (2006.01)
  (Continued)

(52) U.S. Cl.
  CPC ........... *A61B 5/1036* (2013.01); *A43B 3/34* (2022.01); *A61B 5/002* (2013.01);
  (Continued)

(58) Field of Classification Search
  CPC ... A61B 5/1036; A61B 5/002; A61B 5/02055; A61B 5/1118; A61B 5/16; A61B 5/6802;
  (Continued)

(56) References Cited

U.S. PATENT DOCUMENTS 3,184,739 A   5/1965   Frederick
3,795,911 A   3/1974   Hammack
(Continued)

FOREIGN PATENT DOCUMENTS

CN   103995626 A   8/2014
CN   104182105 A   12/2014

OTHER PUBLICATIONS

"F-Scan System." Tekscan, Inc. https://www.tekscan.com/products-solutions/systems/f-scan-system. Accessed Aug. 18, 2017.
(Continued)

*Primary Examiner* — May A Abouelela
(74) *Attorney, Agent, or Firm* — GARLICK & MARKISON; Timothy W. Markison

(57) ABSTRACT

A method includes obtaining foot force data that is created by sampling, in accordance with a sampling signal, data from a plurality of pressure sensing elements of a shoe sensor system, where the plurality of pressure sensing elements are distributed in a pattern having a first pressure sensing element at a fifth metatarsal area of a lateral wall of an insole of a shoe associated with the shoe sensor system, and a second pressure sensing element at a first metatarsal area of a medial wall of the insole. The method further includes processing the foot force data to determine a horizontal force of a foot of a user of the shoe sensor system while the user is performing a movement while wearing the shoe.

20 Claims, 38 Drawing Sheets

Related U.S. Application Data

(60) Provisional application No. 62/376,555, filed on Aug. 18, 2016.

(51) Int. Cl.

| | |
|---|---|
| *A61B 5/11* | (2006.01) |
| *A43B 3/34* | (2022.01) |
| *A61B 5/0205* | (2006.01) |
| *A61B 5/16* | (2006.01) |
| *A63B 24/00* | (2006.01) |
| *A63B 71/06* | (2006.01) |
| *H04Q 9/00* | (2006.01) |
| *G01S 13/42* | (2006.01) |
| *G01S 13/46* | (2006.01) |
| *G01S 13/58* | (2006.01) |
| *G01S 13/72* | (2006.01) |
| *G01S 13/88* | (2006.01) |
| *A61B 5/024* | (2006.01) |
| *A61B 5/08* | (2006.01) |

(52) U.S. Cl.
CPC ........ *A61B 5/02055* (2013.01); *A61B 5/1118* (2013.01); *A61B 5/16* (2013.01); *A61B 5/6802* (2013.01); *A61B 5/7275* (2013.01); *A61B 5/743* (2013.01); *A63B 24/0062* (2013.01); *A63B 71/06* (2013.01); *G01S 13/42* (2013.01); *G01S 13/46* (2013.01); *G01S 13/58* (2013.01); *G01S 13/726* (2013.01); *G01S 13/88* (2013.01); *H04Q 9/00* (2013.01); *A61B 5/024* (2013.01); *A61B 5/0816* (2013.01); *A61B 2560/0214* (2013.01); *A61B 2562/0219* (2013.01); *G01S 2013/468* (2013.01); *H04Q 2209/40* (2013.01); *H04Q 2209/84* (2013.01); *H04Q 2209/845* (2013.01)

(58) Field of Classification Search
CPC ....... A61B 5/7275; A61B 5/743; A61B 5/024; A61B 5/0816; A61B 2560/0214; A61B 2562/0219; A43B 3/34; A63B 24/0062; A63B 71/06; G01S 13/42; G01S 13/46; G01S 13/58; G01S 13/726; G01S 13/88; G01S 2013/468; H04Q 9/00; H04Q 2209/40; H04Q 2209/84; H04Q 2209/845; G16H 50/30
See application file for complete search history.

(56) References Cited

U.S. PATENT DOCUMENTS

| | | | |
|---|---|---|---|
| 3,953,856 A | 4/1976 | Hammack | |
| 4,992,797 A | 2/1991 | Gjessing | |
| 5,247,307 A | 9/1993 | Gandar | |
| 5,410,314 A | 4/1995 | Frush | |
| 5,925,001 A * | 7/1999 | Hoyt | A61B 5/1036 |
| | | | 600/595 |
| 6,218,972 B1 | 4/2001 | Groshong | |
| 6,222,481 B1 | 4/2001 | Abrahamson | |
| 6,665,013 B1 | 12/2003 | Fossum et al. | |
| 7,394,046 B2 | 7/2008 | Olsson | |
| 7,528,755 B2 | 5/2009 | Hammerschmidt | |
| 7,648,441 B2 * | 1/2010 | Silk | A61B 5/1038 |
| | | | 600/587 |
| 7,717,962 B2 * | 5/2010 | Wilson | A61F 2/70 |
| | | | 600/595 |
| 7,911,339 B2 * | 3/2011 | Vock | A43B 1/0036 |
| | | | 340/693.1 |
| 8,011,229 B2 * | 9/2011 | Lieberman | A61B 5/4023 |
| | | | 73/65.01 |
| 8,031,094 B2 | 10/2011 | Hotelling | |
| 8,089,289 B1 | 1/2012 | Kremin et al. | |
| 8,113,843 B2 | 2/2012 | Naya | |
| 8,279,180 B2 | 10/2012 | Hotelling et al. | |
| 8,280,681 B2 * | 10/2012 | Vock | G01P 15/0891 |
| | | | 600/587 |
| 8,375,784 B2 * | 2/2013 | Bamberg | A61B 5/6807 |
| | | | 73/379.05 |
| 8,384,551 B2 * | 2/2013 | Ross | A43B 7/00 |
| | | | 600/595 |
| 8,467,979 B2 * | 6/2013 | Sobolewski | A43B 7/1445 |
| | | | 600/595 |
| 8,537,110 B2 | 9/2013 | Kruglick | |
| 8,547,114 B2 | 10/2013 | Kremin | |
| 8,587,535 B2 | 11/2013 | Oda et al. | |
| 8,625,726 B2 | 1/2014 | Kuan | |
| 8,657,681 B2 | 2/2014 | Kim | |
| 8,686,862 B2 * | 4/2014 | Dunham | A43B 3/38 |
| | | | 340/286.01 |
| 8,692,675 B2 * | 4/2014 | Agrawal | A61B 5/0051 |
| | | | 600/587 |
| 8,784,115 B1 * | 7/2014 | Chuang | A63B 24/00 |
| | | | 706/14 |
| 8,821,417 B2 * | 9/2014 | McGregor | A61B 5/0004 |
| | | | 600/595 |
| 8,870,795 B2 * | 10/2014 | Kim | A61B 5/1038 |
| | | | 600/592 |
| 8,966,400 B2 | 2/2015 | Yeap | |
| 8,968,218 B2 * | 3/2015 | Wukasch | A61B 5/6829 |
| | | | 600/595 |
| 8,982,097 B1 | 3/2015 | Kuzo et al. | |
| 9,002,680 B2 * | 4/2015 | Nurse | A43B 3/00 |
| | | | 702/41 |
| 9,081,437 B2 | 7/2015 | Oda | |
| 9,201,547 B2 | 12/2015 | Elias | |
| 9,256,281 B2 | 2/2016 | Ur | |
| 9,349,301 B2 | 5/2016 | Ur | |
| 9,352,207 B2 | 5/2016 | Balakrishnan | |
| 9,393,697 B1 | 7/2016 | Beardsley | |
| 9,756,895 B2 | 9/2017 | Rice | |
| 9,763,489 B2 | 9/2017 | Amos | |
| 9,810,591 B2 | 11/2017 | Walker | |
| 9,810,709 B2 * | 11/2017 | Balakrishnan | G04G 21/00 |
| 9,962,111 B2 * | 5/2018 | Balakrishnan | A61B 5/1112 |
| 10,007,335 B2 | 6/2018 | Lee | |
| 10,024,660 B2 * | 7/2018 | Otis | A61B 5/6807 |
| 10,070,682 B2 | 9/2018 | Rubin | |
| 10,307,081 B2 | 6/2019 | Nino | |
| 2004/0138575 A1 | 7/2004 | Ueyama | |
| 2005/0049816 A1 | 3/2005 | Oda | |
| 2007/0028486 A1 * | 2/2007 | Montanya | A43B 3/36 |
| | | | 36/137 |
| 2007/0068244 A1 | 3/2007 | Billing | |
| 2007/0112285 A1 | 5/2007 | Dar | |
| 2007/0142955 A1 | 6/2007 | Lin | |
| 2007/0173903 A1 * | 7/2007 | Goren | A61N 1/32 |
| | | | 600/595 |
| 2007/0246334 A1 * | 10/2007 | Elkins | A61F 2/68 |
| | | | 600/300 |
| 2007/0247306 A1 | 10/2007 | Case | |
| 2008/0082025 A1 * | 4/2008 | Hughes | A61B 5/6829 |
| | | | 600/595 |
| 2008/0108913 A1 * | 5/2008 | Lengsfeld | A61B 5/1038 |
| | | | 600/595 |
| 2008/0243265 A1 * | 10/2008 | Lanier | A61F 2/583 |
| | | | 600/587 |
| 2008/0285805 A1 * | 11/2008 | Luinge | G06F 3/011 |
| | | | 382/128 |
| 2008/0287832 A1 * | 11/2008 | Collins | A61B 5/1038 |
| | | | 600/587 |
| 2009/0069898 A1 * | 3/2009 | Wilson | A61F 2/70 |
| | | | 600/300 |
| 2009/0235739 A1 * | 9/2009 | Morris Bamberg | A61B 5/6807 |
| | | | 702/141 |
| 2009/0240171 A1 * | 9/2009 | Morris Bamberg | A61B 5/1038 |
| | | | 600/595 |
| 2010/0041959 A1 * | 2/2010 | Iwata | A61B 5/1038 |
| | | | 601/1 |

(56) References Cited

U.S. PATENT DOCUMENTS

| | | | |
|---|---|---|---|
| 2010/0198111 A1* | 8/2010 | Milani | A61B 5/6807 600/592 |
| 2011/0054359 A1* | 3/2011 | Sazonov | A61B 5/1118 600/595 |
| 2011/0063154 A1 | 3/2011 | Hotelling et al. | |
| 2011/0087445 A1 | 4/2011 | Sobolewski | |
| 2011/0119027 A1 | 5/2011 | Zhu | |
| 2011/0131838 A1* | 6/2011 | Pas | A61B 5/1036 318/116 |
| 2011/0152695 A1* | 6/2011 | Granqvist | G16H 20/30 600/595 |
| 2011/0251520 A1* | 10/2011 | Shieh | A43D 1/02 600/587 |
| 2011/0267219 A1 | 11/2011 | Kisliansky | |
| 2011/0298745 A1 | 12/2011 | Souchkov | |
| 2011/0301504 A1* | 12/2011 | Lan | A61B 5/1036 600/592 |
| 2011/0304497 A1* | 12/2011 | Molyneux | G01S 13/751 342/42 |
| 2011/0313714 A1* | 12/2011 | Lieberman | A61B 5/1123 702/139 |
| 2012/0059235 A1* | 3/2012 | Davies | A61B 5/1123 600/595 |
| 2012/0092169 A1* | 4/2012 | Kaiser | G16H 50/20 600/587 |
| 2012/0095356 A1* | 4/2012 | Oleson | A44C 5/0007 600/595 |
| 2012/0234111 A1 | 9/2012 | Molyneux | |
| 2012/0253234 A1* | 10/2012 | Yang | A61B 5/1038 600/595 |
| 2012/0278031 A1 | 11/2012 | Oda | |
| 2012/0291563 A1 | 11/2012 | Schrock | |
| 2013/0041617 A1* | 2/2013 | Pease | A43B 3/34 702/139 |
| 2013/0110011 A1* | 5/2013 | McGregor | A61B 5/1118 600/595 |
| 2013/0190903 A1* | 7/2013 | Balakrishnan | A63B 71/06 700/91 |
| 2013/0278447 A1 | 10/2013 | Kremin | |
| 2014/0024972 A1* | 1/2014 | Greene | A61B 5/1038 600/595 |
| 2014/0174205 A1 | 6/2014 | Clarke | |
| 2014/0222173 A1 | 8/2014 | Giedowyn | |
| 2014/0327644 A1 | 11/2014 | Mohindra | |
| 2014/0336796 A1* | 11/2014 | Agnew | G09B 5/00 700/91 |
| 2015/0091847 A1 | 4/2015 | Chang | |
| 2015/0100105 A1* | 4/2015 | Kiani | A61B 5/0002 607/49 |
| 2015/0133754 A1* | 5/2015 | Freeman | A61F 2/586 600/407 |
| 2015/0157272 A1* | 6/2015 | Balakrishnan | A61B 5/1123 600/595 |
| 2015/0289820 A1* | 10/2015 | Miller | A61B 5/02438 600/300 |
| 2015/0313308 A1 | 11/2015 | Rice | |
| 2015/0346889 A1 | 12/2015 | Chen | |
| 2016/0029928 A1* | 2/2016 | Jang | G07C 1/22 600/595 |
| 2016/0058326 A1* | 3/2016 | Winfree | A61B 5/6807 600/592 |
| 2016/0143562 A1* | 5/2016 | Ashby | A61B 5/486 600/595 |
| 2016/0150854 A1* | 6/2016 | Hockerson | A43B 7/148 36/28 |
| 2016/0174899 A1* | 6/2016 | Besnard | A43B 3/101 600/595 |
| 2016/0188049 A1 | 6/2016 | Yang et al. | |
| 2016/0262485 A1* | 9/2016 | Walker | A61B 5/6807 |
| 2016/0287937 A1* | 10/2016 | Fitzgerald | G09B 19/0038 |
| 2016/0309829 A1* | 10/2016 | Molyneux | A63B 24/0062 |
| 2016/0324445 A1 | 11/2016 | Kim | |
| 2016/0338411 A1 | 11/2016 | Liu | |
| 2016/0037534 A1 | 12/2016 | Czaja | |
| 2016/0345664 A1 | 12/2016 | Kohatsu | |
| 2016/0345665 A1* | 12/2016 | Kohatsu | A43D 1/02 |
| 2016/0345666 A1* | 12/2016 | Kohatsu | A43B 13/146 |
| 2016/0349076 A1* | 12/2016 | Campos Gallo | G01L 1/16 |
| 2016/0351771 A1 | 12/2016 | Schneider | |
| 2016/0370854 A1 | 12/2016 | Steele | |
| 2016/0375346 A1 | 12/2016 | Czaja | |
| 2017/0105476 A1* | 4/2017 | Morrison | A43B 13/36 |
| 2017/0127749 A1* | 5/2017 | Boeck | A61B 5/0002 |
| 2017/0164684 A1* | 6/2017 | Vock | A43B 7/00 |
| 2017/0225033 A1 | 8/2017 | Czaja | |
| 2017/0265560 A1* | 9/2017 | Beers | A43C 11/165 |
| 2018/0049670 A1 | 2/2018 | Markison | |
| 2018/0049671 A1 | 2/2018 | Markison | |
| 2018/0049703 A1 | 2/2018 | Markison | |
| 2018/0256071 A1 | 9/2018 | Mathieu | |
| 2018/0275824 A1 | 9/2018 | Li | |
| 2019/0133242 A1* | 5/2019 | Xia | A43B 3/34 |

OTHER PUBLICATIONS

Munk-Stander, Jacob. "Evaluation of Piezoelectric Film Sensors for In-Shoe Pressure Measurement." Technical Report No. 06/04. Dept. of Computer Science, University of Copenhagen, Denmark. Feb. 16, 2006. 21 pages.

Rampp, A., Barth, J., Schulein, S., Gar..mann, K. G., Klucken, J., & Eskofier, B. M. (2014). Inertial sensor-based stride parameter calculation from gait sequences in geriatric patients. IEEE transactions on biomedical engineering, 62(4), 1089-1097. (Year: 2014).

Willson, J. D., & Kernozek, T. W. (1999). Plantar loading and cadence alterations with fatigue. Medicine and science in sports and exercise, 31(12), 1828-1833. (Year: 1999).

Baker; How delta-sigma ADCs work, Part 1; Analog Applications Journal; Oct. 1, 2011; 6 pgs.

Brian Pisani, Digital Filter Types in Delta-Sigma ADCs, Application Report SBAA230, May 2017, pp. 1-8, Texas Instruments Incorporated, Dallas, Texas.

* cited by examiner

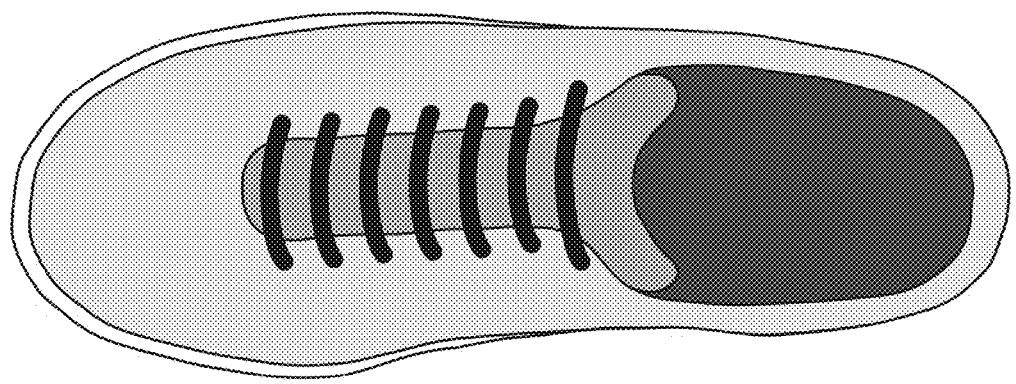
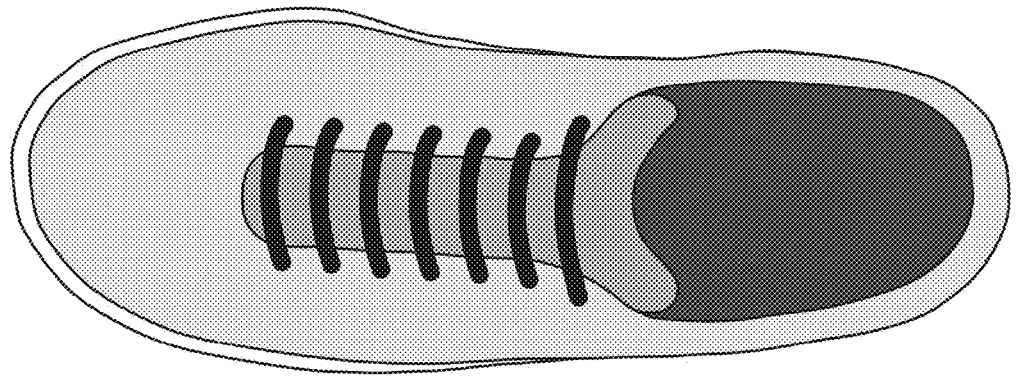
FIG. 1
top view

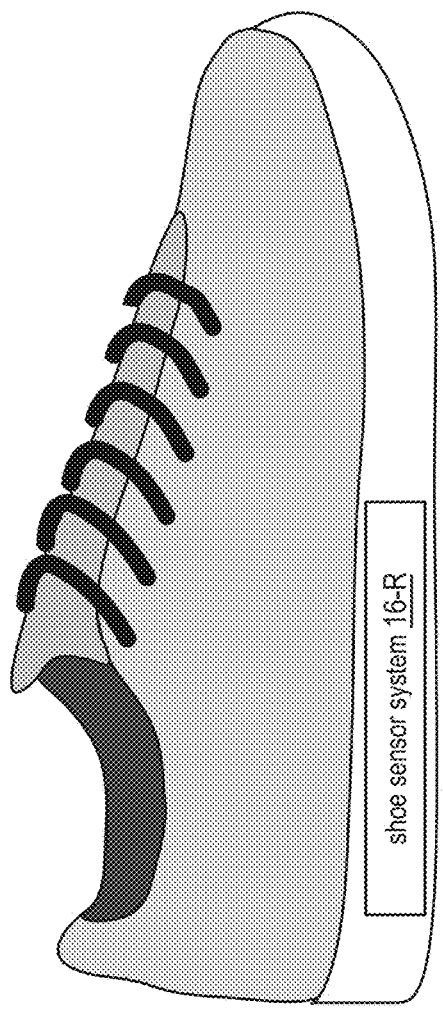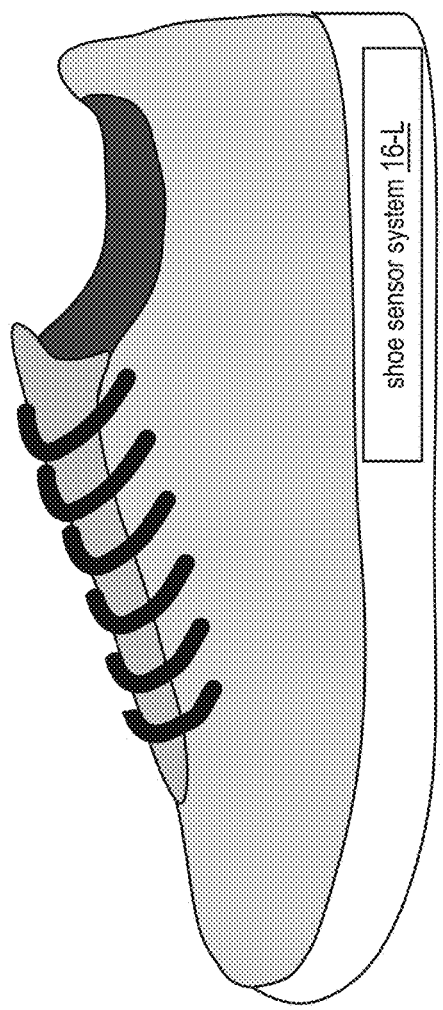

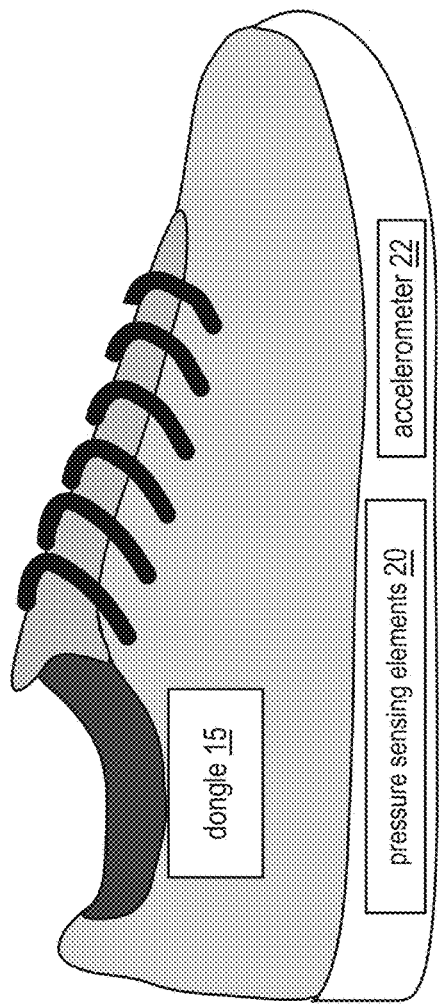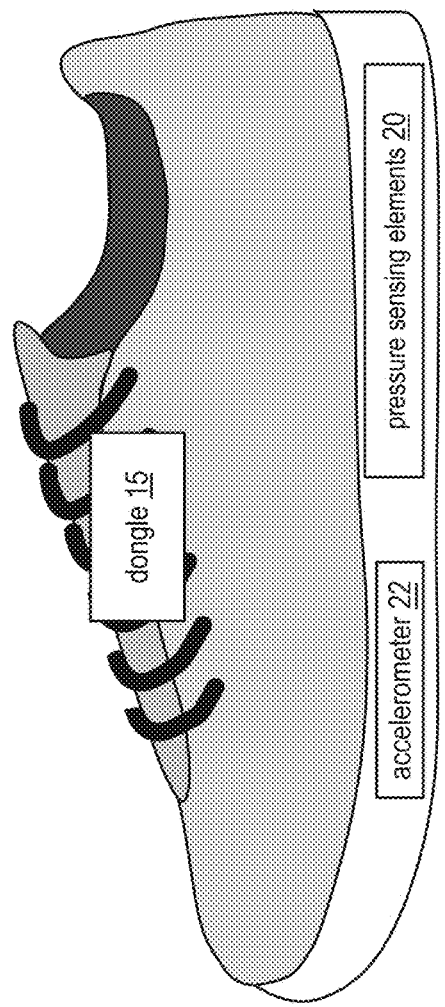

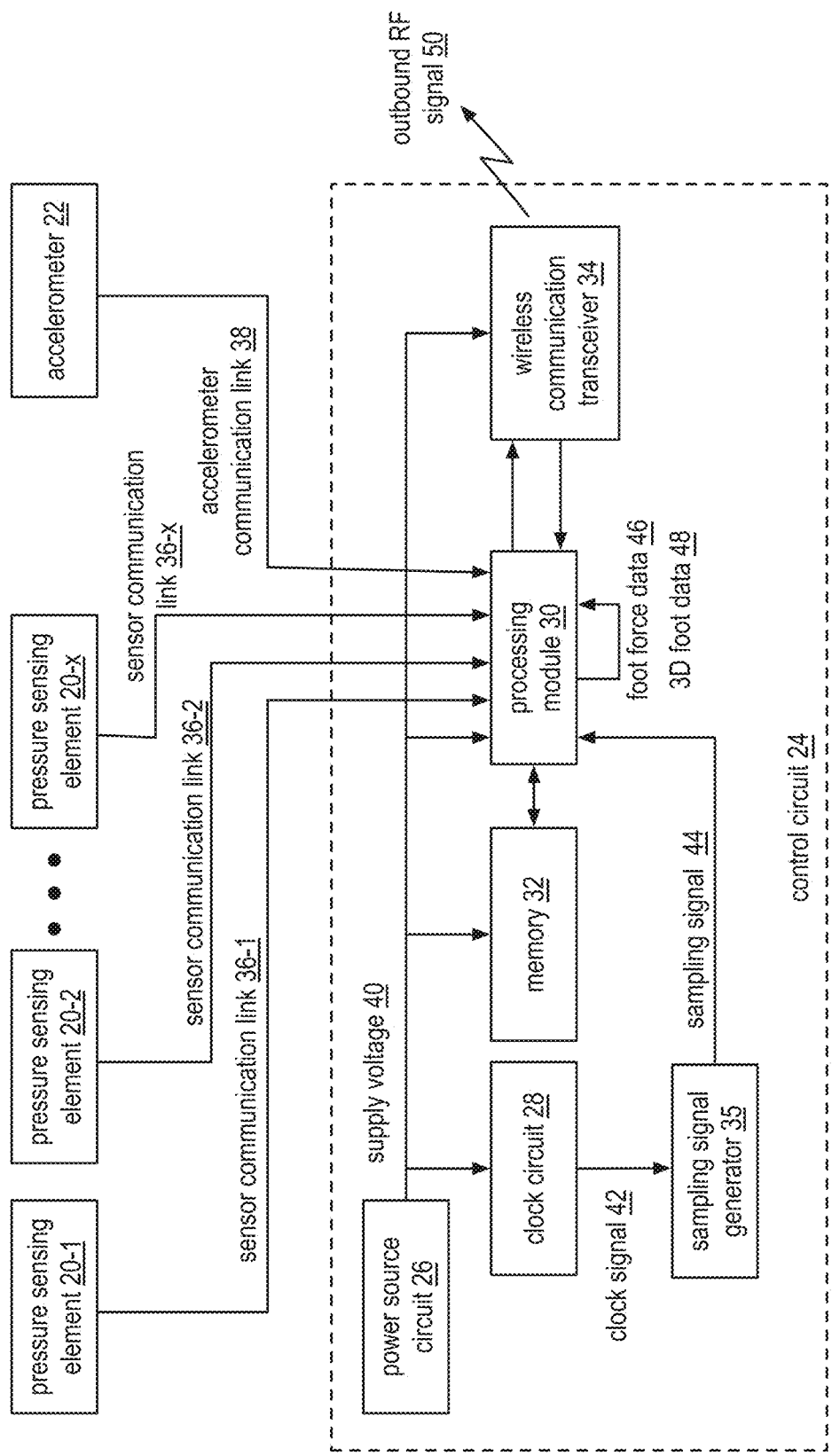

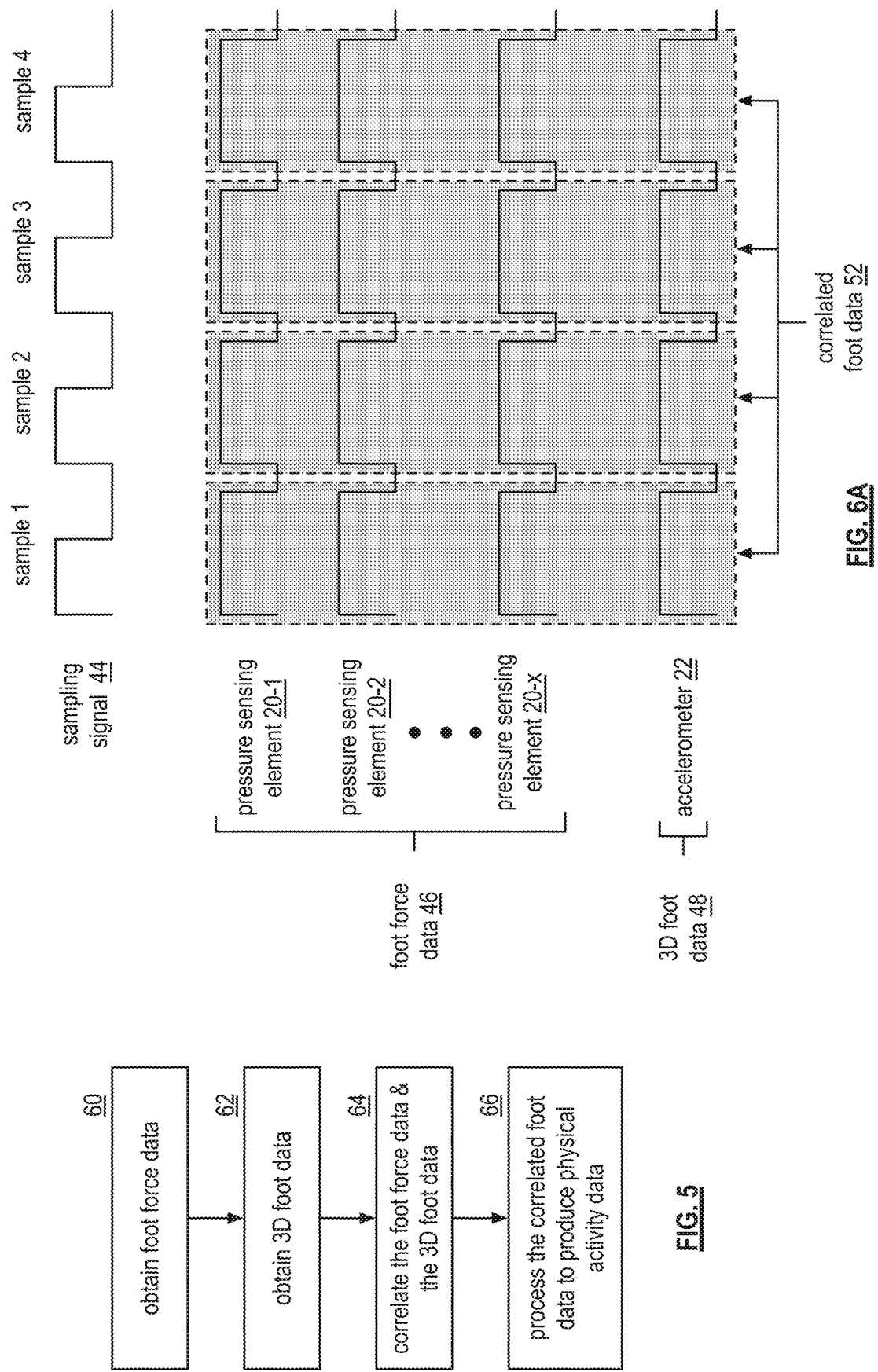

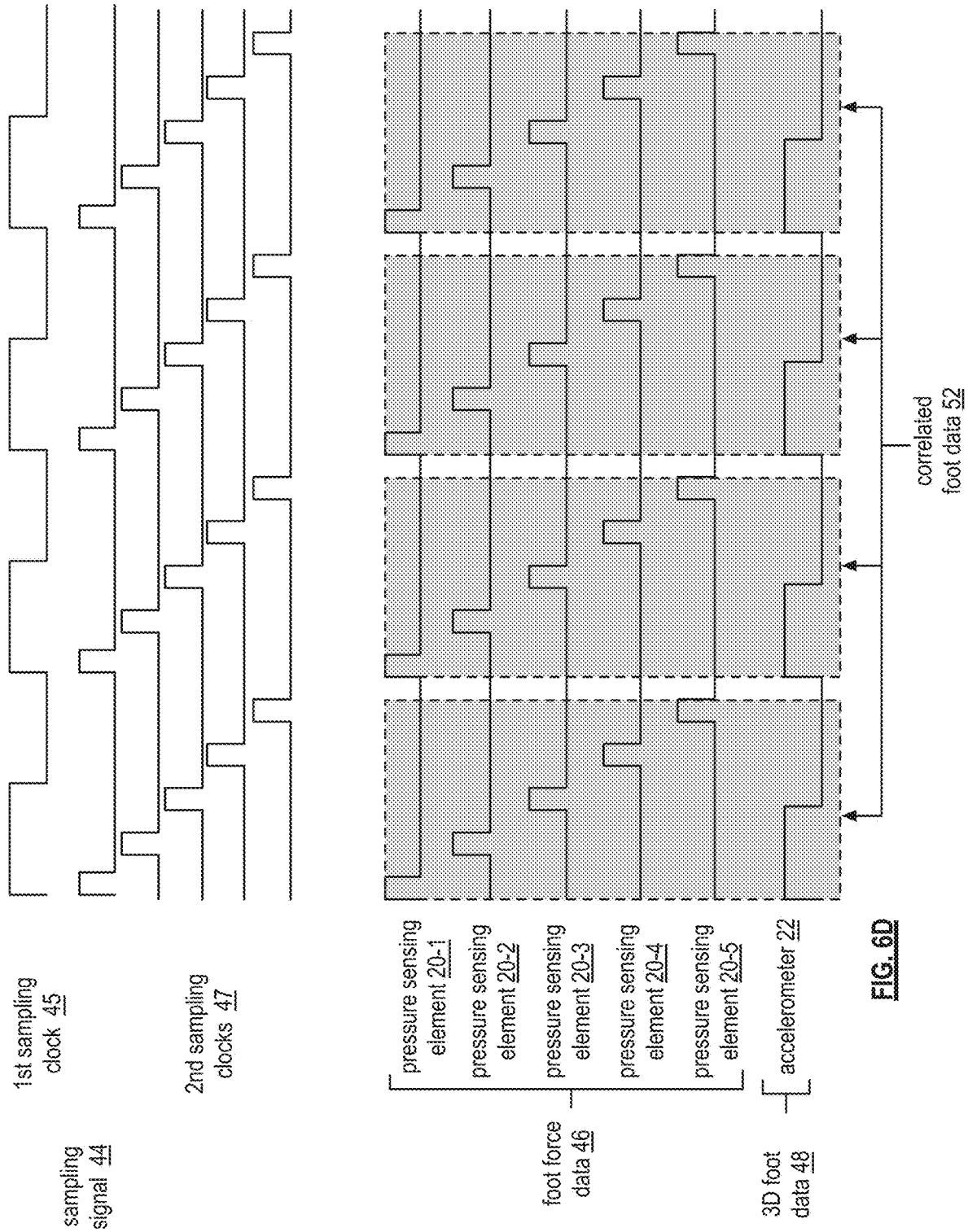

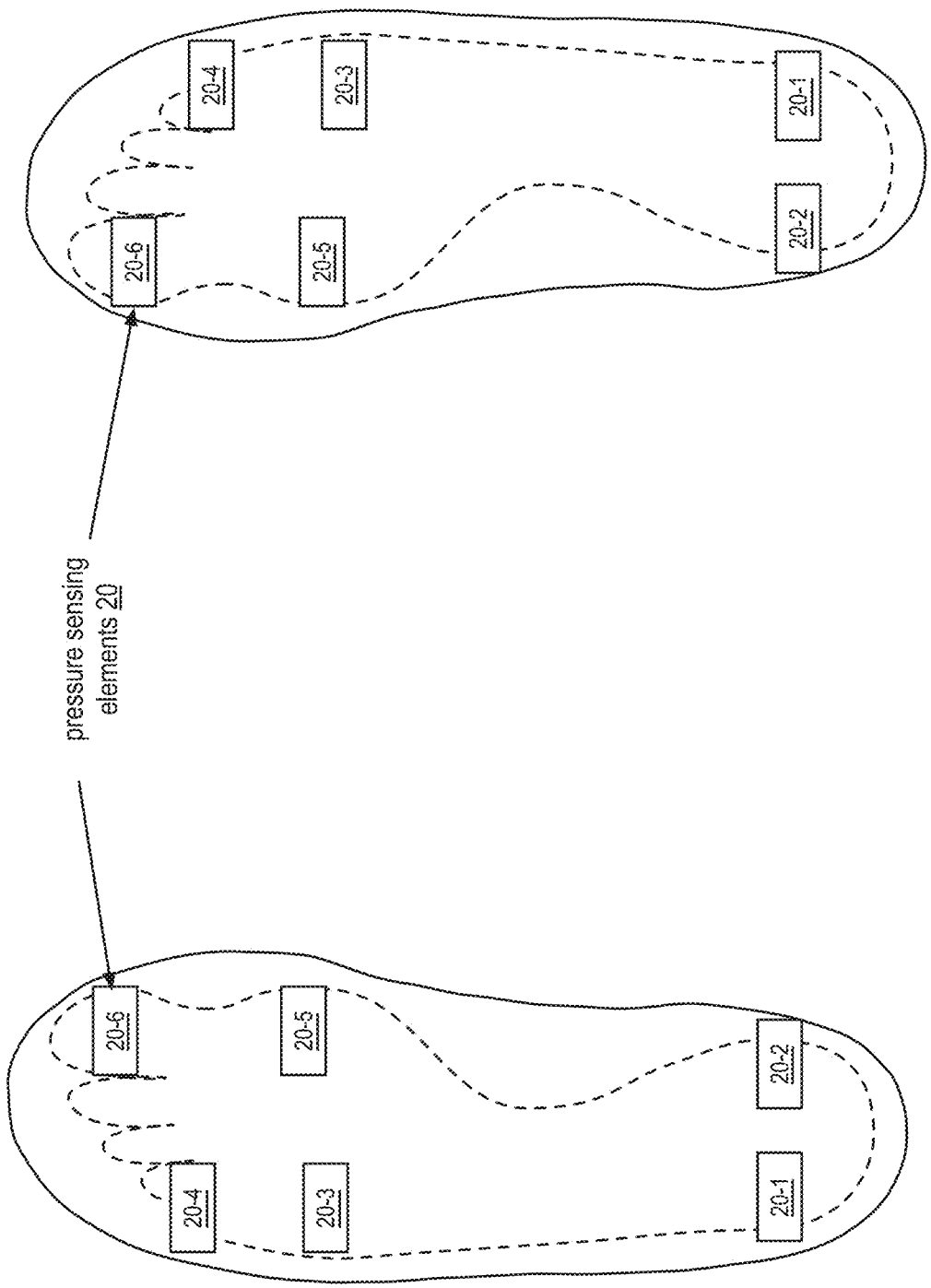

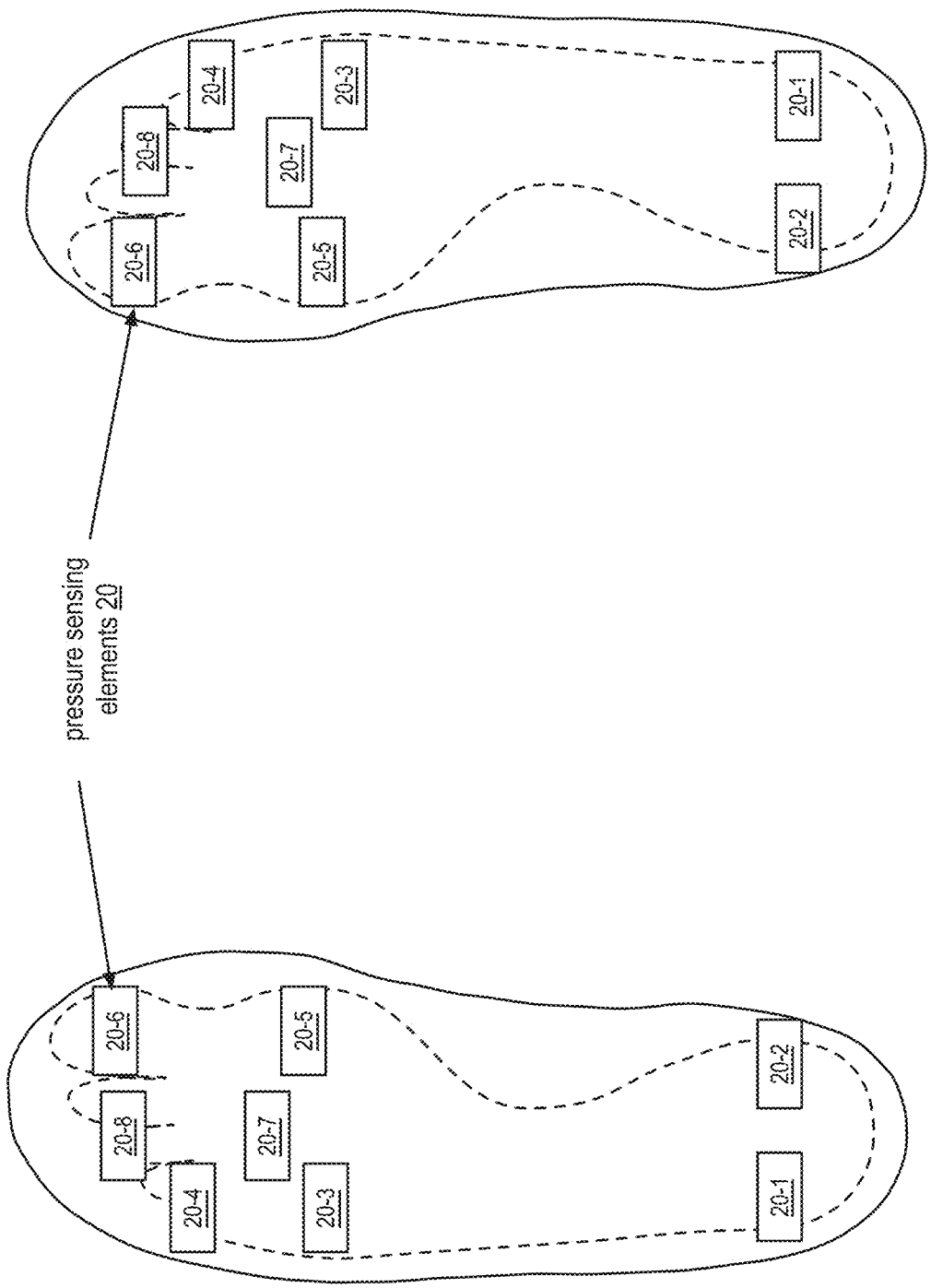

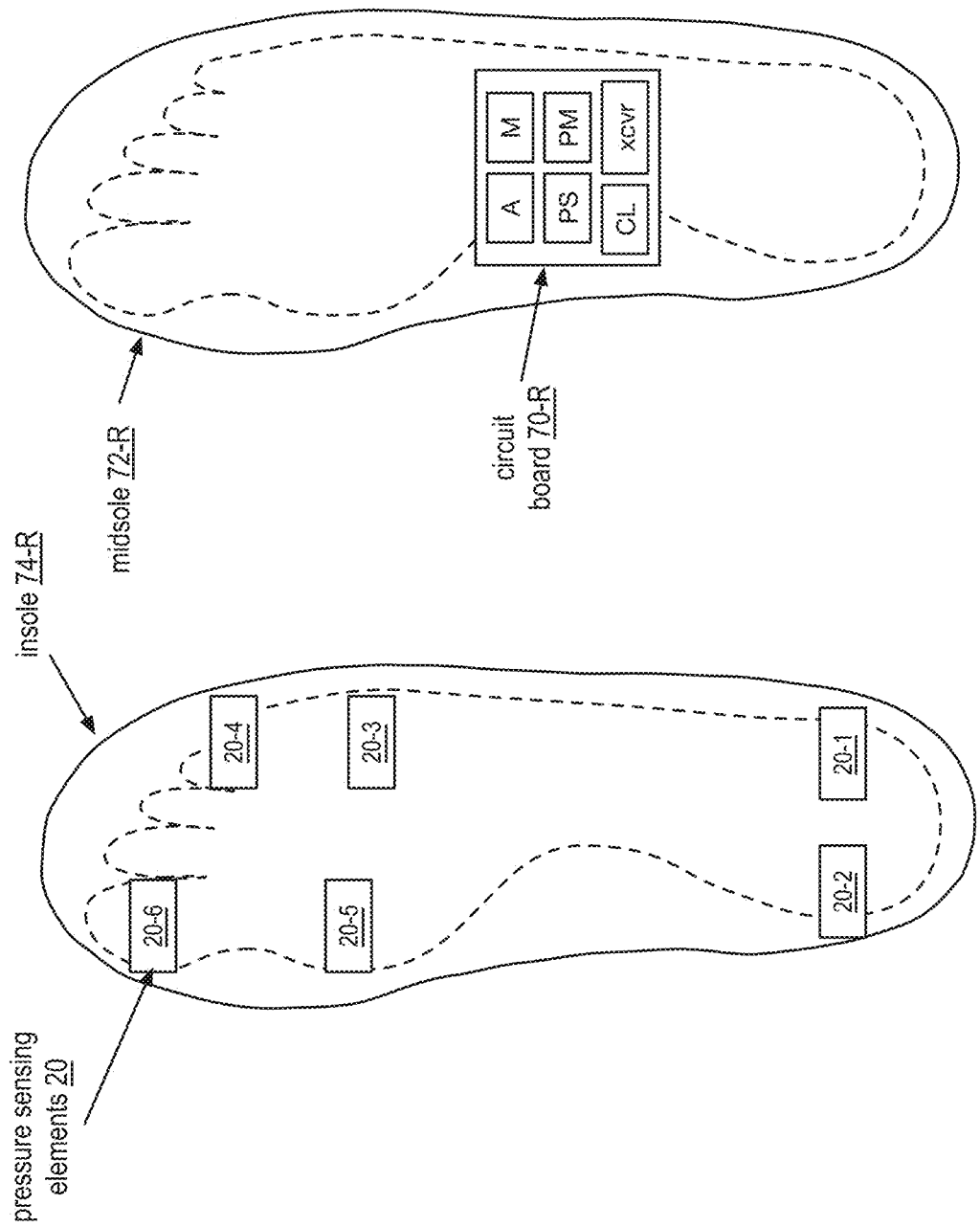

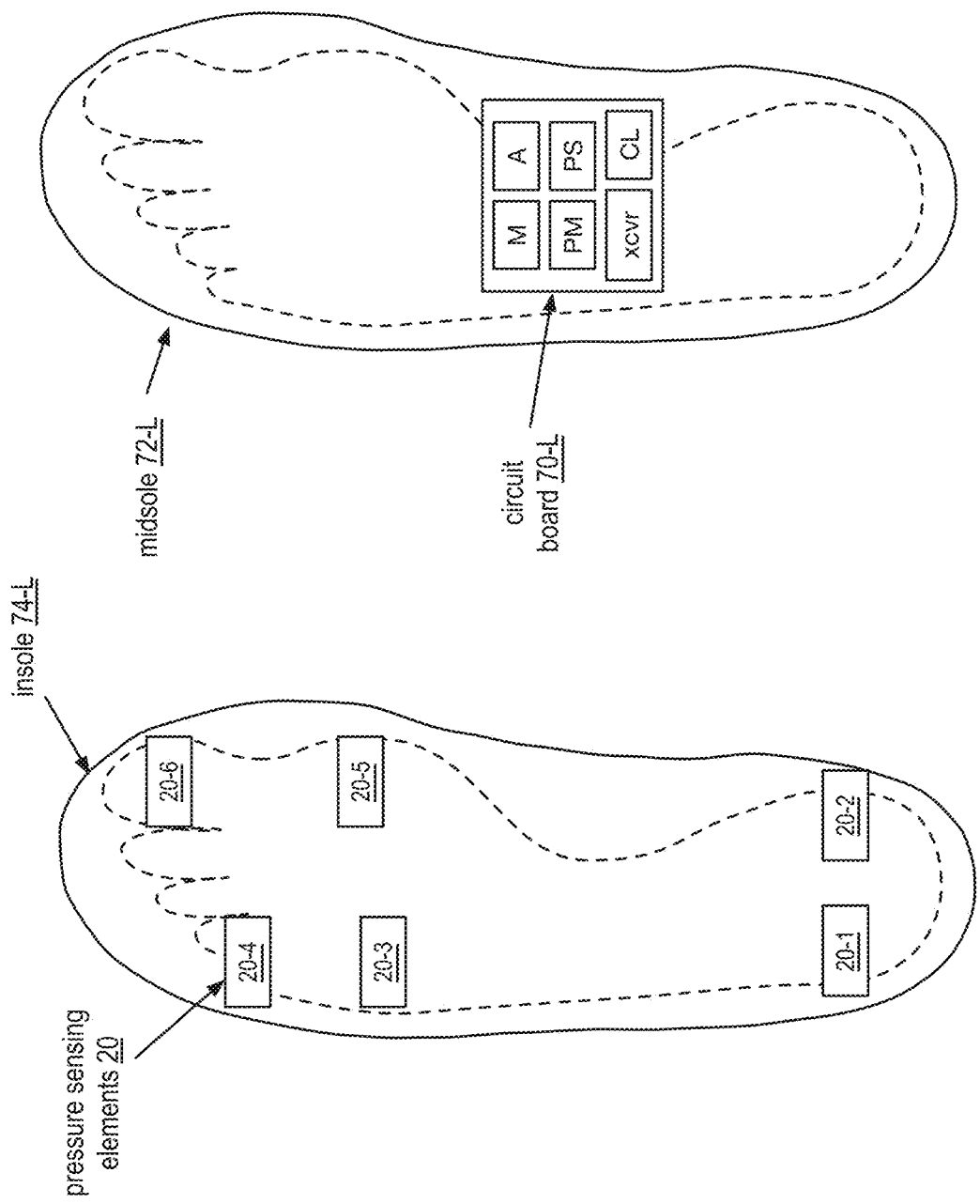

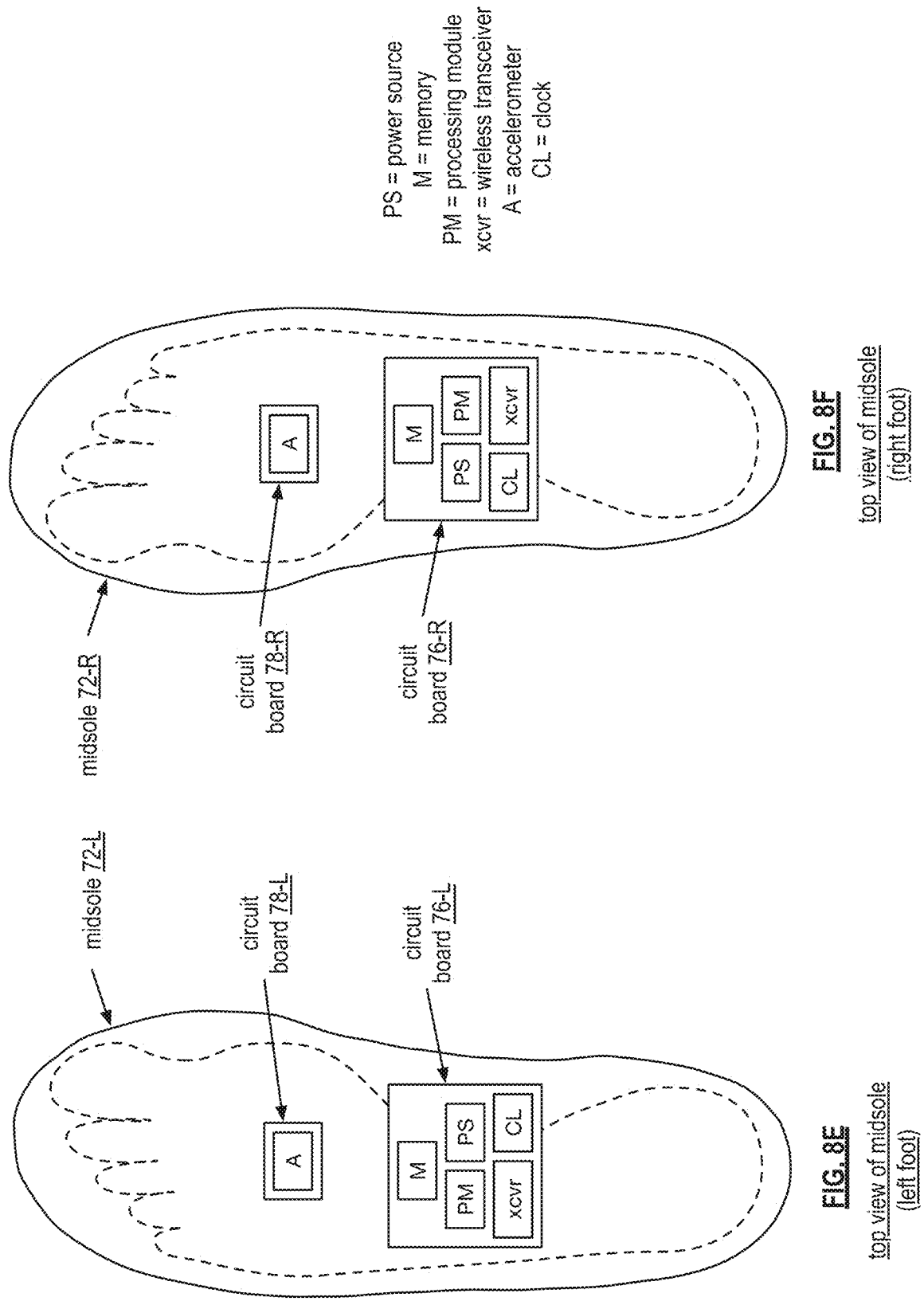

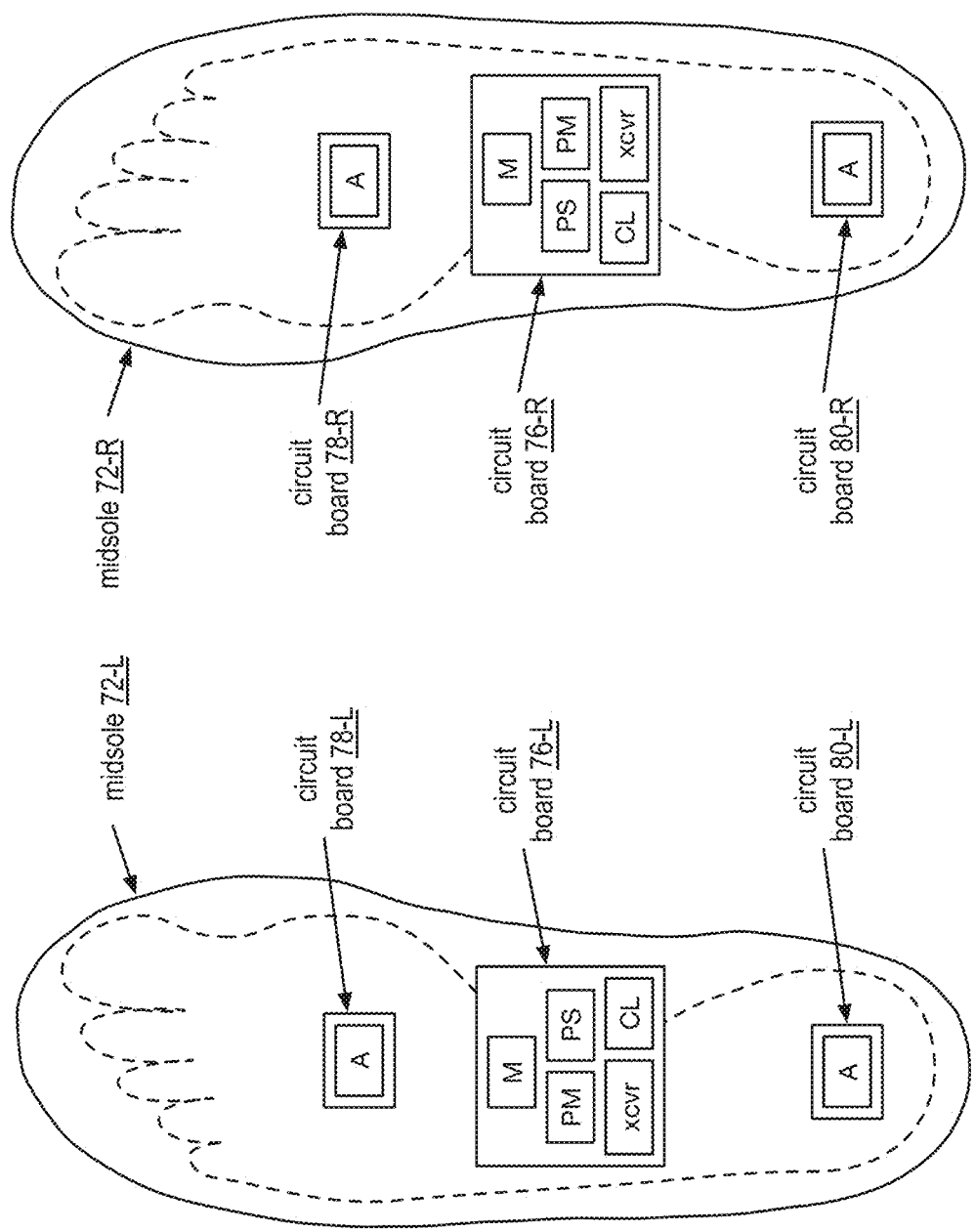

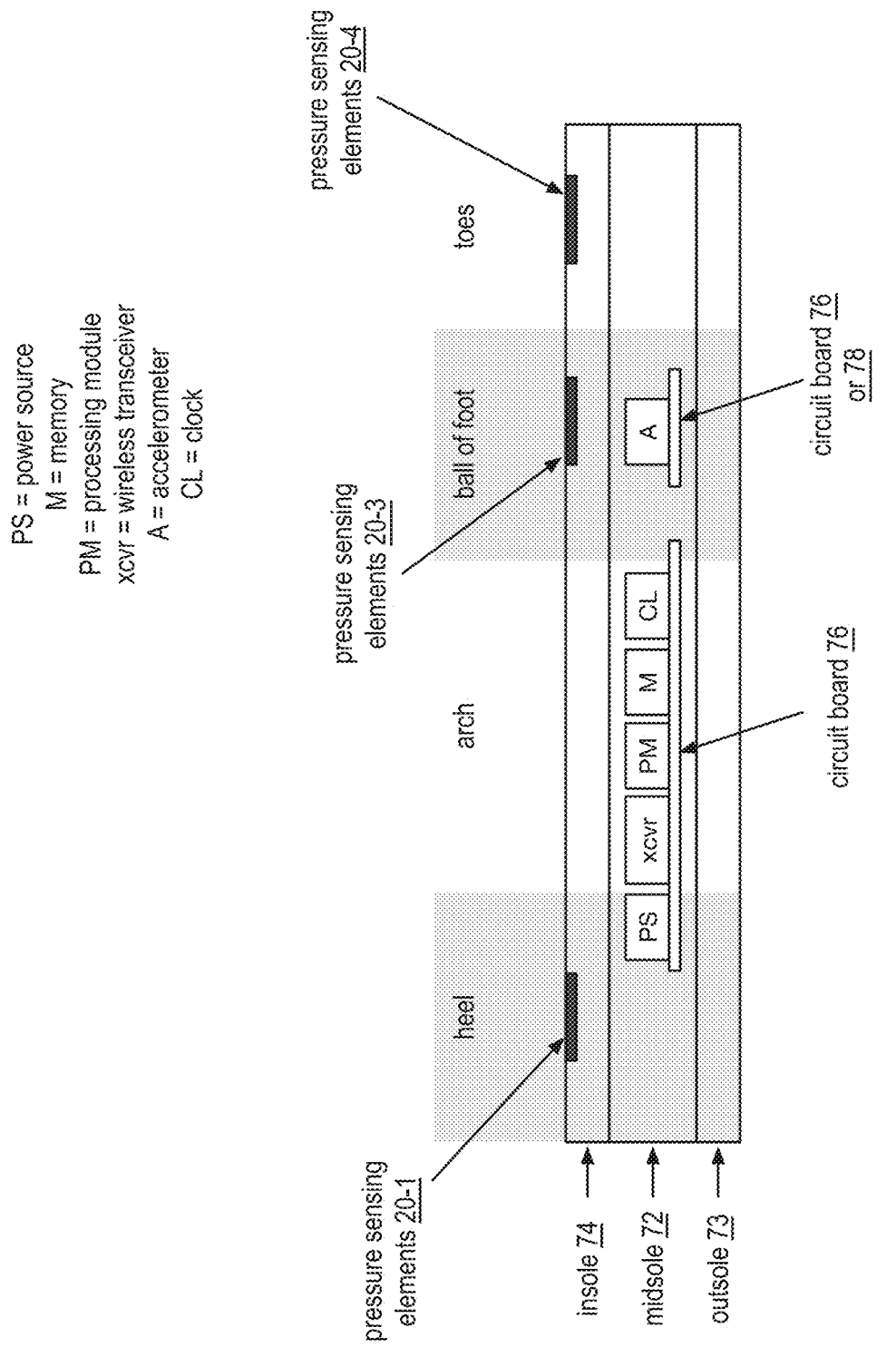

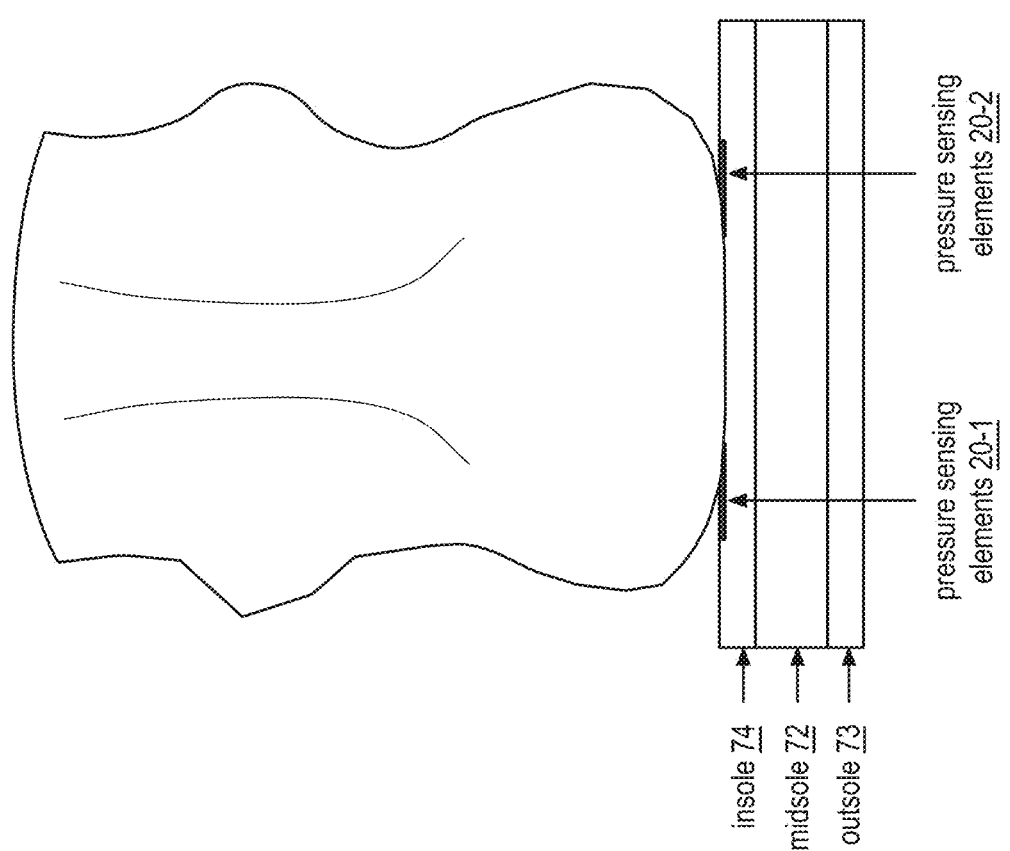

side view of shoe

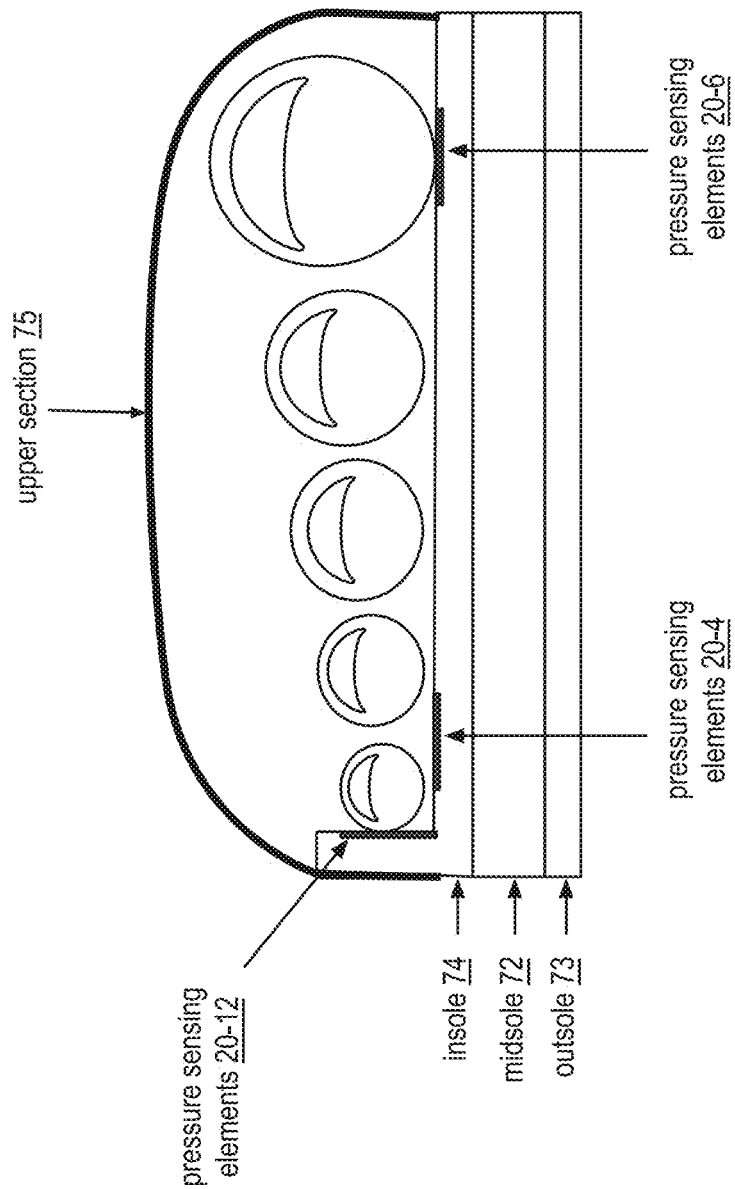

shoe sensor system 16-R & L shoe sensor system 16-R & L

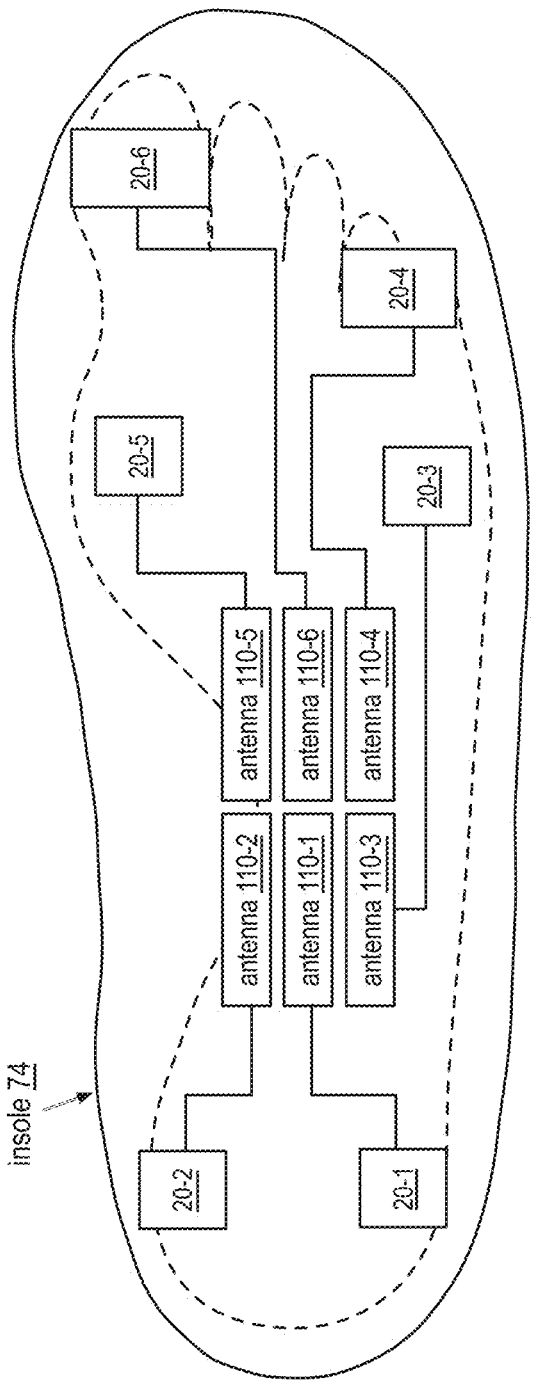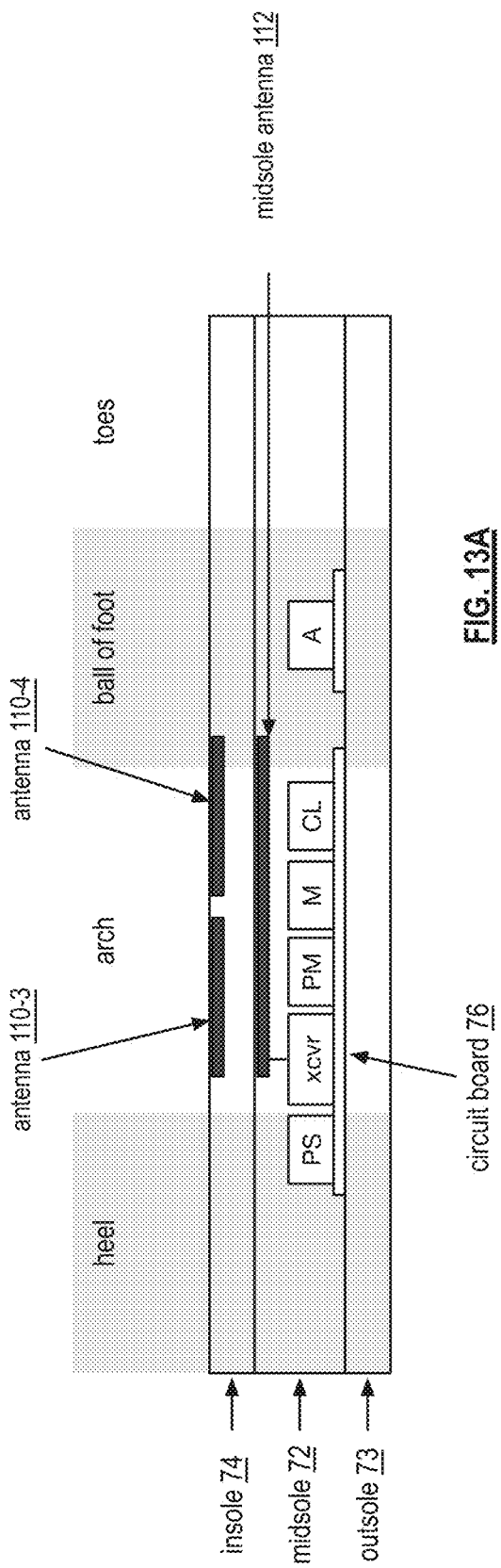

WIRELESS IN-SHOE PHYSICAL ACTIVITY MONITORING

CROSS REFERENCE TO RELATED PATENTS

The present U.S. Utility Patent application claims priority pursuant to 35 U.S.C. § 120 as a continuation of U.S. Utility application Ser. No. 15/680,027, entitled "WIRELESS IN-SHOE PHYSICAL ACTIVITY MONITORING", filed Aug. 17, 2017, issuing on Sep. 28, 2021 as U.S. Pat. No. 11,129,547, which claims priority pursuant to 35 U.S.C. § 119(e) to U.S. Provisional Application No. 62/376,555, entitled "In-Shoe Ground Reactive Force Measuring System", filed Aug. 18, 2016, all of which are hereby incorporated herein by reference in their entirety and made part of the present U.S. Utility Patent application for all purposes.

STATEMENT REGARDING FEDERALLY SPONSORED RESEARCH OR DEVELOPMENT

NOT APPLICABLE

INCORPORATION-BY-REFERENCE OF MATERIAL SUBMITTED ON A COMPACT DISC

NOT APPLICABLE

BACKGROUND OF THE INVENTION

Technical Field of the Invention

This invention relates generally to wearable technology and more particularly to a wireless in-shoe physical activity monitoring system.

Description of Related Art

Technology is being used more and more to monitor a person's physical activities, rest patterns, diet, and vital signs. Some of this technology is wearable. For example, there are wrist wearable devices to monitor the number of steps a person takes in a day, the approximate distance traveled, heart rate, and/or sleep patterns. As another example, there are chest straps that communicate wirelessly with a module for monitoring heart rate.

As yet another example, there are shoe insert systems to monitor forces of the foot during walking. One such system includes a flexible circuit board insert that includes a resistive sensor grid that is hard wired to a module that straps to the ankle. The two ankle modules are then hard wired to another module that straps to the waist. The waist module collects the data and communicates it to a computer via a wired or wireless connection.

Another technology for monitoring foot force is to use a pressure sensitive mat on which a person stands to perform a physical activity (e.g., golf). The mat detects variations in foot forces during the execution of the physical activity, which is then analyzed to evaluate the performance of the physical activity.

BRIEF DESCRIPTION OF THE SEVERAL VIEWS OF THE DRAWING(S)

FIG. 1 is a top view diagram of a pair of shoes in accordance with the present invention;

FIGS. 2A and 2B are side view diagrams of an embodiment of pair of shoes that each include a shoe sensor system in accordance with the present invention;

FIGS. 2C and 2D are side view diagrams of another embodiment of pair of shoes that each include a shoe sensor system in accordance with the present invention;

FIG. 4 is a schematic block diagram of an embodiment of a shoe sensor system in accordance with the present invention;

FIG. 5 is a logic diagram of an example of a method executed by a processing module in accordance with the present invention;

FIGS. 6A-6D are examples of timing and data diagrams of a shoe sensor system in accordance with the present invention;

FIGS. 7A and 7B are top view diagrams of an example of positioning pressure sensing elements within a pair of shoes in accordance with the present invention;

FIGS. 7C and 7D are top view diagrams of another example of positioning pressure sensing elements within a pair of shoes in accordance with the present invention;

FIGS. 8A and 8B are top view diagrams of an example of the pressure sensing elements positioned with respect to an insole of a right shoe and the control circuit positioned with respect to a midsole of a right shoe in accordance with the present invention;

FIGS. 8C and 8D are top view diagrams of an example of the pressure sensing elements positioned with respect to an insole of a left shoe and the control circuit positioned with respect to a midsole of a left shoe in accordance with the present invention;

FIG. 8E is a top view diagram of another example of the control circuit and accelerometer positioned with respect to a midsole of a left shoe in accordance with the present invention;

FIG. 8F is a top view diagram of another example of the control circuit and accelerometer positioned with respect to a midsole of a right shoe in accordance with the present invention;

FIG. 8G is a top view diagram of another example of the control circuit and two accelerometers positioned with respect to a midsole of a left shoe in accordance with the present invention;

FIG. 8H is a top view diagram of another example of the control circuit and two accelerometers positioned with respect to a midsole of a right shoe in accordance with the present invention;

FIG. 8I is a side view diagram of another example of the pressure sensing elements positioned with respect to an insole of a shoe and the control circuit and accelerometer positioned with respect to a midsole of the shoe in accordance with the present invention;

FIG. 8K is a rear-view diagram of another example of the pressure sensing elements positioned with respect to an insole of a shoe in accordance with the present invention;

FIG. 8M is a front view diagram of another example of the pressure sensing elements positioned with respect to an insole of a shoe in accordance with the present invention;

FIG. 12 is a top view diagram of an example of the pressure sensing elements and corresponding antennas positioned with respect to an insole of a shoe in accordance with the present invention;

FIG. 13A is a side view diagram of an example of the antennas positioned with respect to an insole of a shoe and the control circuit, with an antenna, and accelerometer positioned with respect to a midsole of the shoe in accordance with the present invention;

DETAILED DESCRIPTION OF THE INVENTION

Figure 3:
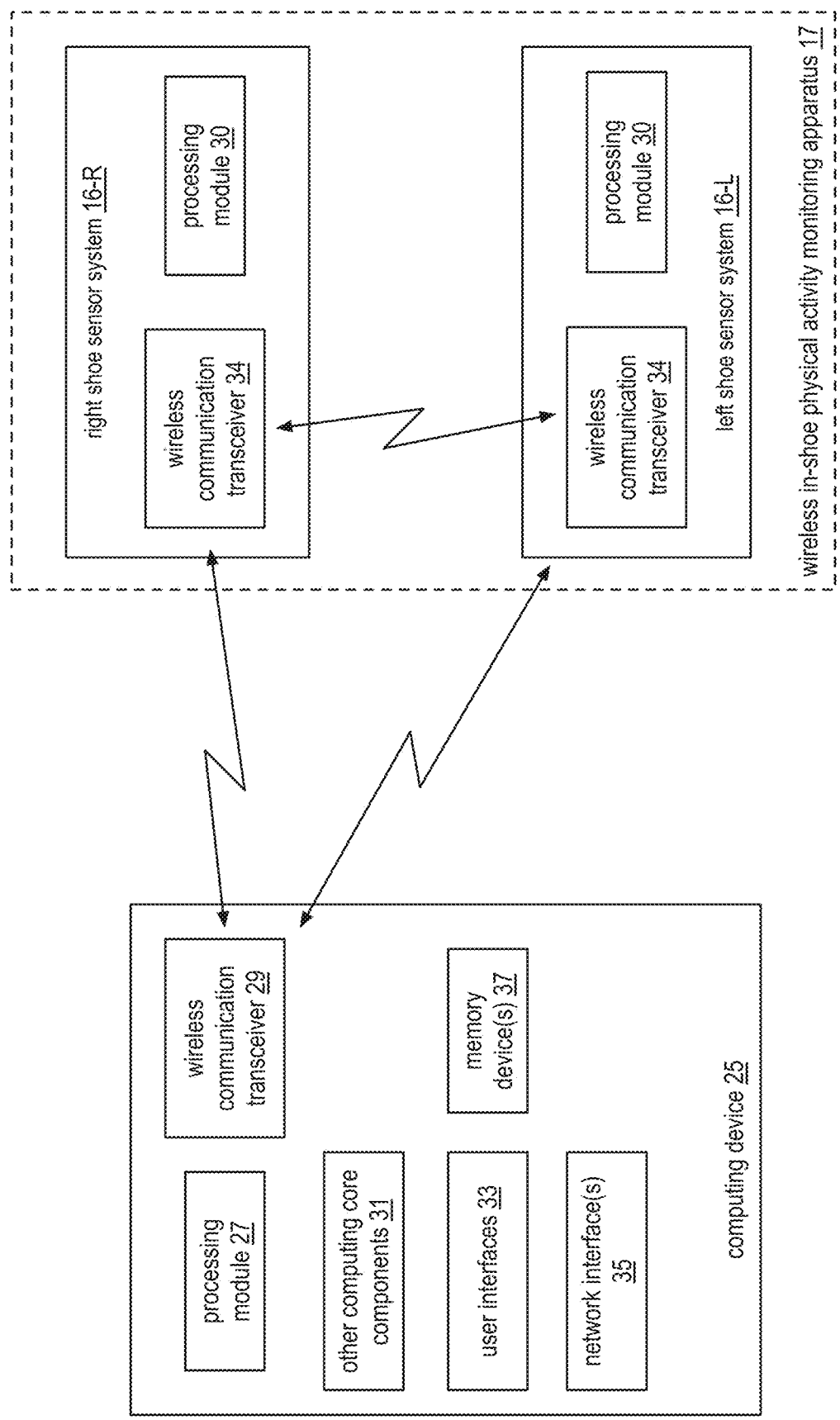
FIG. 3 is a schematic block diagram of an embodiment of a wireless in-shoe physical activity monitoring apparatus and a computing device in accordance with the present invention.

FIG. 1 is a top view diagram of a pair of shoes 10 that includes a right shoe 12 and a left shoe 14. The shoes 10 may be sports specific athletic shoes (e.g., baseball, basketball, golf, tennis, track & field, running, etc.), walking shoes, dress shoes, work boots, hiking shoes or boots, etc.

FIGS. 2A and 2B are side view diagrams of an embodiment of a left shoe and a right shoe; each of which includes a shoe sensor system 16-L (left) and 16-R (right). In an embodiment, the shoe sensor system is located on or within the insole and/or midsole of the shoe and functions to capture a multitude of information. For example, the shoe sensor system 16 gathers data of a user's movements (e.g., running, jumping, walking, hitting a golf ball, hitting a baseball, pitching a baseball, playing basketball, etc.) for subsequent analysis (e.g., determine ground reaction forces, weight distribution, stride length, time duration of activity, imbalances in weight distribution, imbalances in stride length, elevation ascended, distance traveled, elevation descended, foot rotation, form, gait, etc.). The data includes ground reaction forces from a plurality of pressure sensing element and three-dimensional foot positioning data from one or more accelerometers and/or gyroscopes. In addition, the data is further analyzed to determine whether performance of a physical activity is being done optimally (e.g., with proper form, with consistency, without undue stress on the body, level of fatigue, etc.). When the physical activity is being performed less than optimally, the corrective measures are determined based on the cause, or causes, of the less than optimal performance.

With the shoe sensor system 16 within each shoe 12 and 14, the shoes 10 can be used in game to collect in-game data. For example, the shoes 10 are baseball spikes worn by a pitcher. Each shoe gathers foot force data from the plurality of pressure sensing elements and gathers three-dimensional (3D) foot data (e.g., x-y-z data from an accelerometer). The foot force data and the 3D foot data are sent via a wireless link (e.g., a Bluetooth link) to a computing device that is off the field of play. The computing device processes the data to determine ground reaction forces of various locations on each foot, weight distribution, balance, stride length, etc., which can be used to determine the pitcher's level of fatigue, efficiency, etc.

FIGS. 2C and 2D are side view diagrams of another embodiment of a left shoe and a right shoe; each of which includes a dongle 15, pressure sensing elements 20, and one or more accelerometers 22. The dongle 15 includes a control circuit that communicates with the pressure sensing elements 20 and the accelerometer(s) 22 and also wirelessly communications the collected data to a computing device. The dongle 15 is a relatively small device (e.g., less than 1 inch×1 inch×½ inch) that includes an exterior housing for containing a control circuit board. The dongle 15 may be clipped to the heel or lateral side of the shoe as shown in FIG. 2C or clipped or laced into the laces of the shoe as shown in FIG. 2D. Note that the dongle 15 may be attached to other locations on each shoe and in different locations from shoe to shoe.

FIG. 3 is a schematic block diagram of an embodiment of a wireless in-shoe physical activity monitoring apparatus 17 and a computing device 25. The wireless in-shoe physical activity monitoring apparatus 17 includes a right shoe sensor system 16-R and a left shoe sensor system 16-L. As will be described in greater detail with reference to FIG. 4 and other figures, each shoe sensor system 16 includes pressure sensor elements 20-1 through 20-x, an accelerometer 22, and control circuit 24. The control circuit 24 includes a power source circuit 24, a clock circuit 28, a processing module 30, memory 32, a wireless communication transceiver 34, and a sampling signal generator 35. The processing module 30 and the wireless communication transceiver 34 are shown in this Figure.

The computing device 25 is any electronic device that can communicate data, process data, and/or store data. As an example, the computing device 25 is a portable computing device and/or a fixed computing device. A portable computing device may be a social networking device, a gaming device, a cell phone, a smart phone, a personal digital assistant, a digital music player, a digital video player, a laptop computer, a handheld computer, a tablet, a video game controller, and/or any other portable device that includes a computing core. A fixed computing device may be a personal computer (PC), a computer server, a cable set-top box, a satellite receiver, a television set, a printer, a fax machine, home entertainment equipment, a video game console, and/or any type of home or office computing equipment that includes a computing core.

The computing device 25 includes a computing core, user interfaces 33, network interface(s) 35, a wireless communication transceiver 29, and memory device(s) 37. The user interfaces 33 includes one or more input devices (e.g., keypad, keyboard, touchscreen, voice to text, etc.), one or more audio output devices (e.g., speaker(s), headphone jack, etc.), and/or one or more visual output devices (e.g., video graphics display, touchscreen, etc.). The network interface(s) 35 includes one or more networking devices (e.g., a wireless local area network (WLAN) device, a wired LAN device, a wireless wide area network (WWAN) device (e.g., a cellular telephone transceiver, a wireless data network transceiver, etc.), and/or a wired WAN device). The memory device(s) 37 includes one or more of a flash memory device, one or more hard drives, one or more solid state (SS) memory devices 96, and/or cloud memory.

The computing core includes a processing module 27 and other computing core components 31. The other computing core components include a video graphics processing unit 60, a memory controller, main memory (e.g., RAM), one or more input/output (I/O) device interface module, an input/output (I/O) interface, an input/output (I/O) controller, a peripheral interface, one or more USB interface modules, one or more network interface modules, one or more memory interface modules, and/or one or more peripheral device interface modules. Each of the interface modules includes a combination of hardware (e.g., connectors, wiring, etc.) and operational instructions stored on memory (e.g., driver software) that is executed by the processing module and/or a processing circuit within the interface module. Each of the interface modules couples to one or more components of the computing device 25. For example, one of the IO device interface modules couples to an audio output device. As another example, one of the memory interface modules couples to flash memory and another one of the memory interface modules couples to cloud memory (e.g., an on-line storage system and/or on-line backup system).

The wireless communication transceiver 29 of the computing device 25 and the wireless communication transceivers 34 of the shoe sensor systems 16 are of a like transceiver type (e.g., Bluetooth, WLAN, ZigBee, etc.). The transceivers 34 communicate directly with transceiver 29 to share gathered data by the respective shoe sensor systems 16 and/or to receiving instructions from the computing device 25. In addition to or in the alternative, the transceivers 34 communicate gathered data between them and one of the transceivers 34 communicates the collective data to the transceiver 29.

The computing device 25 processes the data to produce a variety of resultants. For example, the computing devices processes data from the shoe sensor systems 16 to determine a distance traveled during a time period, which may be an entire time duration of a physical activity, time intervals (e.g., 5 minute intervals, etc. As another example, the computing devices processes data from the shoe sensor systems 16 to determine stride length data (e.g., maximum stride length, minimum stride length, average stride length, stride length for a time interval, stride length of a distance segment, etc.).

As another example, the computing devices processes data from the shoe sensor systems 16 to determine a time duration of the physical activity (e.g., walking, running, playing a sport, executing an athletic movement, lifting weights, cross-fit training, etc.). As another example, the computing devices processes data from the shoe sensor systems 16 to determine a fatigue indication (e.g., shortening of stride, pace slowing, change in foot forces, etc.). As another example, the computing devices processes data from the shoe sensor systems 16 to determine injury prevention indicators (e.g., recognize change in data, where change is likely caused by fatigue, cramping, muscle strain, etc.).

As another example, the computing devices processes data from the shoe sensor systems 16 to determine elevation tracking for the time period (e.g., steps climbed, elevation changes in a run, a walk, or a hike, etc.). As another example, the computing devices processes data from the shoe sensor systems 16 to determine running optimization (e.g., proper foot positioning & weight distribution when running, balanced strides, stride length training, increase ground reaction force, reduce foot to ground contact time, etc.). As another example, the computing devices processes data from the shoe sensor systems 16 to determine rotational sport optimization (e.g., weight distribution, ground reaction forces, balance, linear movement, rotational movement, etc.).

The computing device 25 further includes operational instructions to generate a graphical user interface for the recording, gathering, and/or processing of the data of the shoe sensor systems 16. For example, the graphical user interface (GUI) displays information regarding the processing of the data. As a specific example, the GUI displays information about a run, such as time duration, stride length information, foot force information, gait information, etc. As another example, the GUI displays, in real time, foot forces and foot positioning during a physical activity to determine one or more of proper form, fatigue analysis, injury predictive analysis, weight distribution, and corrective measures of form.

FIG. 4 is a schematic block diagram of an embodiment of a shoe sensor system 16 that includes pressure sensor elements 20-1 through 20-x, an accelerometer 22, and control circuit 24. The control circuit 24 includes a power source circuit 24, a clock circuit 28, a processing module 30, memory 32, a wireless communication transceiver 34, and a sampling signal generator 35. The pressure sensing elements 20 includes one more of a resistive pressure sensor, a piezoelectric pressure sensor, a capacitive pressure sensor, and an inductive pressure sensor and are distributed in a pattern having a shape corresponding to an outline a human foot as will be discussed with reference to one or more subsequent figures. Note that the pressure sensing elements may be circuits as described in greater detail with reference to FIGS. 14-16, may be individual sensors as described in greater detail with reference to FIGS. 17A-17B, and/or a combination thereof.

The pressure sensing elements 20 are coupled to the processing module 30 via sensor communication links 36. As an example, a sensor communication link 36 includes a wired communication link such as a metal trace on a printed circuit board, a wire, a dedicated data bus, or a shared data bus. In another example, a sensor communication link 36 includes a wired communication path that is in accordance with a wired communication protocol. The wired communication protocol includes RS-422, Inter-Integrated Circuit bus (I2C), serial peripheral interface (SPI), microwire, 1-wire, etc.

As another example, a sensor communication link 36 includes an inductive communication path in accordance with a near field communication (NFC) communication protocol. As yet another example, a sensor communication link 36 includes a light communication base in accordance with a light-based communication protocol (e.g., Infrared, fiber optics, etc.). As a further example, a sensor communication link 36 includes a radio frequency (RF) communication path in accordance with a wireless communication protocol (e.g., 60 GHz, Bluetooth, WLAN, ZigBee, etc.).

The accelerometer 22 is coupled to the processing module 30 via an accelerometer communication link 38. The accelerometer communication link 38 includes a wired communication link, a wired communication path in accordance with a wired communication protocol, an inductive communication path in accordance with a near field communication (NFC) communication protocol, a light communication base in accordance with a light-based communication protocol, and/or a radio frequency (RF) communication path in accordance with a wireless communication protocol.

In an example of operation, the power source circuit 26 generates one or more supply voltages 40 that powers the other devices of the control circuit 24. In an embodiment, the accelerometer 22 is on a common printed circuit board with the control circuit 24 and is powered by one of the supply voltages. In another embodiment, the accelerometer 22 is on a separate printed circuit board from the control circuit 24 and is powered by a power supply on the separate printed circuit board. In yet another embodiment, the accelerometer 22 is on a separate printed circuit board from the control circuit 24, but receives one of the supply voltages 40 via the accelerometer communication link 38.

In an embodiment, each of the pressure sensing elements are active device and receive one of the supply voltages 40 via their respective sensor communication link 36. In another embodiment, each of the pressure sensing elements are active device and receive one of the supply voltages 40 are passive devices and include a power harvesting circuit to generate a local supply voltage. In yet another embodiment, each of the pressure sensing elements are active device on a flexible circuit board, which includes a local power supply to generate the local supply voltage.

In an example embodiment, the power source circuit 26 includes a battery-powered power supply. The power supply is a DC-to-DC converter and/or a linear regulator. In another example, the power source circuit 26 includes the battery-powered power supply and a wired battery charger. In this example, the battery charger is connected via a wire to the battery of the battery-powered power supply for charging. In a specific example, the shoe includes a connector or plug that is accessible from the heel of the shoe. The battery charger is an external device that plugs into the connector. In yet another example, the power source circuit 26 includes the battery-powered power supply and a wireless battery charger. In a further example, the power source circuit 26 includes a radio frequency (RF) power harvesting circuit; an example of which will be described with reference to one or more subsequent drawings.

Continuing with the example of operation, the clock circuit 28 generates a clock signal 42. The clock signal 42 may be a sinusoidal signal, a pulse pattern, a square wave signal, or other type of signal having a clock rate (e.g., 10 KHz to 10 GHz). The sampling signal generator 35 generates one or more sampling signals 44 from the clock signal 42. For example, the sampling signal generator 35 is a buffer such that the sampling signal 44 is a buffered version of the clock signal 42. As another example, the sampling signal generator 35 is a phase locked loop (PLL) that multiples the rate of the clock signal 42 such that the sampling signal 44 has a rate that is "x" times the rate of the clock signal 42, where "x" is greater than 1.

As yet another example, the sampling signal generator 35 is a that divides the rate of the clock signal 42 such that the sampling signal 44 has a rate that is "y" times the rate of the clock signal 42, where "y" is greater than 1. As a further example, the sampling signal generator 35 includes a digital delay line to create one or more sampling signals 44 from the clock signal. As a still further example, the sampling signal generator 35 includes a PLL and a digital delay line. Examples of generating the sampling signal 44 will be described with reference to FIGS. 6A-6D.

Continuing with the example of operation, the processing module 30 samples, in accordance with the sampling signal 44, data (e.g., a digital value or analog voltage representing a pressure being sensed) from the pressure sensing element to produce foot force data 46. The processing module 30 also samples, in accordance with the sampling signal 44, data (e.g., x-y-z coordinate data or polar coordinate data) from the first accelerometer to produce three-dimensional (3D) foot data 48. The processing module 30 may store the foot force data 46 and the 3D data in memory 32 and/or provide it to the wireless communication transceiver 34 for transmission to the computing device.

In an embodiment, the control circuit is on a printed circuit board (PCB) that is positioned within a hole of the midsole. The PCB may be secured into the hole with an adhesive, with an encasing material, etc. The PCB is a single layer printed circuit board (PCB), a multiple layer PCB, a rigid PCB, a flexible PCB, a high frequency PCB, and/or an aluminum-backed PCB.

In another embodiment, the control circuit is on a printed circuit board (PCB) that is positioned within the dongle 15. The accelerometer 22 may be on the PCB with the control circuit and thus positioned within the hole of the midsole or within the dongle 15. In yet another embodiment, the accelerometer 22 is on a separate PCB from that of the control circuit 24. In one permeation of this embodiment, the accelerometer 22 is positioned within a second hole of the midsole regardless of whether the control circuit PCB is within the hole of the midsole or in the dongle.

FIG. 5 is a logic diagram of an example of a method executed by a processing module that may be implemented as operational instructions stored on a computer readable memory. The method begins at step 60 where the processing module (e.g., processing module 30 of the shoe sensor system 16 and/or processing module 27 of computing device 25) obtains foot force data. The foot force data created by sampling, in accordance with a sampling signal, data from the pressure sensing elements of a shoe sensor system.

On a per sample basis, the foot force data includes, from at least some of the pressure sensing elements, a pressure sensor indicator (e.g., an identifier of the particular pressure sensing element providing the data) and one or more of a pressure sensed value, a representation of the sensed pressure level, and a pressure measurement. As an example, a pressure sensing element generates a resistance from a resistive pressure sensor, a capacitance from a capacitance pressure sensor, an inductance from an inductor pressure sensor, or a frequency from a piezoelectric pressure sensor in response to an applied pressure. The resistance, the capacitance, the inductance, or the frequency is provided as the pressure sensed value (i.e., raw data of a pressure measurement).

The representation of the sensed pressure level is a digital value from a range of digital values or an analog voltage from a range of analog voltages that based on the resistance, the capacitance, the inductance, or the frequency generated by the pressure sensing element. For example, a five-bit digital value includes a range from 0-31 (decimal), where 0 corresponds to no pressure and 31 corresponds to maximum pressure of the pressure sensor. The representation of the sensed pressure level is not a pressure measurement, but a value in a range of values. The pressure measurement converts the representation of the sensed pressure level into an actual pressure measurement. As such, over a plurality of samples, the foot force data 46 includes, from each of at least some of the pressure sensing elements, the pressure sensor indicator and one or more of a plurality of pressure sensed values, a plurality of representations of sensed pressure levels, and a plurality of pressure measurements.

As an example of one sampling interval, assume that a resistive pressure sensor of the pressure sensing element has a maximum pressure of 200 pounds. For one sample, the resistive pressure sensor generates a resistance of 1,500 Ohms, where the resistance ranges from 100,000 Ohms with no pressure to 500 Ohms with 200 pounds of pressure. The 1,500 Ohms is converted to a digital value of 11000 (e.g., 24 in a digital scale of 0 to 31). The digital value is then converted in a pressure measurement of 150 pounds via a look up table or other type of calculation.

The method continues at step 62 where the processing module obtains three-dimensional (3D) foot data. The 3D foot data is created by sampling, in accordance with the sampling signal, data from a first accelerometer of the shoe sensor system. On a per sample basis, the 3D foot data includes an accelerometer identifier (e.g., an ID of the first accelerometer) and one of an x-y-z coordinate value, a representation of an x-y-z coordinate, and an x-y-z coordinate. The 3D foot data may further include an x-y-z origin coordinate. As such, over a plurality of samples, the 3D foot force data includes the accelerometer identifier and one of a plurality of x-y-z coordinate values, a plurality of representations of x-y-z coordinates, and a plurality of x-y-z coordinates.

As an example, the x-y-z origin coordinate is the origin of a reference Cartesian coordinate system corresponding to one of the shoes. Typically, when the shoe sensor is initialized to monitor a physical activity, an origin will be established based on a current location of the shoe for the reference Cartesian coordinate system. An x-y-z coordinate value is the raw data generated by the accelerometer for a given sample interval; the raw data includes a current x-axis acceleration, a current y-axis acceleration, and a current z-axis acceleration. A representation of the coordinate value is conversion of the raw accelerometer data into a x-y-z distance data based on the equation, for the x-axis) $x = v_0 t + \frac{1}{2} a t^2$, where x is the distance in the x-axis direction, t is the time interval, $v_0$ is the initial velocity, and a is the acceleration in the x-axis. From the x distance, y distance, and z distance and the x-y-z coordinate of the previous sample (or the origin coordinate if this is the first sample interval) the current coordinate is determined, which corresponds to the x-y-z coordinate.

With respect to steps 60 and 62, in one embodiment, the processing module of the shoe sensor system obtains the foot force data by receiving it from the plurality of pressure sensing elements and obtains the three-dimensional foot data by receiving it from the first accelerometer. In another embodiment, the processing module of a computing device obtains the foot force data includes by receiving it from a transmitter of the wireless communication transceiver and obtains the three-dimensional foot data by receiving it from the transmitter.

The method continues at step 64 where the processing module correlates the foot force data and the three-dimensional foot data in accordance with the sampling signal to produce correlated foot data. In an example embodiment, the processing module of the shoe sensing system correlates the foot force data and the foot three-dimensional data to produce correlated foot data and the wireless communication transceiver transmits the correlated foot data within the outbound RF signals to the computing device.

The method continues at step 66 where the processing module processing the correlated foot data to determine physical activity data. The physical activity data includes distance traveled during a time period (as will be discussed in greater detail with reference to FIG. 21), stride length data (as will be discussed in greater detail with reference to FIGS. 22A and 22B), time duration (as will be discussed in greater detail with reference to FIG. 23), fatigue indication (as will be discussed in greater detail with reference to FIG. 24), injury prevention indicators (as will be discussed in greater detail with reference to FIG. 25), elevation tracking for the time period (as will be discussed in greater detail with reference to FIGS. 26A and 26B), running optimization (as will be discussed in greater detail with reference to FIG. 27), and rotational sport optimization (as will be discussed in greater detail with reference to FIG. 28).

In furtherance of the processing, the processing module adjusts the processing of the correlated foot data based on known nature of a physical activity. The known nature of the physical activity includes predicable motions of body parts (e.g., how the feet, legs, hands, arms, torso, and head move when running or walking; how the body is supposed to move when hitting a golf ball; how the body is supposed to move when throwing a ball or hitting a ball with a racket or a bat; etc.). The known nature of the physical activity may further be enhanced to account for age of the person engaging in the physical activity, the skill level of the person, and/or other personal characteristics that may affect performance of the physical activity (e.g., injuries, flexibility, height, weight, etc.).

As an example of adjusting of the processing, the processing module adjusts the rate of the sampling signal. For instance, when the physical activity is walking, less data points are needed than when the person is sprinting or jogging. As another example, the processing module using physical activity general movement data to enhance correlation of the foot force data and the foot three-dimensional data. As yet another example, the processing module using the physical activity general movement data to further determine the one or more of: the distance traveled during a time period, the stride length data, the time duration, the fatigue indication, the injury prevention indicators, the elevation tracking for the time period, the running optimization, and the rotational sport optimization.

As a still further example, the processing module using previous data of a wearer to determine the one or more of: the distance traveled during a time period, the stride length data, the time duration, the fatigue indication, the injury prevention indicators, the elevation tracking for the time period, the running optimization, and the rotational sport optimization. For example, if the person has a history of averaging 6 mph when jogging with an average stride length of 3 feet, then the shoe sensor system can be tuned to expect a pace of 6 mph and a stride length of about 3 feet, which will help improve accuracy of detecting foot strikes, etc.

FIG. 6A is an example of timing and data diagram of a shoe sensor system 10.

The timing includes the sampling signal 44 that has a square wave 50% duty cycle clock and a sampling rate (e.g., 500 Hz to 50 KHz). The sampling clock 44 may have an alternative waveform (e.g., sinusoidal, a rectified sinusoidal signal, etc.) and may have an alternate duty cycle (e.g., 10% to 90%). With each sampling interval (e.g., sample 1, 2, 3, 4, etc.), each of the pressure sensing elements 20 and the accelerometer 22 provide data. The data may be 4-32 bits per element 20 and from the accelerometer 22 per sample interval.

The pressure sensing elements 20 provide the foot force data 46 and the accelerometer provides the 3D foot data 48. For each sample interval (e.g., sample 1, 2, 3, 4, etc.), the processing module 30 of the shoe sensor system correlates the foot force data 46 and the 3D foot data 48 to produce the correlated data 52. The correlation of the data 46 and 48 may be an aggregation of the data on a per sampling interval. For example, a data packet for sample 1 includes the foot force data 46 sampled from each of the pressure sensing elements taking during sampling interval 1, an ID for each of the pressure sensing element tied to their respective data, the 3D foot data from the accelerometer sampled during sampling interval 1, and an ID for the accelerometer tied to its data.

As another example of correlation, the processing module identifies a first foot force data point of the foot force data (i.e., the data from each of the pressure sensing elements sampled during the first sampling interval) and a first three-dimensional foot data point of the three-dimensional foot data (i.e., the data from the accelerometer sampled during the first sampling interval). The processing module then links the first foot force data point with the first three-dimensional foot data point for the first sampling interval. The linking includes aggregation, aggregation and encryption, aggregation and scrambling, forward error correction such as Reed Solomon, and/or common packet identifiers. For example, the data from each of the pressure sensing elements 20 and the accelerometer 22 is transmitted in its own data packet that includes the data, an ID of the device associated with the data, and a sampling interval indicator (e.g., a sampling interval number, a clock count, a timestamp, etc.). The processing module links the foot force data points and the 3D foot data for each of the other sampling intervals in a similar manner.

Figure 6B:
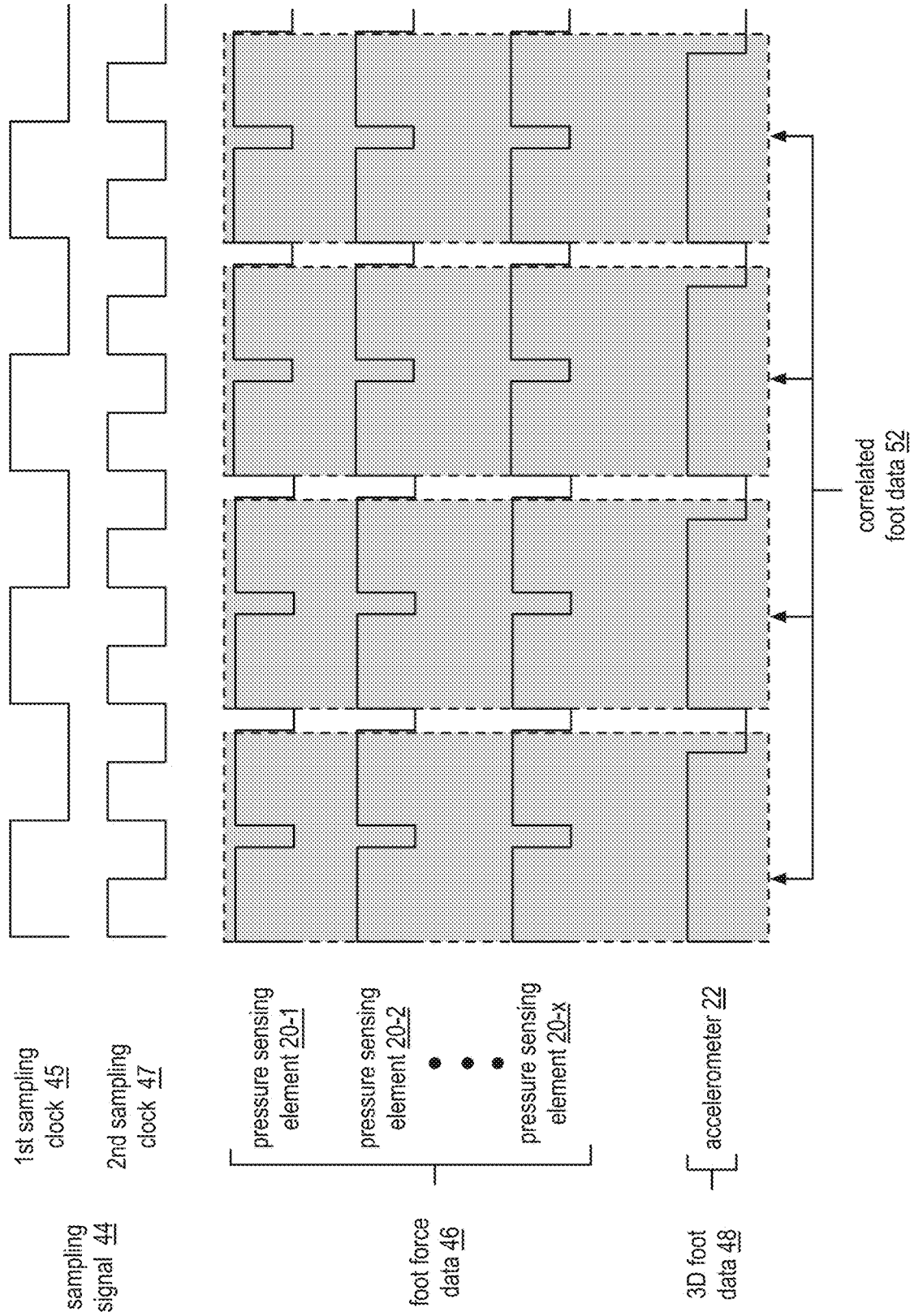

FIG. 6B is another example of timing and data diagram of a shoe sensor system 10. The timing includes a first sampling clock 45 and a second sampling clock 47. In this example, the second sampling clock 47 has a rate that is approximately twice that of the first sampling clock 45. The sampling clocks 45 and 47 are synced. The first sampling clock 45 is used to sample the data from the accelerometer 22 and the second clock 47 is used to sample the data from the pressure sensing modules 20.

As such, each of the pressure sensing elements produce two data samples per one data sample of the accelerometer. The data is correlated based on the slower clock signal such that, for each sampling interval of the first sampling clock 45, the correlated data includes two data samples from each of the pressure sensing elements and one data sample from the accelerometer.

Figure 6C:
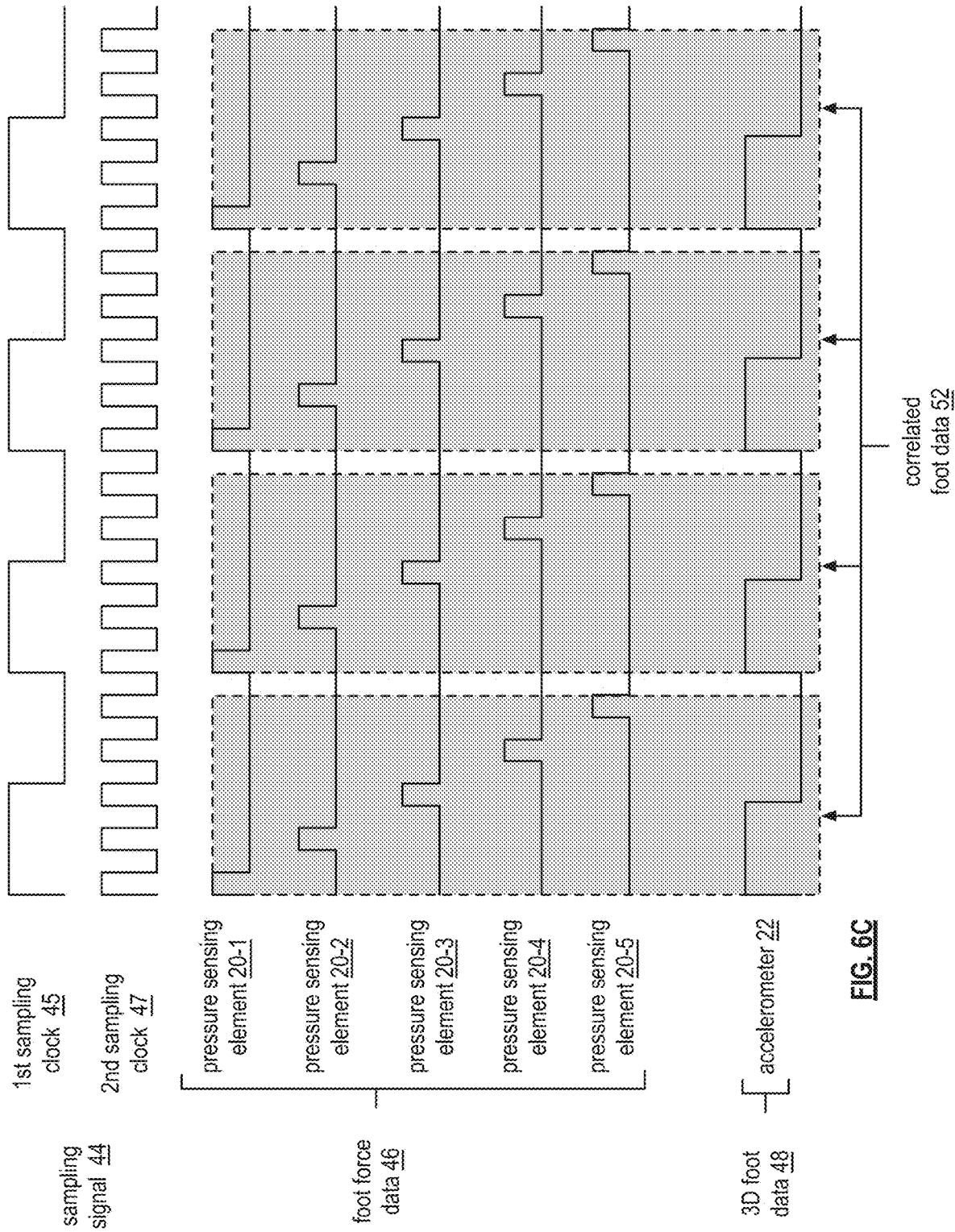

FIG. 6C is another example of timing and data diagram of a shoe sensor system 10. The timing includes a first sampling clock 45 and a second sampling clock 47. In this example, the second sampling clock 47 has a rate that is approximately five that of the first sampling clock 45. The sampling clocks 45 and 47 are synced. The first sampling clock 45 is used to sample the data from the accelerometer 22 and the second clock 47 is used to sample the data from the pressure sensing modules 20.

During the first sample interval of the first clock 45, there are five cycles of the second sampling clock 47. A first cycle of the second sampling clock 47 is used to sample the first pressure sensing element; a second cycle is used to sample a second pressure sensing element; a third cycle is used to sample a third pressure sensing element; a fourth cycle is used to sample a fourth pressure sensing element; and a fifth cycle is used to sample a fifth pressure sensing element. As such, each of the pressure sensing elements produce one data sample per one data sample of the accelerometer. The data is correlated based on the slower clock signal such that, for each sampling interval of the first sampling clock 45, the correlated data includes one data sample from each of the pressure sensing elements and one data sample from the accelerometer.

FIG. 6D is another example of timing and data diagram of a shoe sensor system 10. The timing includes a first sampling clock 45 and a plurality of second sampling clocks 47. In this example, each of the second sampling clock 47 has the same rate as the first sampling clock 45. The sampling clocks 45 and 47 are synced and the second sampling clocks are offset in time. The first sampling clock 45 is used to sample the data from the accelerometer 22 and the second clocks 47 are used to individually sample the data from the pressure sensing modules 20.

A first of the second sampling clocks 47 is used to sample the first pressure sensing element; a second of the second sampling clocks 47 is used to sample a second pressure sensing element; a third of the second sampling clocks 47 is used to sample a third pressure sensing element; a fourth of the second sampling clocks 47 is used to sample a fourth pressure sensing element; and a fifth of the second sampling clocks 47 is used to sample a fifth pressure sensing element. As such, each of the pressure sensing elements produce one data sample per one data sample of the accelerometer. The data is correlated based on the slower clock signal such that, for each sampling interval of the first sampling clock 45, the correlated data includes one data sample from each of the pressure sensing elements and one data sample from the accelerometer.

FIGS. 7A and 7B are top view diagrams of an example of positioning pressure sensing elements 20 within a pair of shoes. In this example, the pattern includes a first pressure sensing element 20-1 in a lateral heel position; a second pressure sensing element 20-2 in a medial heel position; a third pressure sensing element 20-3 in a lateral ball of foot position; a fourth pressure sensing element 20-4 in a lateral toe position; a fifth pressure sensing element 20-5 in a medial ball of foot position; and a sixth pressure sensing element 20-6 in a medial toe position.

In contrast to most foot force analysis systems, the present system includes pressure sensors in selected area, not across the entire surface area of the foot. Further, with the wireless features and modular design, it does not require any modules to be strapped on to the legs or the waist. Still further with a combination of pressures sensors and accelerometers, accurate physical activity data is obtained; not approximate data based on algorithms that predict physical activity from a few trigger points (e.g., arm movement for determine number of steps and to determine a distance traveled. Such approximations have a tolerance of about +/−10%. With the present system using measured physical activity data, the results will have a tolerance less than +/−1%.

FIGS. 7C and 7D are top view diagrams of another example of positioning pressure sensing elements 20 within a pair of shoes. This example is similar to the one of FIGS. 7A and 7B with the addition of two more pressure sensing elements 20 per shoe. Each shoe includes a seventh pressure sensing element in a mid-ball of foot position 20-7 and an eighth pressure sensing element 20-8 in a mid-toe position.

FIGS. 8A and 8B are top view diagrams of an example of the pressure sensing elements 20 positioned with respect to an insole 74-R of a right shoe and the control circuit board 70-R positioned with respect to a midsole 72-R of a right shoe. FIG. 8A illustrates the insole 74-R with six pressure sensing elements 20-1 through 20-6 positioned as shown in FIG. 7B. In an embodiment, each of the pressure sensing elements 20 is attached to the surface of the insole 74-R via an adhesive or other bonding agent. In another embodiment, each of the pressure sensing elements 20 is fabricate into the insole 74-R as the insole is manufactured. In another embodiment, the pressure sensing elements 20 are fabricated on a flexible printed circuit board that overlays and/or is adhered to the top surface of the insole 74-R.

FIG. 8B illustrates the midsole 72-R in which the control circuit board 70-R is mounted. The control circuit board 70-R includes the power source (PS), memory (M), a processing module (PM), a wireless transceiver (XCVR), an accelerometer (A), and a clock circuit (CL). In an embodiment, the control circuit board 70-R is positioned within a hole in the midsole 72-R, where the hole does not extend all the through the midsole and is just deep enough to engulf the control circuit board. Once the control circuit board 70-R is positioned in the hole, it is held in place by an adhesive, a bonding agent, an encasing material, etc.

Electrical coupling between the pressure sensing elements 20 and the control circuit board is accomplished in a variety of ways. As an example, the control circuit board includes an electrical connector that mates to a corresponding electrical connector coupled to the pressure sensing elements. The connectors are positioned in the insole and midsole respectively as to provide minimal interference with the fit and comfort of the shoe.

As another example, the control circuit board 70-R is coupled to the pressure sensing elements via RF signals. One or more examples of RF coupling will be described with reference to one or more of FIGS. 12-13C. As yet another example, the control circuit board 70-R is coupled to the pressure sensing elements via NFC coils. One or more examples of NFC coupling will be described with reference to one or more of FIGS. 18-19B.

FIGS. 8C and 8D are identical to FIGS. 8A and 8B, but FIGS. 8C and 8D are for the left shoe. As such, these Figures area top view diagrams of an example of the pressure sensing elements 20 positioned with respect to an insole 74-L of a left shoe and the control circuit board 70-L positioned with respect to a midsole 72-L of a left shoe.

FIG. 8E is similar to FIG. 8D with the accelerometer (A) being on a separate circuit board 78-L from the control circuit board 76-L. In an example, the accelerometer circuit board 78-L is coupled to the control circuit board 76-L via a wired connection. In another example, the accelerometer circuit board 78-L is coupled to the control circuit board 76-L via a wireless connection.

FIG. 8F is identical to FIG. 8E but it is for the right midsole 72-R and includes an accelerometer circuit board 78-R and a control circuit board 76-R.

FIG. 8G is similar to FIG. 8E with the addition of a second accelerometer on another circuit board 80-L. In an example, the accelerometer circuit board 80-L is coupled to the control circuit board 76-L via a wired connection. In another example, the accelerometer circuit board 80-L is coupled to the control circuit board 76-L via a wireless connection. Note that the second accelerometer is positioned within the pattern of the foot and is at a distance from the first accelerometer.

In an example of operation, the second accelerometer provides second x-y-z coordinates (i.e., second 3D foot data) at a sample rate of the sampling signal to the processing module (PM). Recall that the first accelerometer provides first x-y-z coordinates at the sample rate to the processing module (PM). The processing module correlates the foot force data, the three-dimensional foot data, and the second three-dimensional foot data in accordance with the sampling signal to produce the correlated foot data.

The processing module (e.g., of the circuit board and/or of the computing devices) processes the first and second x-y-z coordinates to produce foot orientation data. For example, for a given sampling interval, the first x-y-z coordinates are processed to determine a first location of the first accelerometer and the second x-y-z coordinates are processed to determine a second location of the second accelerometer. With the distance between the first and second accelerometers known, the orientation of the foot is determined.

Each of the accelerometer boards 76-L and 78-L require power and a clock signal or sampling signal. In an embodiment, each board 76-L and 78-L includes its own power source circuit and clock circuit to generate the sampling signal. In another embodiment, each board 76-L and 78-L receives a power supply and a clock signal or sampling signal from the control circuit board 70-L. In yet another embodiment, each board 76-L and 78-L includes its own power source circuit and receives the clock or sampling signal from the control circuit board 70-L.

FIG. 8H is identical to FIG. 8G but it is for the right midsole 72-R and includes accelerometer circuit board 78-R, accelerometer circuit board 80-R, and a control circuit board 76-R.

FIG. 8I is a side view diagram of another example of the pressure sensing elements 20 positioned with respect to an insole 74 of a shoe (e.g., left or right foot) and the control circuit board 76 and accelerometer (A) positioned with respect to a midsole 74 of the shoe. The shoe is further shown to include an outsole 73.

Each of the pressure sensing elements 20-1, 20-3, and 20-4 and the others not shown are positioned at or on the surface of the insole 74. Pressure sensing element 20-1 (and 20-2 not shown) are positioned in the heel section of the shoe; pressure sensing element 20-3 (and 20-5 not shown) are positioned in the ball of foot section of the shoe; pressure sensing element 20-4 (and 20-6 not shown) are positioned in the toe section of the shoe. The accelerometer (A) may be on the same PCB and the control circuit (i.e., board 76) or on its own PCB (i.e., board 78).

Figure 8J:
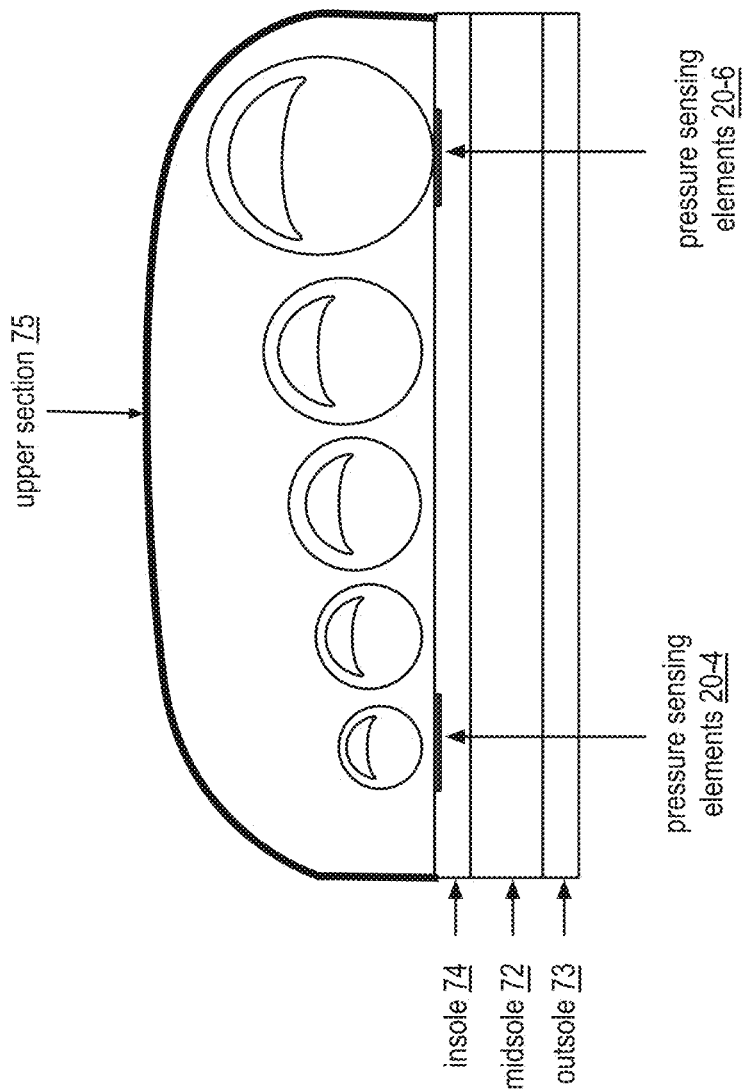
FIG. 8J is a front view diagram of another example of the pressure sensing elements positioned with respect to an insole of a shoe in accordance with the present invention.

FIG. 8J is a front view diagram of another example of the pressure sensing elements 20-4 and 20-6 positioned with respect to an insole 74 of a shoe that also includes the midsole 72, the outsole 73, and an upper section 75. In this example, pressure sensing elements 20-4 is positioned on the lateral side of the shoe (e.g., approximately under the little toe or at the fifth metatarsal) and pressure sensing elements 20-6 is positioned on the medial side of the shoe (e.g., approximately under the big toe or at the first metatarsal).

FIG. 8K is a rear-view diagram of another example of the pressure sensing elements 20-1 and 20-2 positioned with respect to an insole 74 of a shoe that also includes the midsole 72 and the outsole 73. In this example, pressure sensing elements 20-1 is positioned on the lateral side of the shoe (e.g., approximately under the outside of the heel) and pressure sensing elements 20-2 is positioned on the medial side of the shoe (e.g., approximately under the inside of the heel).

Figure 8L:
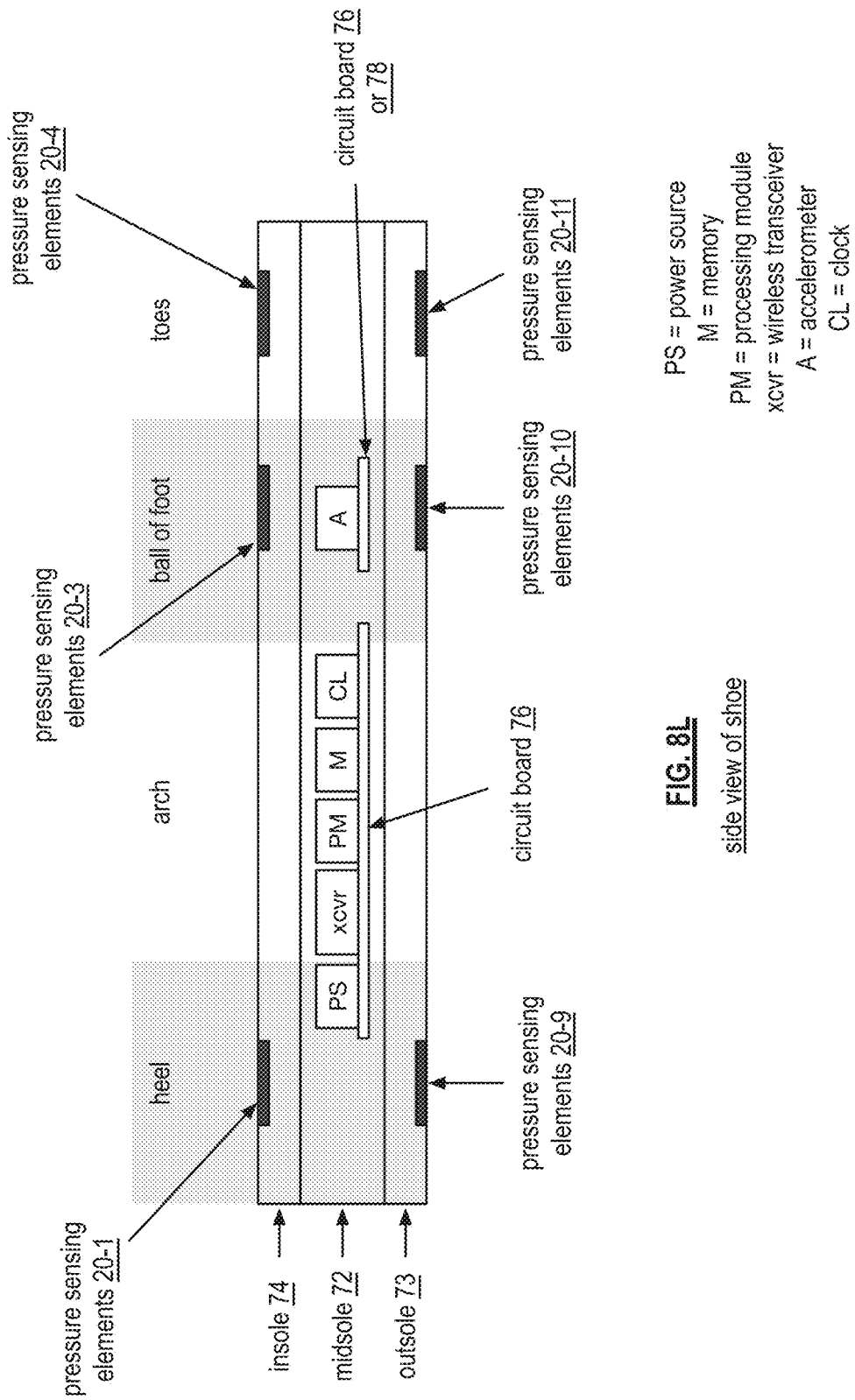
FIG. 8L is a side view diagram of another example of the pressure sensing elements positioned with respect to an insole of a shoe and the control circuit and accelerometer positioned with respect to a midsole of the shoe in accordance with the present invention.

FIG. 8L is similar to FIG. 8I with the addition of pressure sensing elements positioned in the outsole 73. Assuming this a lateral side view of the shoe, pressure sensing element 20-9 is located underneath pressure sensing element 20-1 and is positioned at or near the surface of the outsole 73. Similarly, pressure sensing element 20-10 is located underneath pressure sensing element 20-3 and is positioned at or near the surface of the outsole 73 and pressure sensing element 20-11 is located underneath pressure sensing element 20-4 and is positioned at or near the surface of the outsole 73. The medial side may also include pressure sensing elements in the outsole 73 that mirror the top perspective positions of pressure sensing elements 20-2, 20-5, and 20-6.

With pressure sensing elements in both the insole 74 and outsole 73, pressure exerted by the foot into the can be measured as well as the pressure exerted by the shoe on to the ground or surface. With this data, the energy transfer effectiveness and energy transfer function of the shoe can be determined. For example, the energy transfer effectiveness measures the loss of energy as a result of the shoe. As another example, the energy transfer function corresponds to how the shoe transfers energy from the insole to the midsole.

FIG. 8M is similar to FIG. 8J with the addition of a pressure sensing element 20-12 being positioned on the lateral wall of the shoe. The shoe may include more than one pressure sensing element along the lateral wall. With one or more pressure sensing elements along the lateral wall of the shoe, horizontal forces can be measured as the person is cutting, making a lateral movement, etc. while wearing the shoes.

Figure 8N:
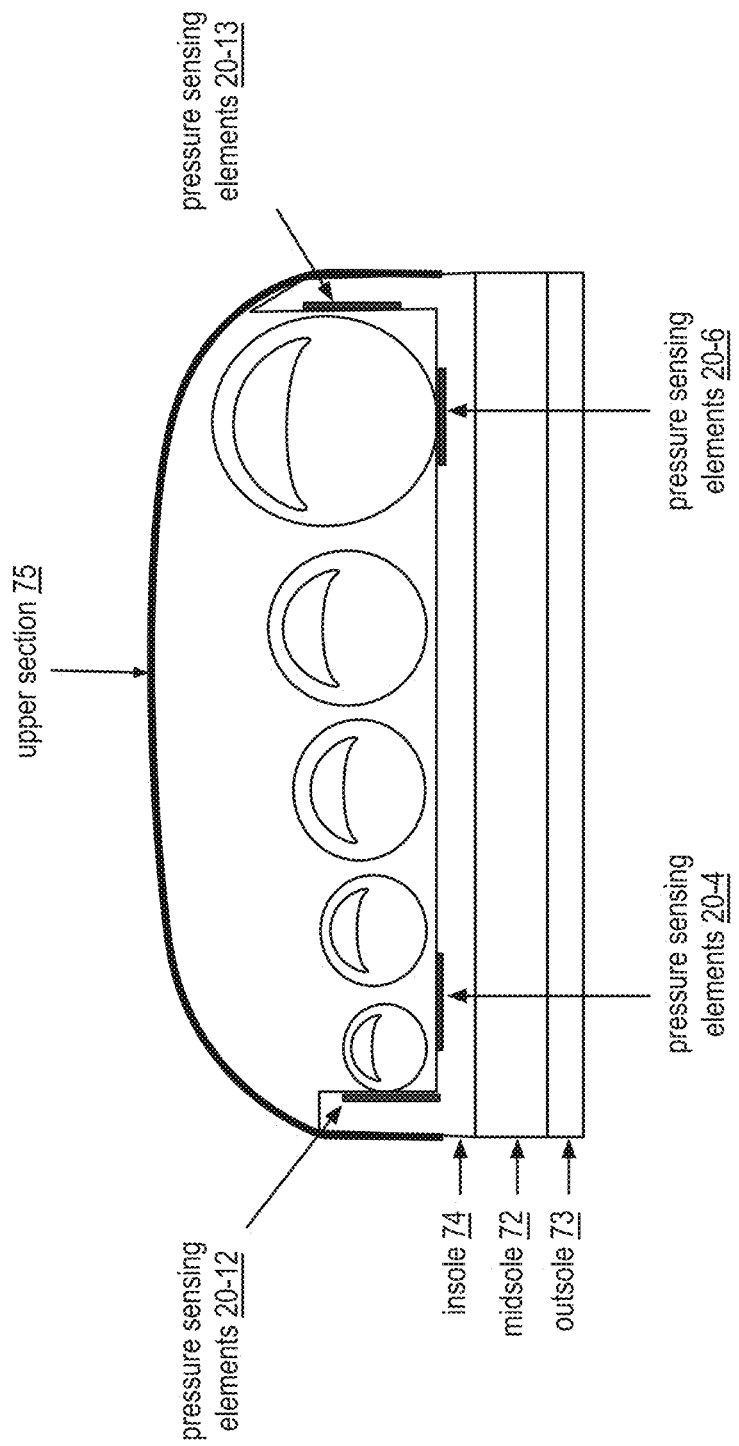
FIG. 8N is a front view diagram of another example of the pressure sensing elements positioned with respect to an insole of a shoe in accordance with the present invention.

FIG. 8N is similar to FIG. 8M with the addition of a pressure sensing element 20-13 being positioned on the medial wall of the shoe. The shoe may include more than one pressure sensing element along the medial wall. With one or more pressure sensing elements along the medial wall of the shoe, horizontal forces in both directions can be measured as the person is cutting, making a lateral movement, etc. while wearing the shoes.

Figure 9:
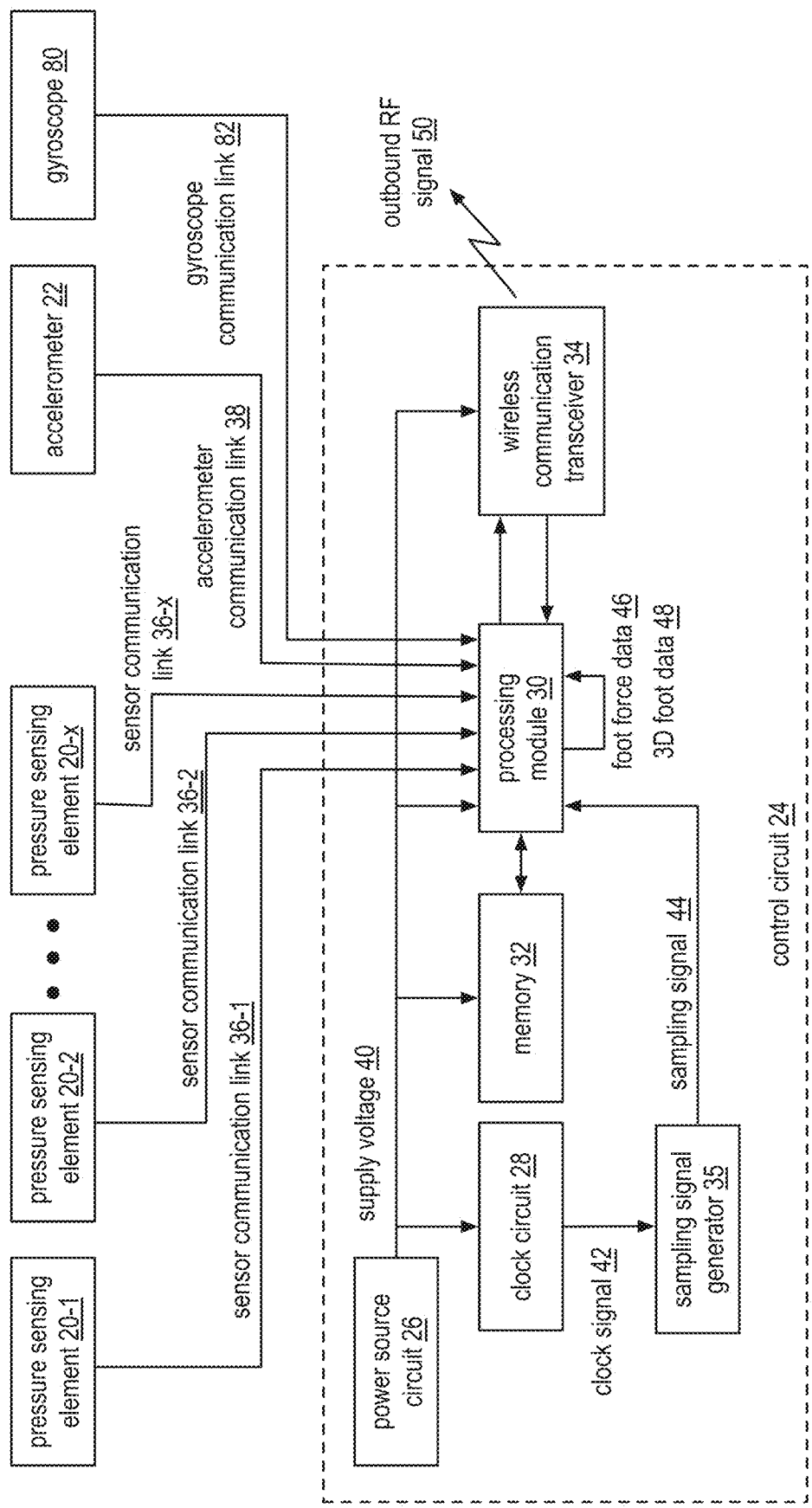
FIG. 9 is a schematic block diagram of another embodiment of a shoe sensor system in accordance with the present invention.

FIG. 9 is a schematic block diagram of another embodiment of a shoe sensor system 16 R & L that is similar to the system depicted in FIG. 4. In this embodiment, the system 16 further includes a gyroscope 80 that is coupled to the processing module of the control circuit 24 via a gyroscope communication link 82. The gyroscope communication link 82 is one or more of a wired communication link (e.g., a wire), a wired communication path in accordance with a wired communication protocol, an inductive communication path in accordance with a near field communication (NFC) communication protocol, a light communication base in accordance with a light-based communication protocol and a radio frequency (RF) communication path in accordance with a wireless communication protocol.

The gyroscope 80 may be on the same PCB as the control circuit 24, may be on a separate PCB with the accelerometer, or on its on PCB positioned within the shoe. Regardless of its inclusion of a PCB, the gyroscope generates pitch, yaw, and roll coordinates. The processing module 30 samples, in accordance with the sampling signal 44, the pitch, yaw, and roll coordinates to produce pitch, yaw, and roll data. The processing module 30 also correlates the pitch, yaw, and roll data with the foot force data 46 and the 3D foot data to produce the correlated data. The wireless communication transceiver 34 transmits the outbound RF signals 50, which includes the correlated data.

Figure 10:
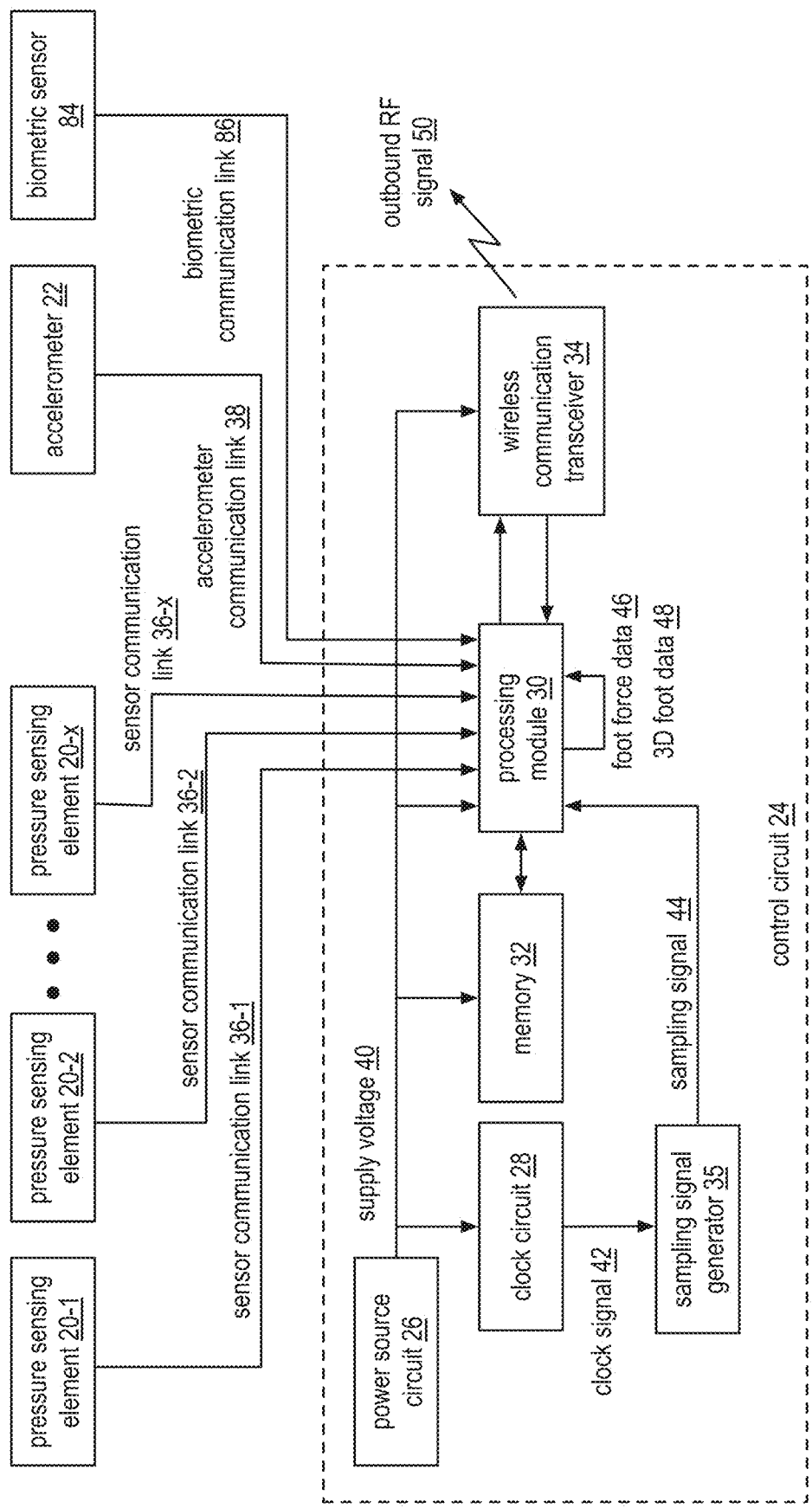
FIG. 10 is a schematic block diagram of another embodiment of a shoe sensor system in accordance with the present invention.

FIG. 10 is a schematic block diagram of another embodiment of a shoe sensor system 16 R & L that is similar to the system depicted in FIG. 4. In this embodiment, the system 16 further includes a biometric sensor 84 that is coupled to the processing module of the control circuit 24 via a biometric communication link 86. The biometric communication link 86 is one or more of a wired communication link (e.g., a wire), a wired communication path in accordance with a wired communication protocol, an inductive communication path in accordance with a near field communication (NFC) communication protocol, a light communication base in accordance with a light-based communication protocol and a radio frequency (RF) communication path in accordance with a wireless communication protocol.

The biometric sensor 84 is on, or in, the surface of the insole to measure a biometric condition of the person wearing the shoes via the person's feet. For instance, the biometric condition includes one or more of heart rate, perspiration, respiration, temperature, etc. As such, the biometric sensor 84 generates biometric indicators regarding one or more of heart rate, moisture level, respiration, and temperature.

The processing module 30 samples, in accordance with the sampling signal 44, the biometric indicators to produce biometric data. The processing module 30 also correlates the biometric data with the foot force data 46 and the 3D foot data to produce the correlated data. The wireless communication transceiver 34 transmits the outbound RF signals 50, which includes the correlated data.

To improve the connectivity of the biometric sensor 84 to the skin of the person wearing the shoes, the person may wear socks with metallic thread in the bottom of the sock. The metallic thread is woven into the sock at one or more locations that corresponds to the position of the biometric sensor. Note that each shoe may include a plurality of biometric sensors, each measuring a different biometric condition.

Figure 11:
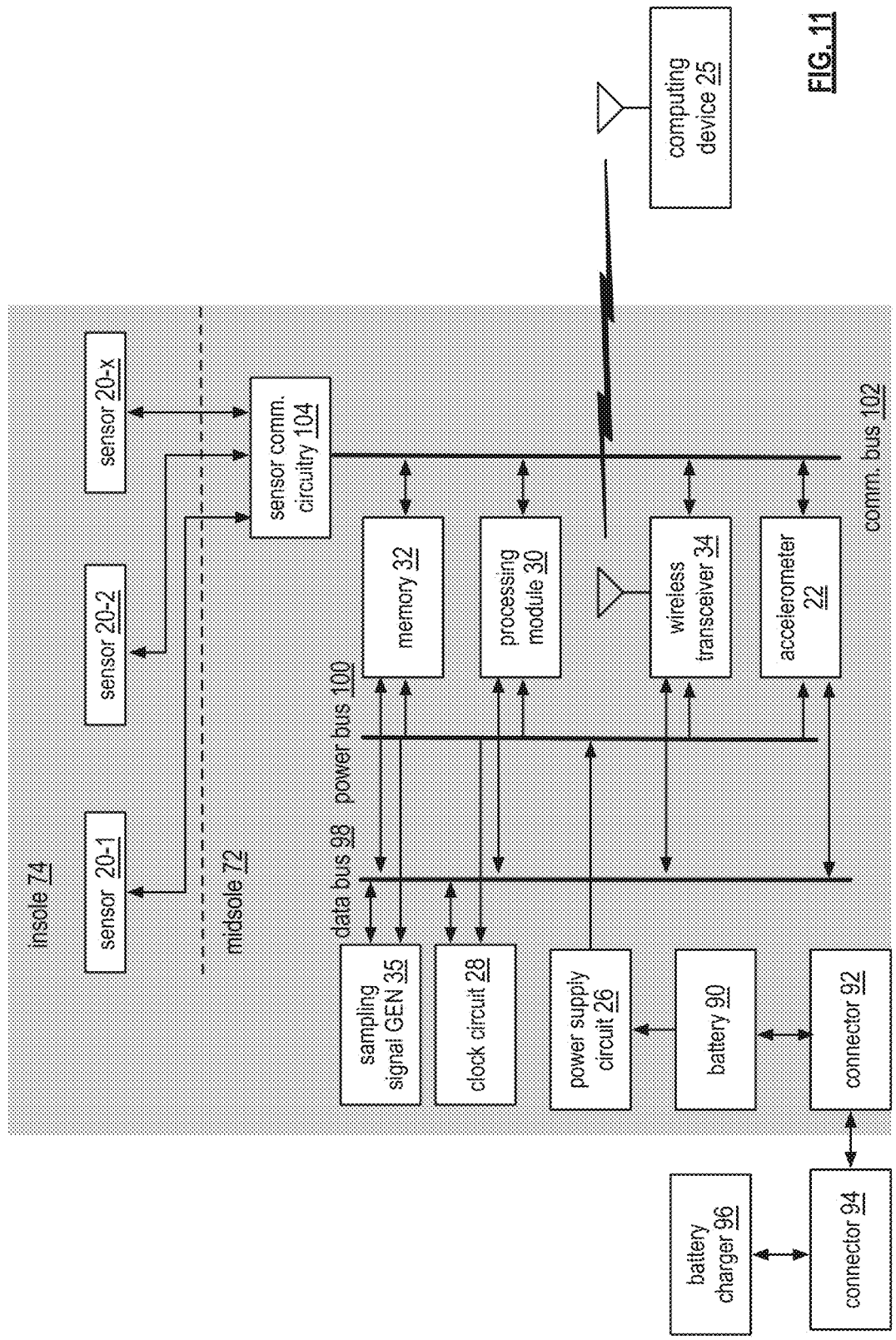
FIG. 11 is a schematic block diagram of another embodiment of a shoe sensor system in accordance with the present invention.

FIG. 11 is a schematic block diagram of another embodiment of a shoe sensor system 16 R & L that wirelessly communicates with the computing device 25. The system 16 includes pressure sensor elements 20-1 through 20-x, an accelerometer 22, sensor communication circuit 104, a data bus 98, a power bus 110, a communication bus 102, a power source circuit 24, a clock circuit 28, a processing module 30, memory 32, a wireless communication transceiver 34, a sampling signal generator 35, a battery 96, a connector set 92 & 94, and a battery charger 96.

Each of the buses 98, 100, and 102 includes a single shared link, a plurality of shared links, a plurality of individual links, or a combination thereof. A link is a wired communication link (e.g., a wire), a wired communication path in accordance with a wired communication protocol, an inductive communication path in accordance with a near field communication (NFC) communication protocol, a light communication base in accordance with a light-based communication protocol and a radio frequency (RF) communication path in accordance with a wireless communication protocol.

The pressure sensor elements 20-1 through 20-x, the accelerometer 22, the power source circuit 24, the clock circuit 28, the processing module 30, the memory 32, the wireless communication transceiver 34, and the sampling signal generator 35 function as previously described with reference to one or more of the preceding figures and/or as will be described with reference to one or more of the subsequent figures.

The battery 90 is a rechargeable battery that powers the power supply circuit 26, which produces one or more supply voltages. The battery 90 is recharged by the battery charger 96, which may be an external device to the shoe or including within the shoe. In the example, shown, the battery charger 96 is an external device that is connected to the battery 90 via connectors 92 and 94. In an embodiment, the connectors 92 and 94 are wired connectors that provide electrical coupling via wires, pins, receptacles, etc. In another embodiment, the connectors 92 and 94 are wireless to provide NFC wireless charging. Note that the connector may be in the heel section of the shoe and positioned to not interfere with wearing of the shoes.

FIG. 12 is a top view diagram of an example of the pressure sensing elements 20 that are RF coupled to the control circuit 24. Each pressure sensing element 20 is one the insole 74 and associated with an antenna 110-1 through 110-6, where pressure sensing element 20-1 is associated with antenna 110-1 and so on. With reference to FIG. 13A, which is a side view diagram of the shoe, the pressure sensing element antennas 110 are positioned over a midsole antenna 112. The midsole antenna 112 is coupled to the control circuit 24.

In an example of operation, the wireless transceiver (XCVR) is in a first mode to wirelessly communicate with the pressure sensing elements 20. In the first mode, the wireless transceiver generates a low power RF signal that includes a continuous wave portion to enable passive pressure sensing elements 20 to produce a supply voltage that powers the sensing element 20. The transceiver then generates RF control signals requesting the pressure sensing elements 20 to respond with their pressure sensing measurements.

After the control circuit 24 has gathered sufficient pressure sensing measurements from the sensing elements, the transceiver switches to a second mode to communicate the correlated data to the computing device 25. The transceiver switches between the first and second modes to gather data and to provide the data to the computing device. Note that the frequency used to communicate with the sensing elements may be the same or different than the frequency used to communicate with the computing device and the frequency ranges from a few hundred Mega Hertz to 60 GHz or more. As a specific example, the transceiver communicates with the computing device using a frequency of 2.4 GHz and communicates with the sensing elements using 60 GHz.

Figure 13B:
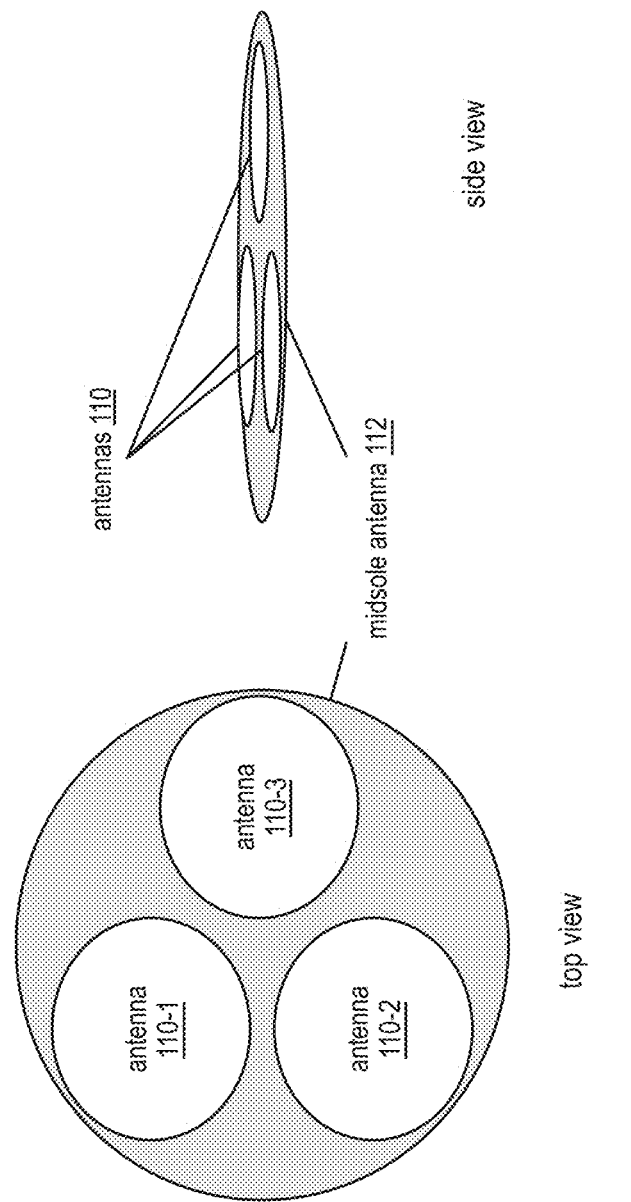
FIG. 13B is a top and a side view diagram of an example of the pressure sensing element antennas positioned with respect to the antenna of the control circuit in accordance with the present invention.

FIG. 13B is a top and a side view diagram of an example of the pressure sensing element antennas 110 positioned with respect to the midsole antenna 112. In this example, the antenna 112 has a surface area that encompasses the surface area of the three (or more) pressure sensing element antennas 110. In an example, the midsole antenna 112 communicates with one pressure sensing element antenna 110 at a time. In another example, the midsole antenna 112 communicates with two or more pressure sensing element antennas 110 at the same time using a frequency division multiplexing scheme.

Figure 13C:
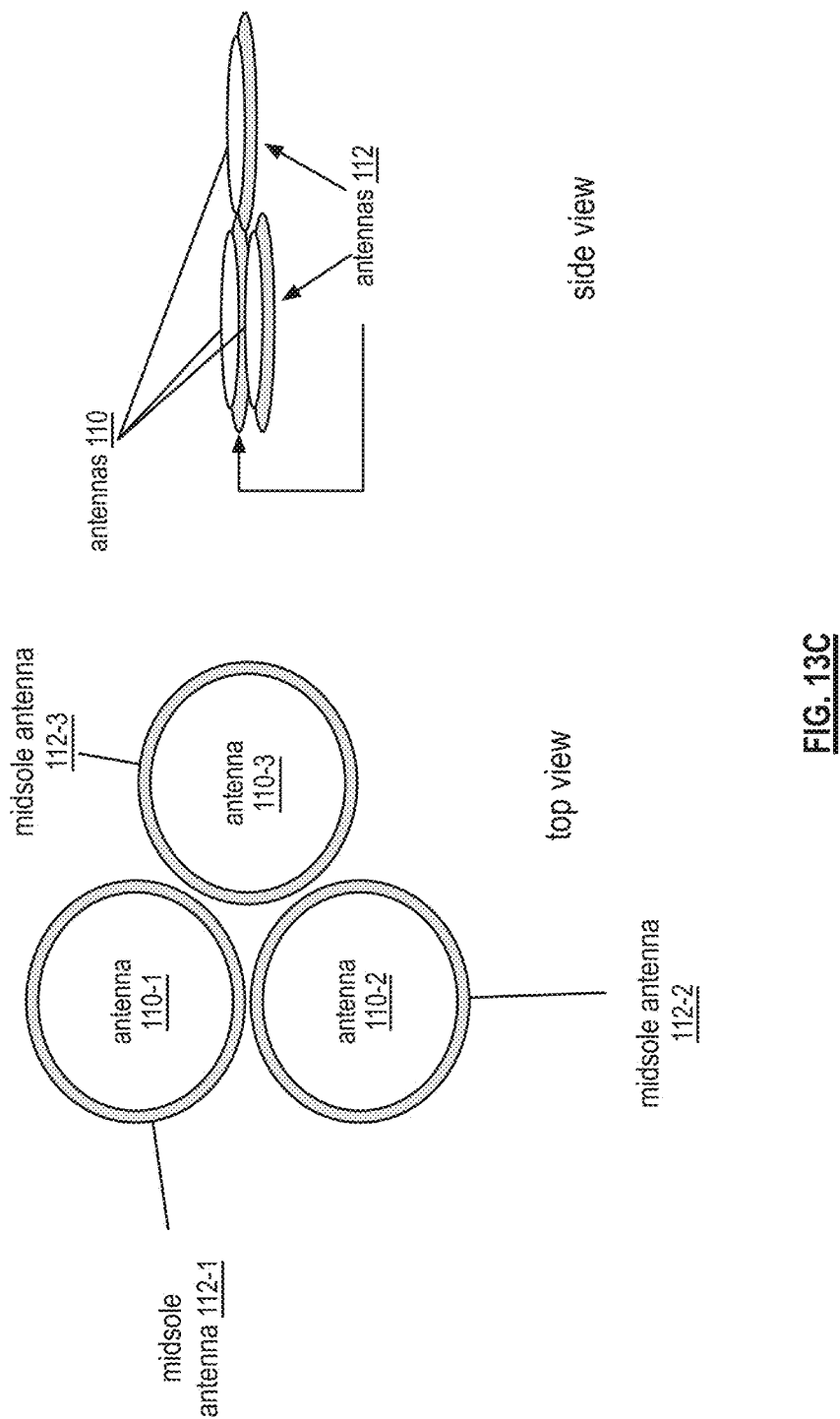
FIG. 13C is a top and a side view diagram of another example of the pressure sensing element antennas positioned with respect to the antenna of the control circuit in accordance with the present invention.

FIG. 13C is a top and a side view diagram of another example of the pressure sensing element antennas 110 positioned with respect to multiple midsole antennas 112. In this example, each midsole antenna 112 has a surface area that is about the same size as the surface area of a pressure sensing element antenna 110. In an example, each midsole antenna 112 communicates with a corresponding pressure sensing element antenna 110 at a time using the same or different frequencies. In another example, each midsole antenna 112 communicates with its corresponding pressure sensing element antennas 110 in a time division multiplexing manner using the same or different frequencies.

Figure 14:
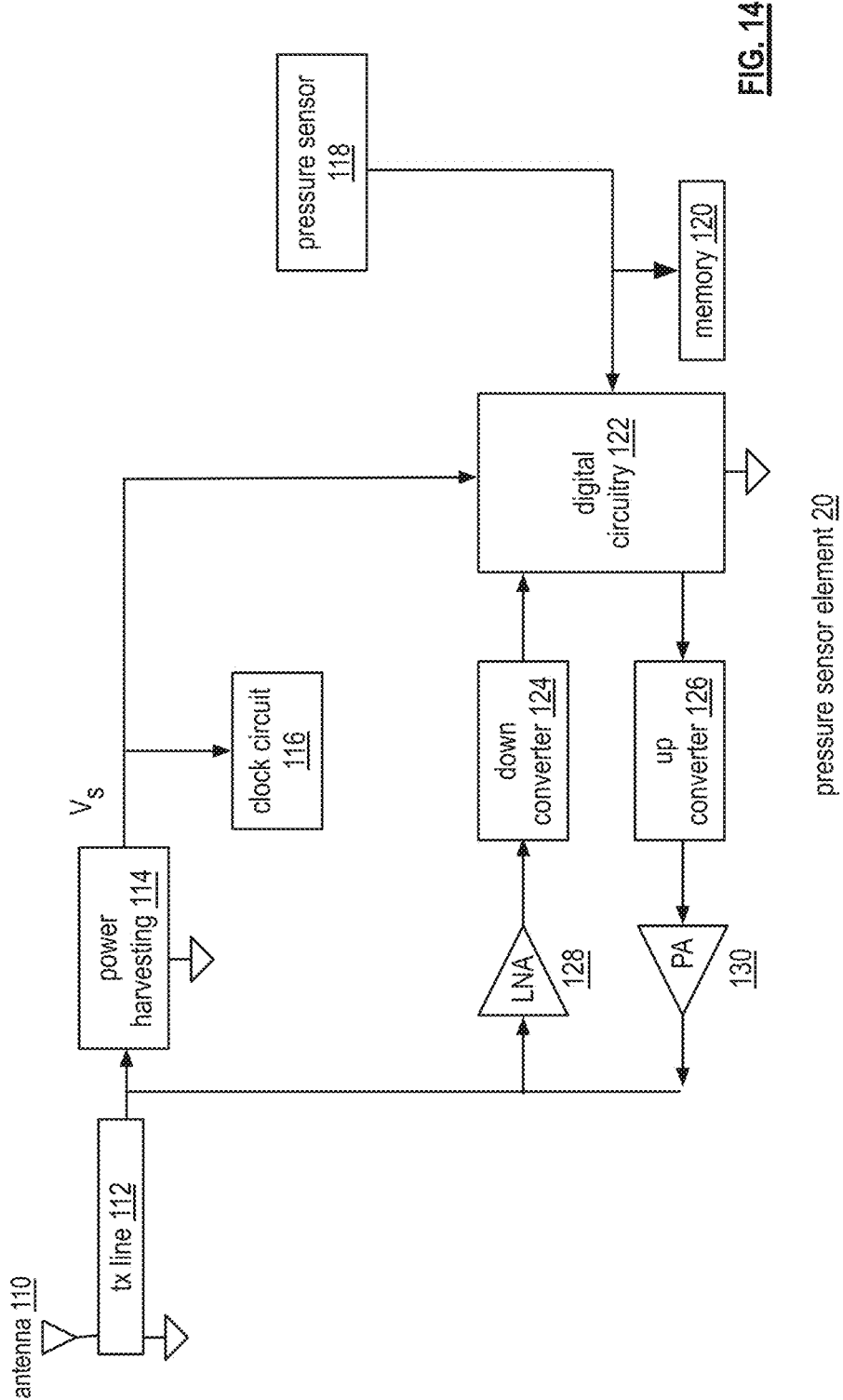
FIG. 14 is a schematic block diagram of an embodiment of a pressure sensing element in accordance with the present invention.

FIG. 14 is a schematic block diagram of an embodiment of a pressure sensing element 20 that includes an antenna 110, a transmission line 112, a power harvesting circuit 114, a clock circuit 116, a pressure sensor 118, memory 120, digital circuitry 122, a down converter 124, an up converter 126, a low noise amplifier (LNA) 128 and a power amplifier (PA) 130. The transmission line 112 coupled the antenna 110 to the power harvesting circuit 114, the receiver 128, and the transmitter 130. Depending on the location of the antenna 110 and the pressure sensing element with the shoe, the transmission line 112 may be a few millimeters long to tens of centimeters long.

In an example of operation, the antenna 110 receives an RF signal from the control circuit (via the transceiver 34 and/or another transceiver). The power harvesting circuit 114 converts the RF signal into a supply voltage Vs, which powers the rest of the circuit. Once power is available, the pressure sensor 118 begins sensing pressure and provides pressure sensory signals to the digital circuitry 122. The digital circuitry 122, which may be implemented as a processing module, converts the pressure sensory signals into the pressure sensed data in accordance with a sampling clock generated by the clock circuit 116.

The up converter 126 converts the pressure sensed data into an RF signal that is amplified by the PA 130 and transmitted by the antenna 110. The digital circuitry 122, the up converter 126, and/or the PA 130 may use backscattering, Amplitude Shift Keying (ASK), Amplitude Modulation (AM), Frequency Shift Keying (FSK), and/or Phase Shift Keying (PSK) to convert the pressure sensed data into a transmitted RF signal. Note that the memory 120 may store the pressure sensed data until it is transmitted or may store the pressure sensed data indefinitely.

The pressure sensing element 20 may provide the pressure sensed data at predetermined intervals or in response to a request for data. For the latter, the antenna receives an inbound RF signal that is amplified by the LNA 128 and down converted into a baseband signal via the down converter 124. The digital circuitry 122 processes the baseband signal to identify the request for data.

Figure 15:
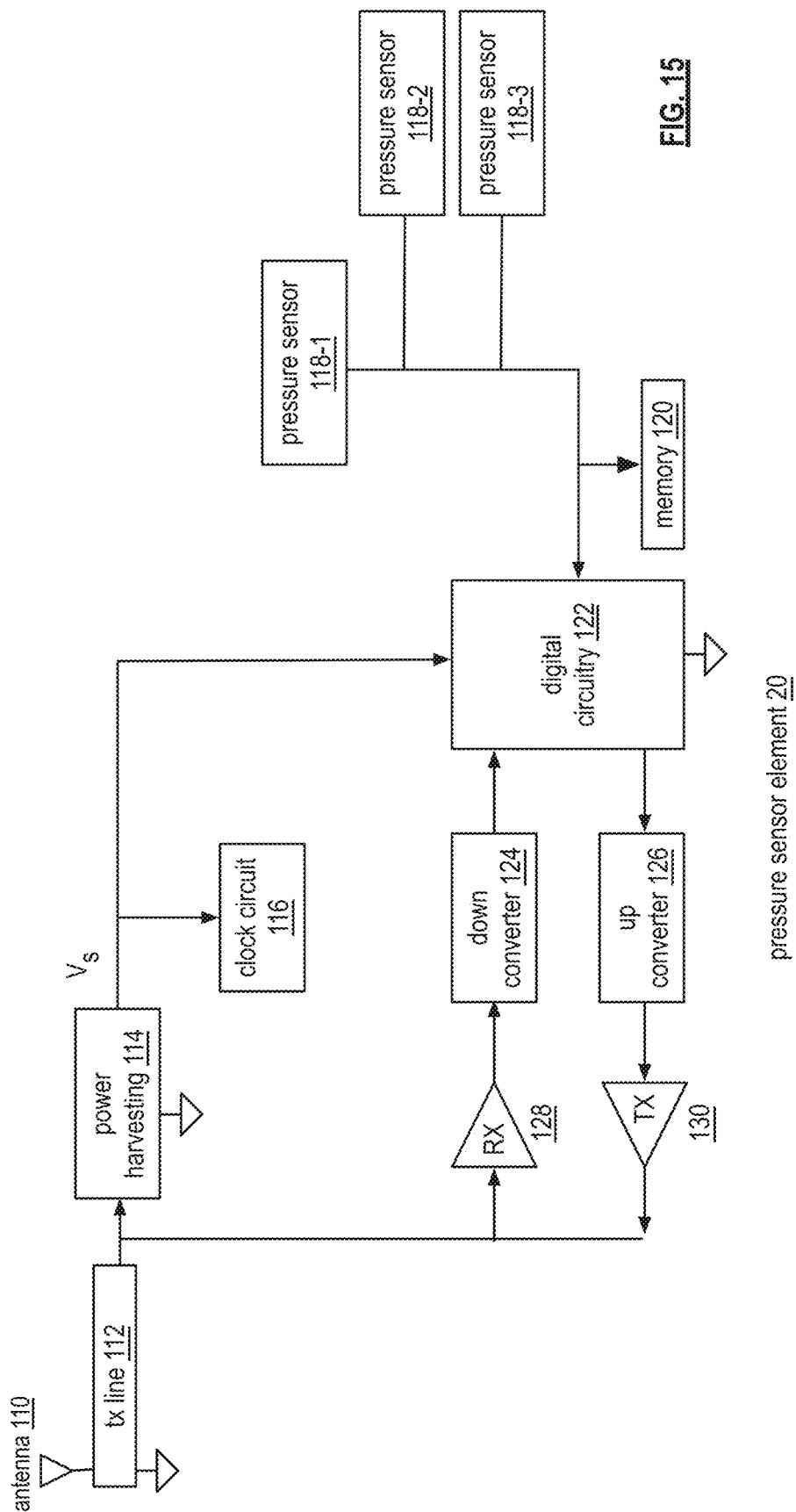
FIG. 15 is a schematic block diagram of another embodiment of a pressure sensing element in accordance with the present invention.

FIG. 15 is a schematic block diagram of another embodiment of a pressure sensing element 20 that is similar to the one of FIG. 14 with the inclusion of a plurality of pressure sensors 118-1 through 118-3 (3 are shown but could include more or less than 3). The pressure sensors 118-1 through 118-3 may each be the same type of sensor (e.g., resistive, capacitive, inductive, piezoelectric, etc.) to sense pressure in a same area or in different areas. In an example, the pressure sensors are of the same type and have different pressure ratings (e.g., one from 10-100 force pounds, a second from 100-200 force pounds, and a third from 200-400 force pounds). In another example, the pressure sensors are of different types and of the same pressure ratings, which can be averaged and/or used for calibration.

Figure 16:
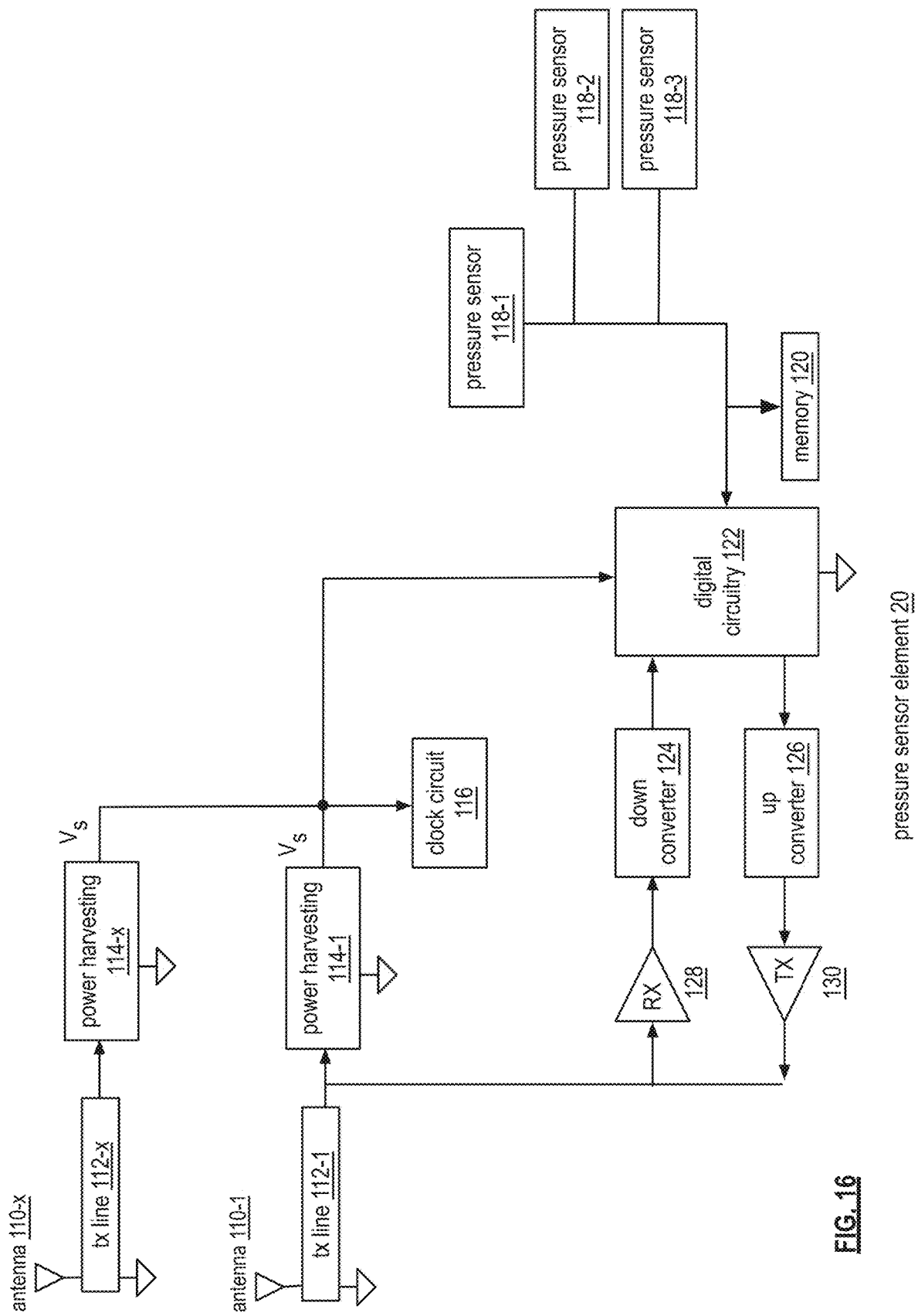
FIG. 16 is a schematic block diagram of another embodiment of a pressure sensing element in accordance with the present invention.

FIG. 16 is a schematic block diagram of another embodiment of a pressure sensing element 20 that is similar to the one of FIG. 14 with the inclusion of multiple antennas 110-1 through 110-x, multiple transmission lines 112-1 through 112-x, and multiple power harvesting circuits 114-1 through 114-x. In this embodiment, the multiple antennas and power harvesting circuits increase the power available for the pressure sensing element 20.

Figure 17B:
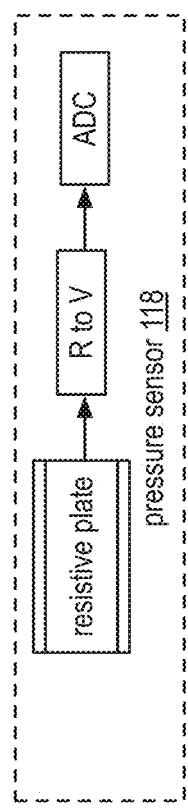
FIGS. 17A-17D are schematic block diagrams of example embodiments of a pressure sensor in accordance with the present invention.
Figure 17D:
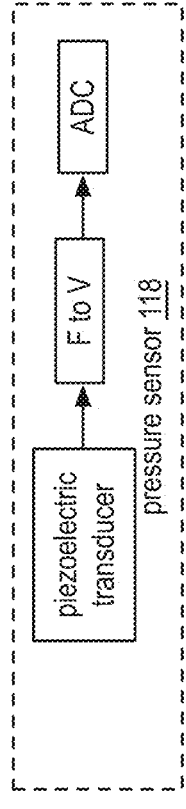
Figure 17A:
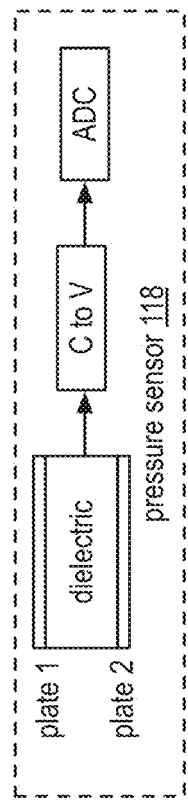

FIG. 17A is a schematic block diagram of a capacitive pressure sensor 118 that includes a capacitor (e.g., plates 1 and 2 and a dielectric), a capacitance to voltage converter (C to V), and an analog to digital converter (ADC). In an alternative embodiment, the ADC is in the digital circuitry of the pressure sensing element of FIGS. 14-16 or in the control circuit 24. When pressure is applied to the capacitor, the dielectric changes causes a capacitance change. The capacitance change is converted to an analog voltage by the capacitance to voltage converter. The ADC converts the analog voltage into a digital value that represented the pressure data.

FIG. 17B is a schematic block diagram of a resistive pressure sensor 118 that includes a resistor (e.g., resistive plate), a resistance to voltage converter (R to V), and an analog to digital converter (ADC). In an alternative embodiment, the ADC is in the digital circuitry of the pressure sensing element of FIGS. 14-16 or in the control circuit 24. When pressure is applied to the resistive plate, its resistance changes. The resistive change is converted to an analog voltage by the resistance to voltage converter. The ADC converts the analog voltage into a digital value that represented the pressure data.

Figure 17C:
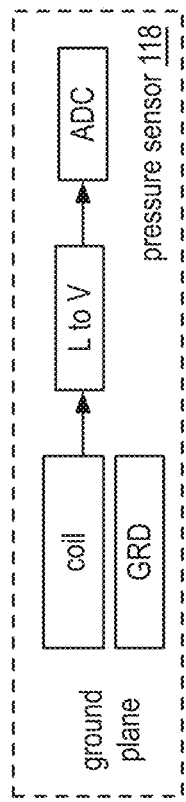

FIG. 17C is a schematic block diagram of an inductive pressure sensor 118 that includes an inductor (e.g., a coil proximal to a ground plane), an inductance to voltage converter (L to V), and an analog to digital converter (ADC). In an alternative embodiment, the ADC is in the digital circuitry of the pressure sensing element of FIGS. 14-16 or in the control circuit 24. When pressure is applied to the inductor, the coil is pressed closer to the ground plane causes an inductance change. The inductance change is converted to an analog voltage by the inductance to voltage converter. The ADC converts the analog voltage into a digital value that represented the pressure data.

FIG. 17D is a schematic block diagram of a frequency pressure sensor 118 that includes a piezoelectric transducer, a frequency to voltage converter (F to V), and an analog to digital converter (ADC). In an alternative embodiment, the ADC is in the digital circuitry of the pressure sensing element of FIGS. 14-16 or in the control circuit 24. When pressure is applied to the piezoelectric transducer, its resonating frequency changes. The frequency change is converted to an analog voltage by the frequency to voltage converter. The ADC converts the analog voltage into a digital value that represented the pressure data.

Figure 18:
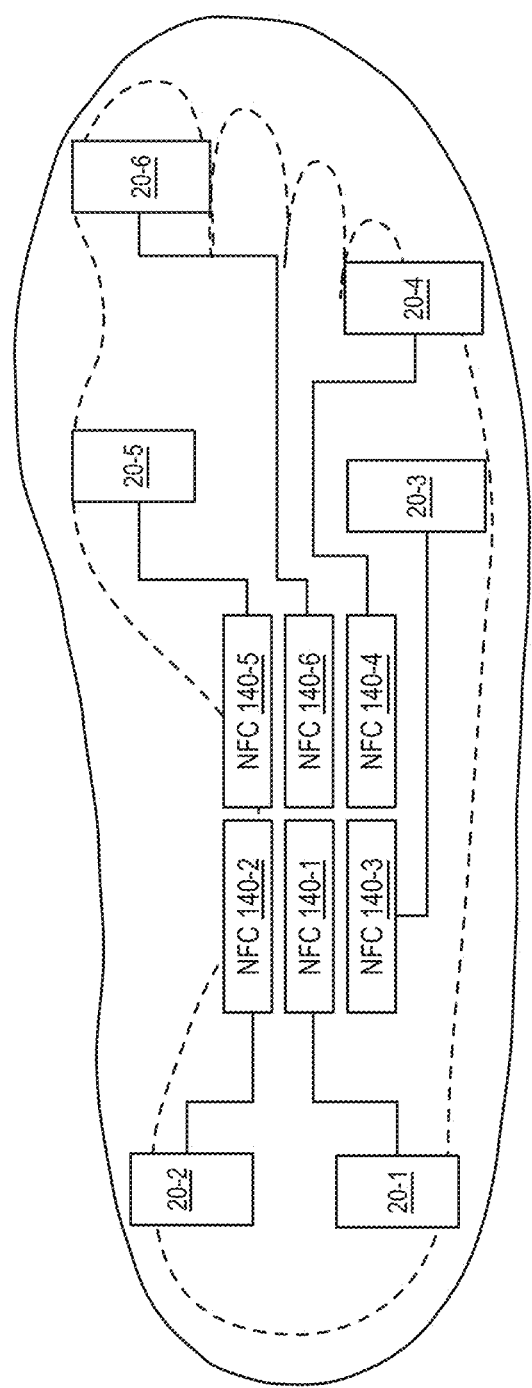
FIG. 18 is a top view diagram of an example of the pressure sensing elements and corresponding NFC coils positioned with respect to an insole of a shoe in accordance with the present invention.
Figure 19A:
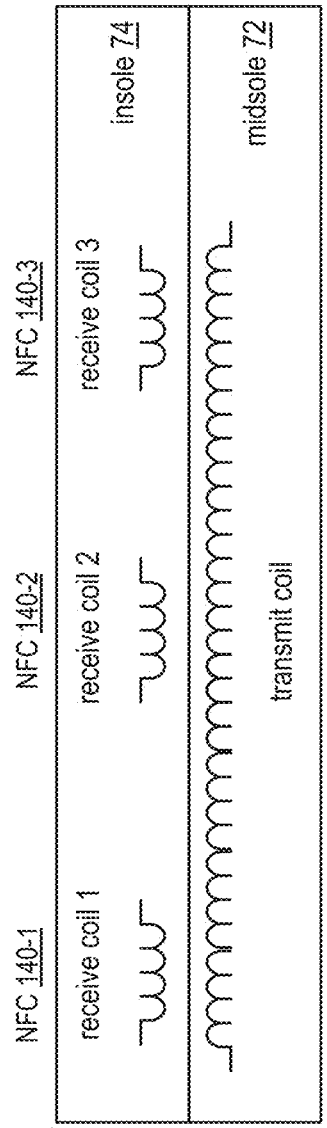
FIG. 19A is a side view diagram of an example of receiving NFC coils positioned with respect to an insole of a shoe and a transmitting NFC coil positioned with respect to a midsole of the shoe in accordance with the present invention.
Figure 19B:
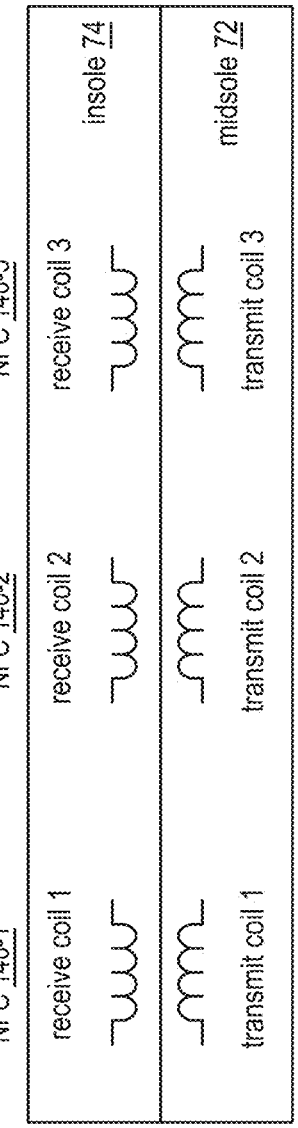
FIG. 19B is a side view diagram of an example of receiving NFC coils positioned with respect to an insole of a shoe and transmitting NFC coils positioned with respect to a midsole of the shoe in accordance with the present invention.

FIG. 18 is a top view diagram of an example of the pressure sensing elements 20 that are inductively coupled to the control circuit 24. Each pressure sensing element 20 is one the insole 74 and associated with an NFC coil 140-1 through 140-6, where pressure sensing element 20-1 is associated with NFC coil 110-1 and so on. With reference to the side view diagram of FIG. 19A, the pressure sensing element antennas 110 are positioned over a midsole NFC transmission coil, which is coupled to the control circuit 24. In the alternative and with reference to the side view diagram of FIG. 19B, the pressure sensing element antennas 110 are positioned over corresponding midsole NFC transmission coils, which are coupled to the control circuit 24. The NFC coils may communicate using frequencies ranging from tens of MHz to tens of GHz, or more.

Figure 20:
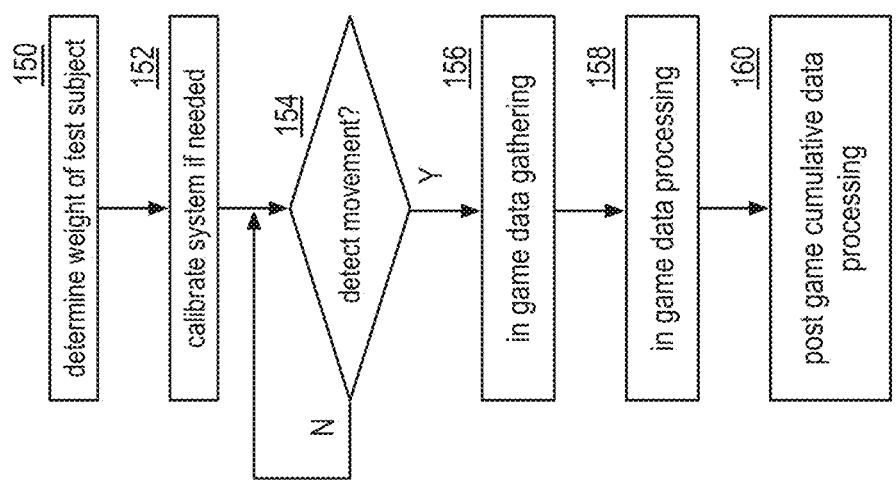
FIG. 20 is a logic diagram of another example of a method executed by a shoe sensor system in accordance with the present invention.

FIG. 20 is a logic diagram of another example of a method executed by a shoe sensor system that begins at step 150 where the system determines the weight of the person wearing the shoes. For example, a person's weight can be determined by having them stand on one foot, take force measurements for this foot, stand on the other foot, and take force measurements for the other foot. From the force measurements, weight is calculated.

The method continues at step 152 where the system is calibrated if needed. For example, if the determination of a person's weight from the force measurements differs from a weight measurement from a scale, then the system can be calibrated (e.g., change coefficients for force measurements to weight conversion). Once the system is calibrated, the method continues at step 154.

At step 154, the system determines whether it detects movement. If not, the system waits until movement is detected and stays in a low power mode (e.g., reduced supply voltage, lower clock rate, no sampling, etc.). When movement is detected (e.g., accelerometer data is detected, the person enables the system to start tracking physical activity, detecting foot forces that corresponds to movement, etc.). The method then continues at step 156 where the system produces correlated data during a game, practice, or other event.

The method continues at step 158 where the system or the computing device processing the in-game correlation data to produce physical activity monitoring data. Various examples of processing the correlated data will be described with reference to one or more of FIGS. 21-28. The method continues at step 160 where the system or the computing device processes post game data. For example, the system or the computing device add the most recent game data to data from previous games to produce historical data.

Figure 21:
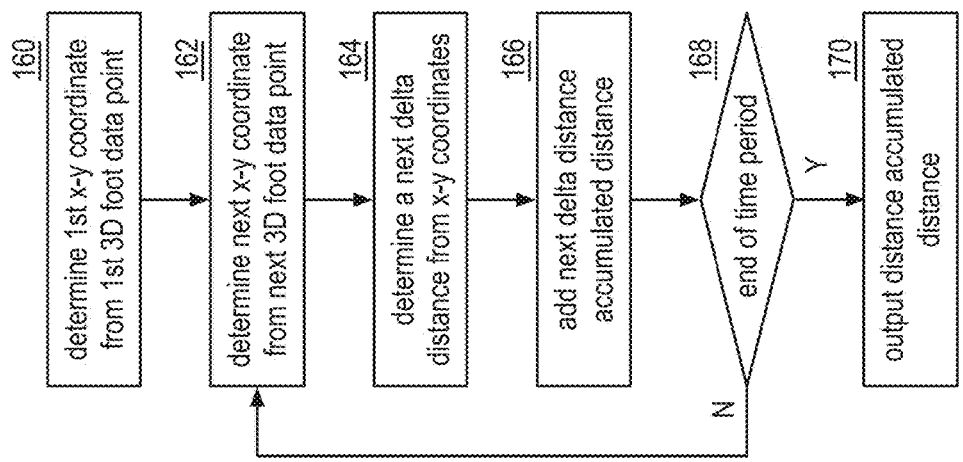
FIG. 21 is a logic diagram of another example of a method executed by a shoe sensor system in accordance with the present invention.

FIG. 21 is a logic diagram of another example of a method executed by a shoe sensor system to determine the distance traveled during the time period (e.g., for the duration of the physical activity, a portion of the physical activity, etc.). The method begins at step 160 where the processing module (e.g., processing module 30 of the system 10 and/or processing module 27 of the computing device 25) determines a first x-y coordinate from a first three-dimensional foot data point (e.g., from an x-y-z coordinate from the accelerometer) that corresponds to the beginning of the time period. For example, the first x-y coordinate corresponds to the first data sampled from the accelerometer when the system was activated to record physical activity data. As another example, the first x-y coordinate corresponds to the first data sampled from the accelerometer at the start of a new time interval of the physical activity monitoring.

The x-y coordinate of the x-y-z coordinate correspond to a position on the surface of the ground and the z-coordinate of the x-y-x coordinate corresponds to an up position with respect to the ground. The first x-y-x coordinate corresponds to an original of a reference Cartesian or Polar coordinate system for tracking the distance the shoes travel.

The method continues at step 162 where the processing module determines a next x-y coordinate from a next three-dimensional foot data point. The next 3D foot data point corresponds to the accelerometer data taking at the next sampling interval, or point, of the sampling clock with respect to the previous sampling interval using absolute values to get an accumulation of movement. For example, the first x-y-z coordinate was taking at sampling interval 0, the second x-y-z coordinate was taking at sampling interval 1, the third x-y-z coordinate was taking at sampling interval 2, and so on until the last sampling interval of the time period.

The method continues at step 164 where the processing module determines a next delta distance based on a difference between the first x-y coordinate and the next x-y coordinate. For example, if the first x-y coordinate is 0,0 and the second x-y coordinate is 0.5, 0.75, then the delta distance includes a delta x of 0.5 and a delta y of 0.75. For the next sampling interval, the third x-y coordinate is 0.65, 1.125. As such, the delta x from the second to third coordinate is 0.15 and the delta y is 0.375. For each sampling interval, the delta distance may be stored for further and/or subsequent processing.

The method continues at step 166 where the processing module adds the next delta distance to an accumulation of previous delta distances to produce an updated accumulation of delta distances. For example, after sampling interval 1, the processing module adds the new delta data of 0.5 for delta x and 0.75 for delta y to the accumulated delta data (which is 0, 0 since the tracking process is just beginning). The result of the adding yields an updated accumulated delta distance of 0.5, 0.75. Continuing with the example for sample interval 2, the new delta data includes 0.15 for delta x and 0.375 for delta y. Adding the new delta data to the accumulated data yields an updated accumulated data of 0.65, 1.125.

The method continues at step 168 where the processing module determines whether the end of the time period has been reached. For example, the user ends the tracking of physical activity. As another example, detecting a stoppage of the physical activity. As yet another example, detection of expiration of the time period. If the time period has not ended, the method repeats at step 162 for the next data from the next sampling interval. If the time period has ended, the method continues at step 170 where the accumulated data is outputted as the distance traveled during the time period.

Figure 22A:
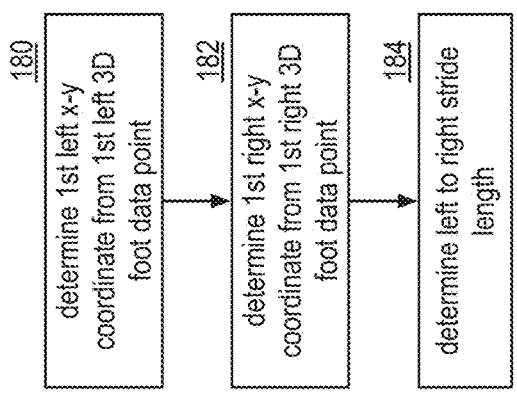
FIG. 22A is a logic diagram of another example of a method executed by a shoe sensor system in accordance with the present invention.

FIG. 22A is a logic diagram of another example of a method executed by a shoe sensor system to determine stride length data. Stride length data includes one or more of maximum length, minimum stride length, average stride length for the duration of the physical active, average stride length for an interval of the overall duration, imbalances between left-to-right stride and/or right-to-left stride, etc.

The method begins at step 180 where the processing module (e.g., processing module 30 of the system 10 and/or processing module 27 of the computing device 25) determines a first left x-y coordinate from a first left three-dimensional foot data point that corresponds to a left foot being in contact with a surface (e.g., track, ground, court, sidewalk, road, etc.).

The method continues at step 182 where the processing module determines a first right x-y coordinate from a first right three-dimensional foot data point that corresponds to a right foot being in contact with the surface after the left foot has been in contact with the surface. The method continues at step 184 where the processing module determines a left foot to right foot stride length based on the first left x-y coordinate and the first right x-y coordinate. This can be repeated for each step taking by the person wearing the shoes.

Figure 22B:
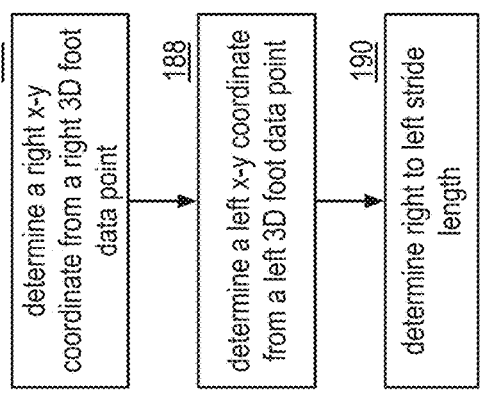
FIG. 22B is a logic diagram of another example of a method executed by a shoe sensor system in accordance with the present invention.

FIG. 22B is a logic diagram of another example of a method executed by a shoe sensor system to determine stride length data; in particular right to left stride data. The method begins at step 186 where the processing module (e.g., processing module 30 of the system 10 and/or processing module 27 of the computing device 25) determines a first right x-y coordinate from a first right three-dimensional foot data point that corresponds to a right foot being in contact with a surface (e.g., track, ground, court, sidewalk, road, etc.).

The method continues at step 188 where the processing module determines a first left x-y coordinate from a first left three-dimensional foot data point that corresponds to a left foot being in contact with the surface after the right foot has been in contact with the surface. The method continues at step 190 where the processing module determines a right foot to left foot stride length based on the first right x-y coordinate and the first left x-y coordinate. This can also be repeated for each step taking by the person wearing the shoes.

Figure 23:
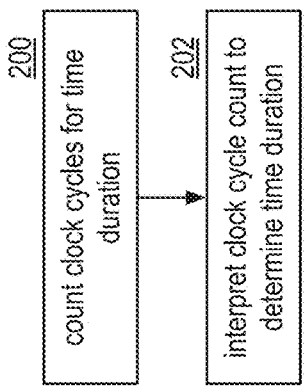
FIG. 23 is a logic diagram of another example of a method executed by a shoe sensor system in accordance with the present invention.

FIG. 23 is a logic diagram of another example of a method executed by a shoe sensor system to determine the time duration. The method begins at step 200 where the processing module (e.g., processing module 30 of the system 10 and/or processing module 27 of the computing device 25) counts clock cycle of the clock signal from a beginning of the time duration until an end of the time duration to produce a clock cycle count. The method continues at step 202 where the processing module interprets the clock cycle count in light of a clock rate of the clock signal to determine the time duration. For example, if the clock rate is 100 Hz, the number of cycles is 10,000, then the time duration is 10,000/100 or 100 seconds.

Figure 24:
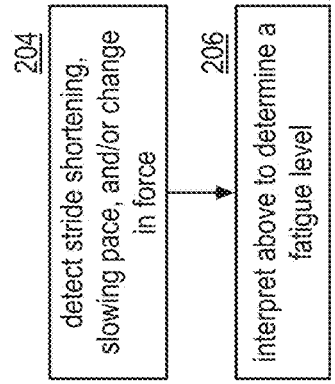
FIG. 24 is a logic diagram of another example of a method executed by a shoe sensor system in accordance with the present invention.

FIG. 24 is a logic diagram of another example of a method executed by a shoe sensor system to determine a fatigue indication. The fatigue indicator includes, but is not limited to, shortening of stride, pace slowing, change in foot forces, imbalance between left to right stride and right to left stride, etc. The method begins at step 204 where the processing module (e.g., processing module 30 of the system 10 and/or processing module 27 of the computing device 25) detects, based on changes in the correlated foot data over time within the time period, one or more of a shortening of stride length, a slowing of pace, and a change in foot force (e.g., more, less, more in heel, more on outside edge, etc.). The method continues at step 206 where the processing module interprets the one or more of a shortening of stride length, a slowing of pace, and a change in foot force to determine a fatigue level.

Figure 25:
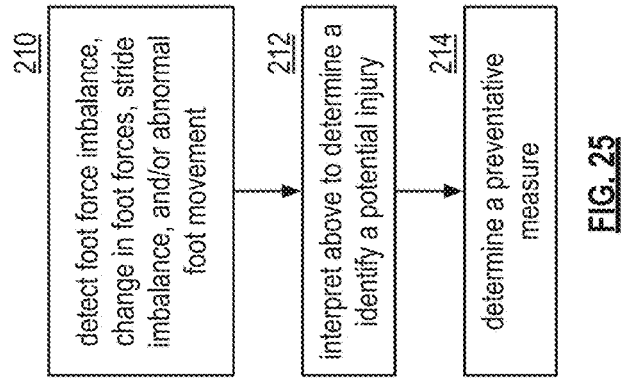
FIG. 25 is a logic diagram of another example of a method executed by a shoe sensor system in accordance with the present invention.

FIG. 25 is a logic diagram of another example of a method executed by a shoe sensor system to determine one or more injury prevention indicators. An injury prevention indicator includes, but is not limited to, recognize change in data that is likely caused by fatigue, cramping, muscle strain, imbalance in strides, imbalance in foot forces, etc.

The method begins at step 210 where the processing module (e.g., processing module 30 of the system 10 and/or processing module 27 of the computing device 25) detects an abnormality based on changes in the correlated foot data over some period of time within the time period (e.g., from interval to interval, at various time check points, etc.). The abnormality includes, but is not limited to, an imbalance in foot force between the feet, a change in foot forces of one or both feet, an imbalance in stride lengths, an imbalance in stride height (e.g., differing z components from stride to stride) between the feet, and foot movement outside of a movement deviation range (e.g., rolled ankle, dragging a foot, etc.).

The method continues at step 212 where the processing module interprets the abnormality to identify a potential injury (e.g., a potential hamstring issue, a potential calf injury, etc.). The method continues at step 214 where the processing module determines a preventive measure based on the potential injury and/or the abnormality. For example, the preventive measure is to restrict training to a maximum amount of time per day. As another example, the preventive measure is to rest for a certain number of days. As yet another example, the preventive measure is to get treatment on the body part.

Figure 26B:
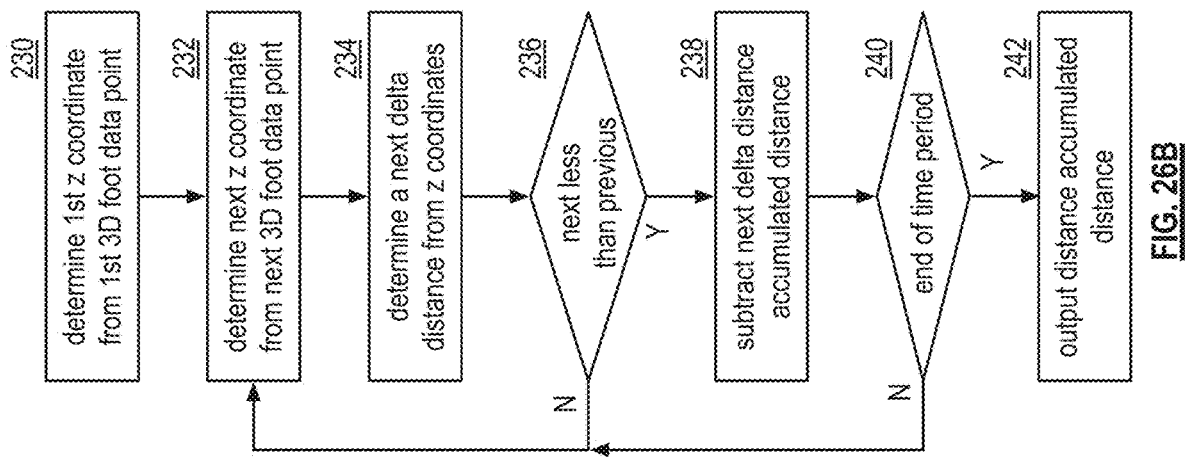
FIG. 26B is a logic diagram of another example of a method executed by a shoe sensor system in accordance with the present invention.
Figure 26A:
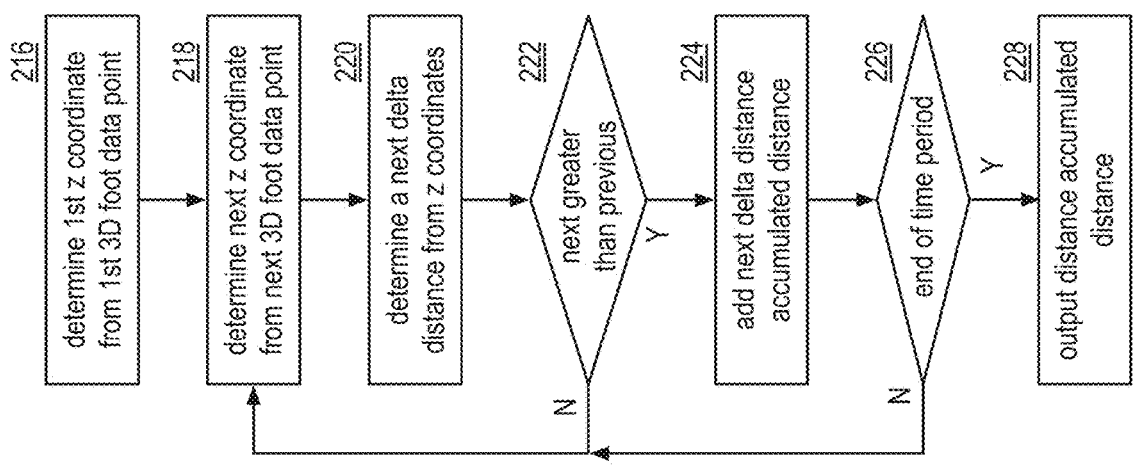
FIG. 26A is a logic diagram of another example of a method executed by a shoe sensor system in accordance with the present invention.

FIG. 26A is a logic diagram of another example of a method executed by a shoe sensor system to determine elevation tracking for the time period while performing the physical activity (e.g., steps climbed, elevation changes while running, walking, and/or hiking). The method begins at step 216 where the processing module (e.g., processing module 30 of the system 10 and/or processing module 27 of the computing device 25) determines a first z coordinate from a first three-dimensional foot data point (e.g., first x-y-z coordinate as previously described) that corresponds to the beginning of the time period.

The method continues at step 218 where the processing module determines a next z coordinate from a next three-dimensional foot data point (e.g., a next x-y-z coordinate as previously discussed) that corresponds to a next sampling point of the sampling clock within the time period. The method continues at step 220 where the processing module determines a next delta distance based on a difference between the first z coordinate and the next z coordinate. The method continues at step 222 where the processing module determines whether the next delta distance is greater than or equal to zero. When it is not, the method continues at step 218.

When the next delta distance is greater than or equal to zero, the method continues at step 224 where the processing module adds the next delta distance to an accumulation of previous delta distances to produce an updated accumulation of delta distances. The method continues to step 226 where the processing module determines whether the time period has ended. When the time period has not ended, the method repeats as step 218.

When the next sampling point corresponds to the end of the time period, the method continues at step 228 where the processing module provides the updated accumulation of delta distances as the elevation change that occurred during the time period. For example, the accumulated z distance is 100 feet, which can be equated to ascending 10 flights of stairs.

FIG. 26B is a logic diagram of another example of a method executed by a shoe sensor system to determine negative elevation tracking (e.g., descending) for the time period while performing the physical activity. The method begins at step 230 where the processing module (e.g., processing module 30 of the system 10 and/or processing module 27 of the computing device 25) determines a first z coordinate from a first three-dimensional foot data point (e.g., first x-y-z coordinate as previously described) that corresponds to the beginning of the time period.

The method continues at step 232 where the processing module determines a next z coordinate from a next three-dimensional foot data point (e.g., a next x-y-z coordinate as previously discussed) that corresponds to a next sampling point of the sampling clock within the time period. The method continues at step 234 where the processing module determines a next delta distance based on a difference between the first z coordinate and the next z coordinate. The method continues at step 236 where the processing module determines whether the next delta distance is less than or equal to zero. When it is not, the method continues at step 218.

When the next delta distance is less than or equal to zero, the method continues at step 238 where the processing module adds the next delta distance to an accumulation of previous delta distances to produce an updated accumulation of delta distances. The method continues to step 240 where the processing module determines whether the time period has ended. When the time period has not ended, the method repeats as step 218.

When the next sampling point corresponds to the end of the time period, the method continues at step 242 where the processing module provides the updated accumulation of delta distances as the elevation change that occurred during the time period. For example, the accumulated z distance is −100 feet, which can be equated to descending 10 flights of stairs.

Figure 27:
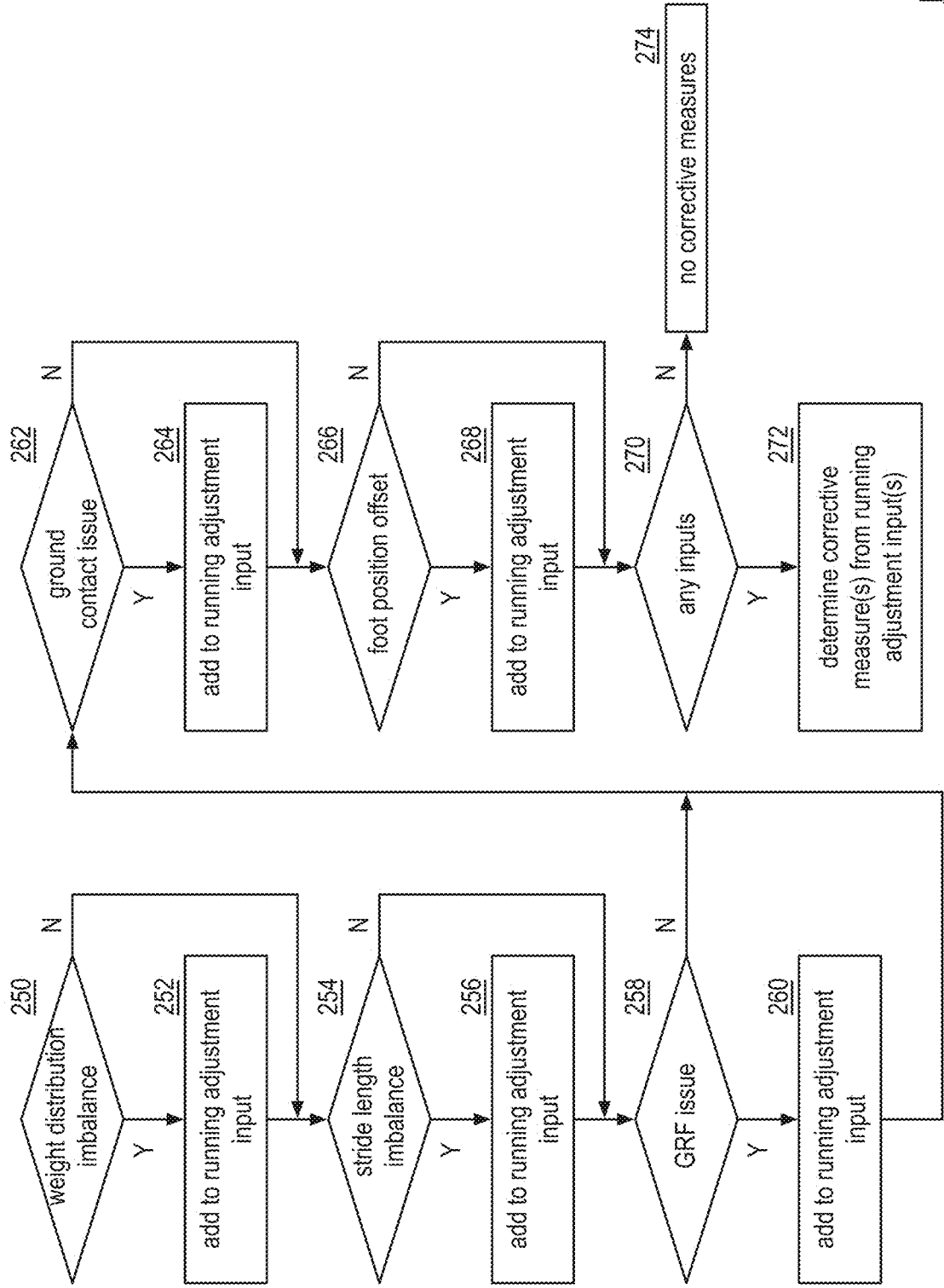
FIG. 27 is a logic diagram of another example of a method executed by a shoe sensor system in accordance with the present invention.

FIG. 27 is a logic diagram of another example of a method executed by a shoe sensor system to determine running optimization, which includes one or more of proper foot positioning, proper weight distribution, balanced strides, stride length training, increase ground reaction force, reduce foot to ground contact time, etc. The method begins at step 250 where the processing module (e.g., processing module 30 of the system 10 and/or processing module 27 of the computing device 25) determines whether there is a weight imbalance between strides, over a number of strides, and/or over a period of time. For example, a weight imbalance is detected when more force is exerted when one foot strikes the ground versus the other shoe. If yes, the method continues at step 252 where the processing module adds weight distribution issue to a list of running adjustment inputs.

When the weight distribution issue has been added to the running adjustments inputs or there is not a weight distribution issue, the method continues at step 254 where the processing module determines whether a stride length imbalance exists. If yes, the method continues at step 256 where the processing module adds stride length imbalance issue to a list of running adjustment inputs.

When the stride length imbalance issue has been added to the running adjustments inputs or there is not a stride length imbalance issue, the method continues at step 258 where the processing module determines whether a ground reaction force (GRF) issue exists. For example, GRF is the force between the foot and the ground when running. If the GRF is too low, the person is not driving his or her legs hard enough. If the GRF is too high, then the person may be landing wrong, driving too hard, etc. If the GRF issues exists, the method continues at step 260 where the processing module adds the GRF issue to a list of running adjustment inputs.

When the GRF issue has been added to the running adjustments inputs or there is not a GRF issue, the method continues at step 262 where the processing module determines whether a ground contact issue exists. For example, for speed, a runner desired a minimum amount of contact time with the ground per stride. When the contact time with the ground is too high, the runner is losing time. If the ground contact issue exists, the method continues at step 264 where the processing module adds the ground contact issue to a list of running adjustment inputs.

When the ground contact issue has been added to the running adjustments inputs or there is not a ground contact issue, the method continues at step 266 where the processing module determines whether a foot position offset exists. For example, the processing interprets the correlated foot data to determine that foot positioning is offset by at least a foot positioning threshold from an optimal foot positioning. For example, the left foot rolls out several inches when striding from the left foot to left foot contact with the ground. This wastes energy and may lead to an injury. If there is a foot position offset, the method continues at step 268 where the processing module adds the foot position offset to a list of running adjustment inputs.

The method continues at step 220 where the processing module determines whether any inputs are in the running adjustment inputs. If not, the method continues at step 274 where no corrective measures are provided. If, however, there is at least one input in the running adjustment inputs, the method continues at step 272 where the processing module generates one or more corrective measures based on the running adjustment inputs. The corrective measures include training for improving stride length, reducing contact time, improving GRF, etc.

Figure 28:
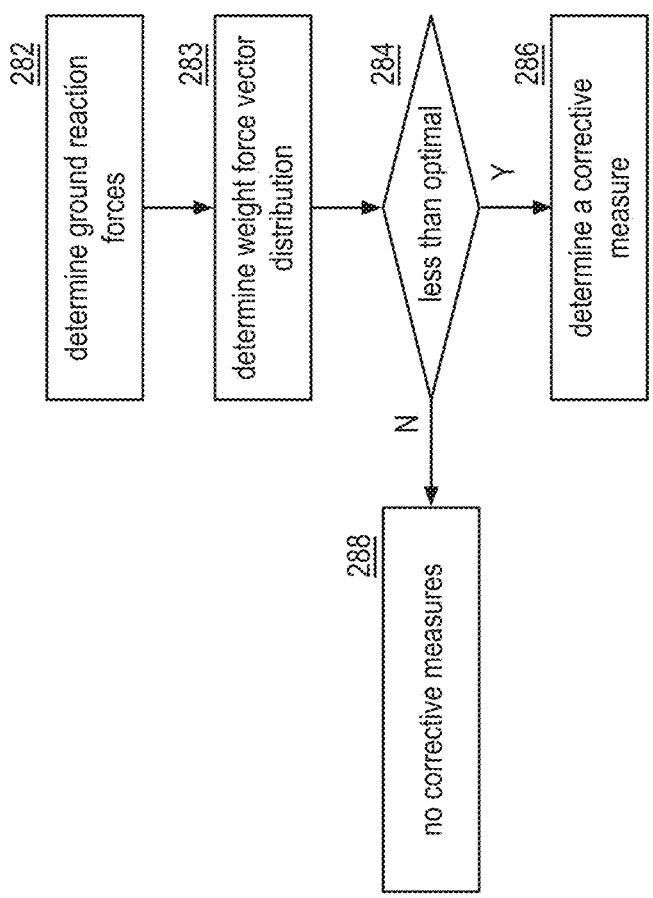
FIG. 28 is a logic diagram of another example of a method executed by a shoe sensor system in accordance with the present invention.

FIG. 28 is a logic diagram of another example of a method executed by a shoe sensor system to determine the rotational sport optimization (e.g., improve weight distribution, improve GRF, improve balance, improve linear movement, improve rotational movement, improve linear and/or rotation power, etc.). The method begins at step 282 where the processing module determines ground reaction force during performance of an athletic movement of a rotational sport (e.g., baseball, golf, tennis, lacrosse, football, basketball, etc.).

The method continues at step 283 where the processing module determines weight force vector distribution between medial and lateral side of the foot and between forefoot and heel based on the ground reaction forces. The method continues at step 284 where the processing module determines whether the weight force vector distribution is less than optimal. When it is not, the method continues at step 288 where no corrective measures are provided. When the weight force vector distribution is less than optimal, the method continues at step 286 where the processing module determines a corrective measure to optimize the weight force vector distribution during performance of the athletic movement.

It is noted that terminologies as may be used herein such as bit stream, stream, signal sequence, etc. (or their equivalents) have been used interchangeably to describe digital information whose content corresponds to any of a number of desired types (e.g., data, video, speech, audio, etc. any of which may generally be referred to as 'data').

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While the transistors in the above described figure(s) is/are shown as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A method for execution by a processing module, the method comprises:

obtaining foot force data that is created by sampling, in accordance with a sampling signal, data from a plurality of pressure sensing elements of a shoe sensor system, wherein the plurality of pressure sensing elements are distributed in a pattern having a first pressure sensing element at a fifth metatarsal area of a lateral wall of an insole of a shoe associated with the shoe sensor system, and a second pressure sensing element at a first metatarsal area of a medial wall of the insole; and processing the foot force data to determine a horizontal force of a foot of a user of the shoe sensor system while the user is performing a movement while wearing the shoe.

2. The method of claim 1 further comprises:

obtaining three-dimensional foot data that is created by sampling, in accordance with the sampling signal, data from a first accelerometer of the shoe sensor system, wherein the first accelerometer is positioned within the pattern;

correlating the foot force data and the three-dimensional foot data in accordance with the sampling signal to produce correlated foot data; and processing the correlated foot data to determine one or more of: distance traveled during a time period, stride length data, fatigue indication, injury prevention indicators, time duration, elevation tracking for the time period, running optimization, and rotational sport optimization.

3. The method of claim 2 further comprises:

the obtaining the foot force data includes receiving, by the processing module of the shoe sensor system, the foot force data from the plurality of pressure sensing elements; and the obtaining the three-dimensional foot data includes receiving, by the processing module of the shoe sensor system, the three-dimensional foot data from the first accelerometer.

4. The method of claim 2 further comprises:

the obtaining the foot force data includes receiving, by the processing module of a computing device, the foot force data from a transmitter of the shoe sensor system; and the obtaining the three-dimensional foot data includes receiving, by the processing module of the computing device, the three-dimensional data from the transmitter of the shoe sensor system.

5. The method of claim 2, wherein the three-dimensional foot data comprises one or more of:

an accelerometer identifier;

an x-y-z origin coordinate;

a plurality of x-y-z coordinate values;

a first plurality of representations of x-y-z coordinate values; and a first plurality of x-y-z coordinates.

6. The method of claim 2, wherein the correlating the foot force data and the three-dimensional foot data comprises:

for a first sampling interval of the sampling signal:
identifying a first foot force data point of the foot force data and a first three-dimensional foot data point of the three-dimensional foot data; and
linking the first foot force data point with the first three-dimensional foot data point and with the first sampling interval; and for a second sampling interval of the sampling signal:
identifying a second foot force data point of the foot force data and a second three-dimensional foot data point of the three-dimensional foot data; and
linking the second foot force data point with the second three-dimensional foot data point and with the second sampling interval.

7. The method of claim 2, wherein the processing the correlated foot data to determine the distance traveled during the time period comprises:

determining a first x-y coordinate from a first three-dimensional foot data point that corresponds to a beginning of the time period;

determining a next x-y coordinate from a next three-dimensional foot data point that corresponds to a next sampling point of a sampling clock within the time period;

determining a next delta distance based on a difference between the first x-y coordinate and the next x-y coordinate;

adding the next delta distance to an accumulation of previous delta distances to produce an updated accumulation of delta distances;

when the next sampling point corresponds to an end of the time period, provided the updated accumulation of delta distances as the distance traveled during the time period; and when the next sampling point does not correspond to the end of the time period, repeating the steps for subsequent sampling points until the next sampling point interval corresponds to the end of the time period.

8. The method of claim 2, wherein the processing the correlated foot data to determine the stride length data comprises:

determining a first left x-y coordinate from a first left three-dimensional foot data point that corresponds to a left foot being in contact with a surface;

determining a first right x-y coordinate from a first right three-dimensional foot data point that corresponds to a right foot being in contact with the surface; and determining a left foot to right foot stride length based on the first left x-y coordinate and the first right x-y coordinate.

9. The method of claim 2, wherein the processing the correlated foot data to determine the time duration comprises:

counting clock cycle of a clock signal from a beginning of the time duration until an end of the time duration to produce a clock cycle count; and interpreting the clock cycle count in light of a clock rate of the clock signal to determine the time duration.

10. The method of claim 2, wherein the processing the correlated foot data to determine the fatigue indication comprises:

detecting, based on changes in the correlated foot data over time within the time period, one or more of a shortening of stride length, a slowing of pace, and a change in foot force; and interpreting the one or more of the shortening of stride length, the slowing of pace, and the change in foot force to determine a fatigue level.

11. The method of claim 2, wherein the processing the correlated foot data to determine the injury prevention indicators comprises:

detecting, based on changes in the correlated foot data over time within the time period, one or more of an imbalance in foot force between feet, a change in foot forces of one or both feet, an imbalance in stride lengths, an imbalance in stride height between the feet, and foot movement outside of a movement deviation range;

interpreting the one or more of the imbalance in foot force between the feet, the change in foot forces of one or both feet, the imbalance in stride lengths, the imbalance in stride height between the feet, and the foot movement outside of the movement deviation range to identify a potential injury; and determining a preventive measure based on the potential injury and the one or more of the imbalance in foot force between the feet, the change in foot forces of one or both feet, the imbalance in stride lengths, the imbalance in stride height between the feet, and the foot movement outside of the movement deviation range.

12. The method of claim 2, wherein the processing the correlated foot data to determine the elevation tracking for the time period comprises:
determining a first z coordinate from a first three-dimensional foot data point that corresponds to a beginning of the time period;
determining a next z coordinate from a next three-dimensional foot data point that corresponds to a next sampling point of a sampling clock within the time period;
determining a next delta distance based on a difference between the first z coordinate and the next z coordinate;
when the next delta distance is greater than or equal to zero, adding the next delta distance to an accumulation of previous delta distances to produce an updated accumulation of delta distances;
when the next sampling point corresponds to an end of the time period, provided the updated accumulation of delta distances as an elevation change that occurred during the time period; and
when the next sampling point does not correspond to the end of the time period, repeating all but the determining the first z coordinate from the first three-dimensional foot data point that corresponds to the beginning of the time period for another next three-dimensional foot data point until the next sampling point corresponds to the end of the time period.

13. The method of claim 2, wherein the processing the correlated foot data to determine the running optimization comprises one or more of:
interpreting the correlated foot data to determine foot positioning while running is offset by at least a foot positioning threshold from an optimal foot positioning and providing a corrective measure to reduce the offset;
interpreting the correlated foot data to determine that, while running, weight distribution between the left foot and the right foot are imbalanced and providing a correct measure to reduce the weight distribution imbalance;
interpreting the correlated foot data to determine that, while running, stride lengths are imbalanced between a left-to-right stride and a right-to-left stride and providing a correct measure to reduce the stride lengths imbalance;
interpreting the correlated foot data to determine that, while running, ground reaction force are below an optimal level and providing a correct measure to improve the ground reaction force; and
interpreting the correlated foot data to determine that, while running, ground contact time is above an optimal level and providing a correct measure to reduce the ground contact time.

14. The method of claim 2, wherein the processing the correlated foot data to determine the rotational sport optimization comprises:
determining a ground reaction force during performance of an athletic movement of a rotational sport;
determining a weight force vector distribution between medial and lateral side of the foot and between forefoot and heel based on the ground reaction force; and
when the weight force vector distribution is less than optimal, determining a corrective measure to optimize the weight force vector distribution during performance of the athletic movement.

15. The method of claim 2 further comprises:
obtaining second three-dimensional foot data that is created by sampling, in accordance with the sampling signal, data from a second accelerometer of the shoe sensor system, wherein the second accelerometer is positioned within the pattern at a distance from the first accelerometer;
correlating the foot force data, the three-dimensional foot data, and the second three-dimensional foot data in accordance with the sampling signal to produce the correlated foot data; and
processing the correlated foot data to determine various foot orientations during the time period.

16. The method of claim 1 further comprises:
obtaining biometric data from one or more biometric sensors of the shoe sensor system; and
interpreting the biometric data to provide information regarding one or more of temperature, moisture, heart rate, and respiration rate.

17. The method of claim 1, wherein a pressure sensing element of the plurality of pressure sensing elements comprises one or more of:
resistive pressure sensor, a piezoelectric pressure sensor, a capacitive pressure sensor, and an inductive pressure sensor.

18. The method of claim 1, wherein the foot force data comprises one or more of:
from the first pressure sensing element of the plurality of pressure sensing elements:
a first pressure sensor indicator;
a first plurality of pressure sensed values;
a first plurality of representations of sensed pressure levels; and
a first plurality of pressure measurements; and
from the second pressure sensing element of the plurality of pressure sensing elements:
a second pressure sensor indicator;
a second plurality of pressure sensed values;
a second plurality of representations of sensed pressure levels; and
a second plurality of pressure measurements.

19. The method of claim 1, wherein the pattern further comprises:
a third pressure sensing element at a medial ball of foot area, and
a fourth pressure sensing element at a lateral heel area.

20. The method of claim 1, wherein the pattern further comprises:
a third pressure sensing element at a lateral ball of foot area, and
a fourth pressure sensing element at a medial heel area.

* * * * *